US010265699B2

(12) United States Patent
Liddle et al.

(10) Patent No.: US 10,265,699 B2
(45) Date of Patent: Apr. 23, 2019

(54) VACUUM COMPATIBLE FLUID SAMPLER

(71) Applicant: The United States of America, as Represented by the Secretary of Commerce, Washington, DC (US)

(72) Inventors: J. Alexander Liddle, Rockville, MD (US); Samuel M. Stavis, North Potomac, MD (US); Glenn E. Holland, Rockville, MD (US)

(73) Assignee: THE UNITED STATES OF AMERICA, AS REPRESENTED BY THE SECRETARY OF COMMERCE, Washington, DC (US)

( * ) Notice: Subject to any disclaimer, the term of this patent is extended or adjusted under 35 U.S.C. 154(b) by 51 days.

(21) Appl. No.: 15/611,564

(22) Filed: Jun. 1, 2017

(65) Prior Publication Data

US 2017/0348687 A1    Dec. 7, 2017

Related U.S. Application Data

(60) Provisional application No. 62/343,909, filed on Jun. 1, 2016.

(51) Int. Cl.
*H01L 21/3065* (2006.01)
*H01L 21/311* (2006.01)
(Continued)

(52) U.S. Cl.
CPC ..... *B01L 3/50273* (2013.01); *B01L 3/502707* (2013.01); *B01L 9/00* (2013.01);
(Continued)

(58) Field of Classification Search
None
See application file for complete search history.

(56) References Cited

U.S. PATENT DOCUMENTS 6,001,229 A    12/1999  Ramsey
8,059,271 B2   11/2011  Marsh et al.
(Continued)

OTHER PUBLICATIONS

Sparreboom et al, Rapid sacrificial layer etching for the fabrication of nanochannels with integrated metal electrodes, Jan. 2008, Lap Chip, vol. 8, p. 402-407. (Year: 2008).*
(Continued)

*Primary Examiner* — Stephanie P Duclair
(74) *Attorney, Agent, or Firm* — Office of Chief Counsel for National Institute of Standards and Technology

(57) ABSTRACT

A fluid sampler includes: a sample cell that includes: a substrate comprising: a first port; a second port in fluid communication with the first port; a viewing reservoir in fluid communication with the first port and the second port and that receives the fluid from the first port and communicates the fluid to the second port, the viewing reservoir including: a first view membrane; a second view membrane; and a pillar interposed between the first view membrane and second view membrane, the pillar separating the first view membrane from the second view membrane at a substantially constant separation distance such that a volume of the viewing reservoir is substantially constant and invariable with respect to a temperature and invariable with respect to a pressure to which the sample cell is subjected.

20 Claims, 63 Drawing Sheets

(51) Int. Cl.

| | |
|---|---|
| H01L 21/4757 | (2006.01) |
| B01L 3/00 | (2006.01) |
| B01L 9/00 | (2006.01) |
| G01N 1/00 | (2006.01) |
| G01N 35/00 | (2006.01) |
| G01N 27/447 | (2006.01) |
| G01N 23/04 | (2018.01) |
| G01N 23/02 | (2006.01) |
| G01N 23/2251 | (2018.01) |
| G01N 1/28 | (2006.01) |
| H01J 37/16 | (2006.01) |

(52) U.S. Cl.
CPC ............... *G01N 1/28* (2013.01); *G01N 23/02* (2013.01); *G01N 23/04* (2013.01); *G01N 23/2251* (2013.01); *G01N 27/4473* (2013.01); *G01N 27/44791* (2013.01); *G01N 35/0099* (2013.01); *H01J 37/16* (2013.01); *H01L 21/3065* (2013.01); *H01L 21/31122* (2013.01); *H01L 21/47573* (2013.01); *B01L 2200/12* (2013.01); *B01L 2300/046* (2013.01); *B01L 2300/06* (2013.01); *B01L 2300/0609* (2013.01); *B01L 2300/0681* (2013.01); *B01L 2300/0867* (2013.01); *B01L 2300/0887* (2013.01); *B01L 2300/0896* (2013.01); *B01L 2400/0415* (2013.01); *G01N 2223/307* (2013.01); *G01N 2223/418* (2013.01); *G01N 2223/638* (2013.01); *H01L 2924/1067* (2013.01)

(56) References Cited

U.S. PATENT DOCUMENTS

| | | | |
|---|---|---|---|
| 8,102,523 B1 | 1/2012 | Marsh et al. | |
| 8,333,934 B2 | 12/2012 | Cao et al. | |
| 2012/0182548 A1 | 7/2012 | Harb et al. | |
| 2012/0298883 A1* | 11/2012 | Grogan | H01J 37/20 250/440.11 |

OTHER PUBLICATIONS

Fursina et al, Nanogaps with very large aspect ratios for electrical measurements, Mar. 2008, Applied Physics Letters, 92, 113102-1-113102-3. (Year: 2008).*
Abrams, I.M., et al., A Closed Cell for Electron Microscopy. Journal of Applied Physics, 1944, 607-609, 15(8).
Baker, R.T.K., et al., Controlled atmosphere electron microscopy. Journal of Physics E: Scientific Instruments, 1972, 793, 5(8).
Bell, A.T., The Impact of Nanoscience on Heterogeneous Catalysis. Science, 2003, 1688-1691, 299(5613).
Chen, Q., et al., 3D Motion of DNA—Au Nanoconjugates in Graphene Liquid Cell Electron Microscopy. Nano Letters, 2013, 4556-4561, 13(9).
Creemer, J.F., et al., Atomic-scale electron microscopy at ambient pressure, Ultramicroscopy, 2008, 993-998, 108(9).
De Jonge, N., et al., Electron microscopy of whole cells in liquid with nanometer resolution, Proceedings of the National Academy of Sciences, 2009.
De Jonge, N., et al., Nanometer-resolution electron microscopy through micrometers-thick water layers, Ultramicroscopy, 2010, 1114-1119, 110(9).
De Jonge, N., et al., Electron microscopy of specimens in liquid. Nat Nano, 2011, 695-704, 6(11).
Dukes, M.J., et al., Visualizing nanoparticle mobility in liquid at atomic resolution, Chemical Communications, 2013, 3007-3009, 49(29).
Gai, P., Developments in in situ Environmental Cell High-Resolution Electron Microscopy and Applications to catalysis, Topics in Catalysis, 2002, 161-173, 21(4).
Grogan, J.M., et al., The Nanoaquarium: A Platform for In Situ Transmission Electron Microscopy in Liquid Media, Journal of Microelectromechanical Systems, 2010, 885-894, 19(4).
Gu, M., et al., Demonstration of an Electrochemical Liquid Cell for Operando Transmission Electron Microscopy Dbservation of the Lithiation/Delithiation Behavior of Si Nanowire Battery Anodes, Nano Letters, 2013, 6106-6112, 13 (12).
Holtz, M.E., et al., In Situ Electron Energy-Loss Spectroscopy in Liquids, Microscopy and Microanalysis, 2013, 1027-1035, 19(04).
Jeangros, Q., et al., In situ redox cycle of a nickel-YSZ fuel cell anode in an environmental transmission electron microscope, Acta Materialia, 2010, 4578-4589, 58(14).
Jensen, E., et al., Monolithic Chip System with a Microlluidic Channel for In Situ Electron Microscopy of Liquids, Microscopy and Microanalysis, 2014, 445-451, 20(02).
Jungjohann, K.L., et al., Atomic-Scale Imaging and Spectroscopy for In Situ Liquid Scanning Transmission Electron Microscopy, Microscopy and Microanalysis, 2012, 621-627, 18(03).
Li, D. et al., Direction-Specific Interactions Control Crystal Growth by Oriented Attachment, Science, 2012, 1014-1018, 336(6084).
Liao, H.-G., et al., Facet development during platinum nanocube growth, Science, 2014, 916-919, 345(6199).
Liu, K.-L., et al., Novel microchip for in situ TEM imaging of living organisms and bio-reactions in aqueous conditions, Lab on a Chip, 2008, 1915-1921, 8(11).
Marton, L., La microscopie electronique des objets biologiques, Bull. de L'Acad. Royale de Belgique, 1935, 553-560, 21.
Radisic, A., et al., In Situ Study of the Growth Kinetics of Individual Island Electrodeposition of Copper, The Journal of Physical Chemistry B, 2006, 7862-7868, 110(15).
Radisic, A., et al., Quantifying Electrochemical Nucleation and Growth of Nanoscale Clusters Using Real-Time Kinetic Data, Nano Letters, 2006, 238-242, 6(2).
Ross, F.M., Controlling nanowire structures through real time growth studies, Reports on Progress in Physics, 2010, 114501, 73(11).
Sharma, R., Design and Applications of Environmental Cell Transmission Electron Microscope for in Situ Observations of Gas-Solid Reactions, Microscopy and Microanalysis, 2001, 494-506, 7(06).
Sharma, R., et al., Observation of dynamic nanostructural and nanochemical changes in ceria-based catalysts during in-situ reduction, Philosophical Magazine, 2004, 2731-2747, 84(25-26).
Sharma, R., et al., Dynamic observations of the effect of pressure and temperature conditions on the selective synthesis of carbon nanotubes, Nanotechnology, 2007, 125602, 18(12).
Smeets, P.J.M., et al., Calcium carbonate nucleation driven by ion binding in a biomimetic matrix revealed by in situ alectron microscopy, Nat Mater, 2015, 394-399, 14(4).
Swift, J.A., et al., An environmental cell for the examination of wet biological specimens at atmospheric pressure by transmission scanning electron microscopy, Journal of Physics E: Scientific Instruments, 1970, 924, 3(11).
Vendelbo, S.B., et al., Visualization of oscillatory behaviour of Pt nanoparticles catalysing CO oxidation, Nat Mater advance online publication, 2014.
Wang, C.-M., et al., Observation of materials processes in liquids by electron microscopy, MRS Bulletin, 2015, 46-52, 40(01).
Wang, C., et al., High-Resolution Electron Microscopy and Spectroscopy of Ferritin in Biocompatible Graphene Liquid Cells and Graphene Sandwiches, Advanced Materials, 2014, 3410-3414, 26(21).
Wang, R., et al., Structural Transformation in Ceria Nanoparticles during Redox Processes, The Journal of Physical chemistry C, 2009, 5700-5704, 113(14).
Williamson, M.J., et al., Dynamic microscopy of nanoscale cluster growth at the solid-liquid interface, Nat Mater, 2003, 532-536, 2(8).
Yuk, J.M., et al., High-Resolution EM of Colloidal Nanocrystal Growth Using Graphene Liquid Cells, Science, 2012, 51-64, 336(6077).
Zheng, H., et al., Observation of Single Colloidal Platinum Nanocrystal Growth Trajectories, Science, 2009, 1309-1312, 324(5932).

(56) References Cited

OTHER PUBLICATIONS

Wu, F., et al., Advances in sealed liquid cells for in-situ TEM electrochemical investigation of lithium-ion battery, Science Direct, 2014, 1-15.
Dukes, M., et al., Improved microchip design and application for In situ transmission electon microscopy of macromolecules, Microscopy and Microanalysis, 2014, 338-345.
Egawa, M. et al., In-situ realtime monitoring of nanoscale gold electroplating using micro-electro-mechanical systems liquid cell operating in transmission electron microscopy, Applied Physics Letters, 2016, 023104-1-023104-4, 108.
Grogan, J.M., et al., The nanoaquarium: A new paradigm in electron microscopy, Journal of the Indian Institute of Science, 2012, 295-308, 92(2).
Klein, K.L.,et al., Transmission electron microscopy with a liquid flow cell, Journal of Microscopy, 2011, 117-123, 242.
Leenheer, A.J., et al., A sealed liquid cell for in situ transmission electron microscopy of controlled electrochemical process, Journal of Microelectromechanical Systems, 2015, 1061-1068, 24(4).
Tanase, M., et al., High-resolution imaging and spectroscopy at high pressure: a novel liquid cell for the transmission alectron microscope, Microscopy and Microanalysis, 2015, 1629-1638, 21.
Ring. E.A., et al., Mircrofluidic system for transmission electron microscopy, Microscopy and Microanalysis, 2010, 622-629, 16.
Bartholomew, C.H., et al., Fundamentals of industrial catalytic processes, 2006, Second Edition.

\* cited by examiner (A)

(B)

(A)

(B)

(A)

(B)

(A)

(B)

(C)

(A)

(B)

(C)

(A)

(B)

(C)

(A)

(B)

VACUUM COMPATIBLE FLUID SAMPLER

CROSS REFERENCE TO RELATED APPLICATIONS

This application claims the benefit of U.S. Provisional Patent Application Ser. No. 62/343,909, filed Jun. 1, 2016, the disclosure of which is incorporated herein by reference in its entirety.

STATEMENT REGARDING FEDERALLY SPONSORED RESEARCH

This invention was made with United States Government support from the National Institute of Standards and Technology, an agency of the United States Department of Commerce. The Government has certain rights in the invention.

BRIEF DESCRIPTION

Disclosed is a fluid sampler comprising: a sample cell that comprises: a substrate comprising: a first end; a second end opposing the first end; a first surface traversing a length of the substrate from the first end to the second end; and a second surface opposing the first surface and traversing the length of the substrate from the first end to the second end; a first port disposed in the substrate and that receives a fluid; a second port disposed in the substrate and in fluid communication with the first port; a viewing reservoir disposed on the substrate in fluid communication with the first port and the second port and that receives the fluid from the first port and communicates the fluid to the second port, the viewing reservoir comprising: a first view membrane disposed on the first surface of the substrate; and a second view membrane disposed on the second surface of the substrate, wherein the fluid is interposed between the first view membrane and the second view membrane; and a pillar interposed between the first view membrane and the second view membrane, the pillar separating the first view membrane from the second view membrane at a substantially constant separation distance such that a volume of the viewing reservoir is substantially constant and invariable with respect to a temperature and invariable with respect to a pressure to which the sample cell is subjected, wherein the pillar, the first view membrane, and the second view membrane are monolithic.

Disclosed also is a process for selectively removing a sacrificial member from a composite structure, the process comprising: providing a first structural layer; disposing the sacrificial member on the first structural layer, the sacrificial member comprising chromium oxide; disposing a second structural layer on the sacrificial member such that: the sacrificial member is interposed between the first structural layer and the second structural layer, and a composite structure is formed by the first structural layer and the second structural layer; contacting the sacrificial member with an etchant, the etchant being selective to etch chromium oxide and substantially inert with respect to etching the composite structure; and selectively etching the sacrificial member by the etchant to selectively remove the sacrificial member from the composite structure, wherein the first structural layer and the second structural layer are spaced apart by a separation distance by removal of the sacrificial member.

Further discloses is a process for making a sample cell, the process comprising: providing a substrate; disposing a first structural layer on a second surface of the substrate; disposing a third structural layer on the first surface of the substrate; disposing a first oxide layer on the first structural layer: disposing a plurality of electrodes on the first oxide layer; disposing a sacrificial member on the first oxide layer, the sacrificial member comprising: chromium oxide; a first thickness in contact with a portion of each electrode; and a second thickness that is less than then the first thickness in an area on the substrate that corresponds to a viewing reservoir; forming a plurality of apertures in the sacrificial member; disposing a second oxide layer on the sacrificial member such that the sacrificial member is interposed between the second oxide layer and the first structural layer; disposing a second structural layer on the second oxide layer such that the sacrificial member is interposed between the second structural layer and the first structural layer; etching the third structural layer to expose the substrate at the first surface; forming an etchant trench on the second surface; etching a portion of the substrate from the first surface to the second surface to expose a portion of the first structural layer in an area that corresponds to a viewing reservoir and a fluid port; and selectively etching the sacrificial member removing the sacrificial member from between the first structural layer and the second structural layer to form the sample cell.

BRIEF DESCRIPTION OF THE DRAWINGS

The following descriptions should not be considered limiting in any way. With reference to the accompanying drawings, like elements are numbered alike.

DETAILED DESCRIPTION

Figure 1:
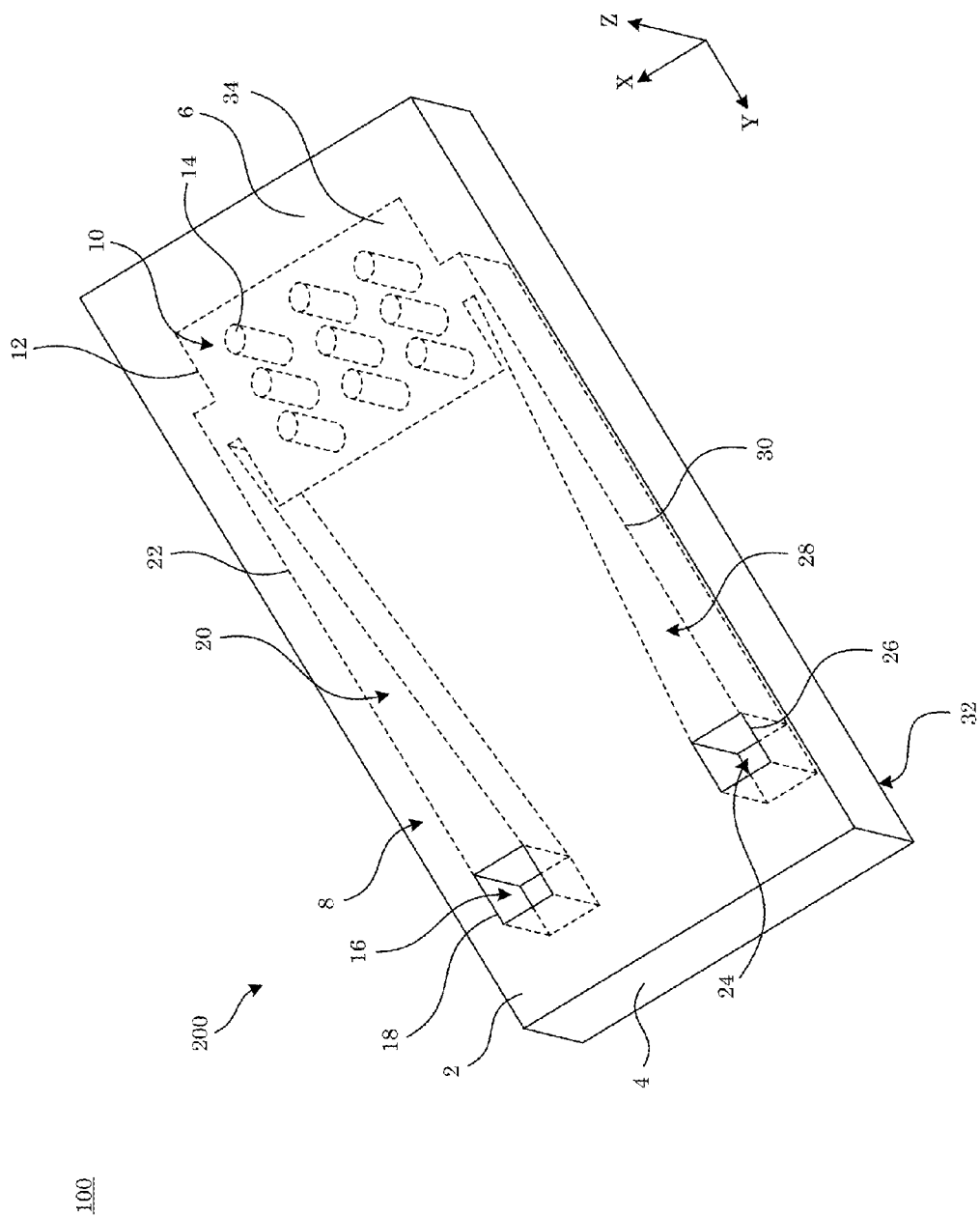
FIG. 1 shows a perspective view of a fluid sampler that includes a sample cell.

A detailed description of one or more embodiments is presented herein by way of exemplification and not limitation.

It has been discovered that a fluid sampler herein includes a monolithic sample cell for imaging and spectroscopy, of a fluid, e.g., a thin liquid layer. The fluid sampler provides for encapsulating and obtaining high-resolution imaging and spectroscopic measurements of the fluid, e.g., in a transmission electron microscope (TEM). The sample cell can be nanofabricated so that the fluid is separated from vacuum of the TEM. Moreover, the fluid sampler provides fluid flow, combining, heating, and application of voltage for, e.g. electrochemical studies. Additionally, the fluid sampler is vacuum compatible and includes a plurality of inputs (e.g., an electrical feedthrough) for communication with an exterior of the TEM's.

In an embodiment, with reference to FIG. 1, FIG. 2, FIG. 3, FIG. 4, and FIG. 5, fluid sampler 100 includes sample cell 200 that includes: substrate 2 including: first end 4; second end 6 opposing first end 4; first surface 8 traversing a length of substrate 2 from first end 4 to second end 6; and second surface 32 opposing first surface 8 and traversing the length of substrate 2 from first end 4 to second end 6; first port 16 bounded by wall 18 disposed in substrate 2 and that receives a fluid; second port 24 bounded by wall 26 disposed in substrate 2 and in fluid communication with first port 16; viewing reservoir 10 bounded by wall 12 disposed on substrate 2 in fluid communication with first port 16 and second port 24 and that receives the fluid from first port 16 and communicates the fluid to second port 24, viewing reservoir 10 including: first view membrane 34 disposed on first surface 8 of substrate 2; and second view membrane 36 disposed on second surface 32 of substrate 2, wherein the fluid when present is interposed between first view membrane 34 and second view membrane 36; and pillar 14 interposed between first view membrane 34 and second view membrane 36, pillar 14 separating first view membrane 34 from second view membrane 36 at a substantially constant separation distance D1 such that a volume of viewing reservoir 10 is substantially constant and invariable with respect to a temperature and invariable with respect to a pressure to which sample cell 200 is subjected. Here, pillar 14, first view membrane 34, and second view membrane 36 are monolithic.

Sample cell 200 also can include first conduit 20 bounded by wall 22 such that first conduit 20 is in fluid communication with first port 16 and viewing reservoir 10 and interposed between first port 16 and viewing reservoir 10, wherein first conduit 20 communicates the fluid from first port 16 to viewing reservoir 10. Sample cell 200 also can include second conduit 28 bounded by wall 30. Second conduit 28 is in fluid communication with second port 24 and viewing reservoir 10 and interposed between second port 24 and viewing reservoir 10, wherein second conduit 28 communicates fluid from viewing reservoir 10 to second port 24.

Figure 6:
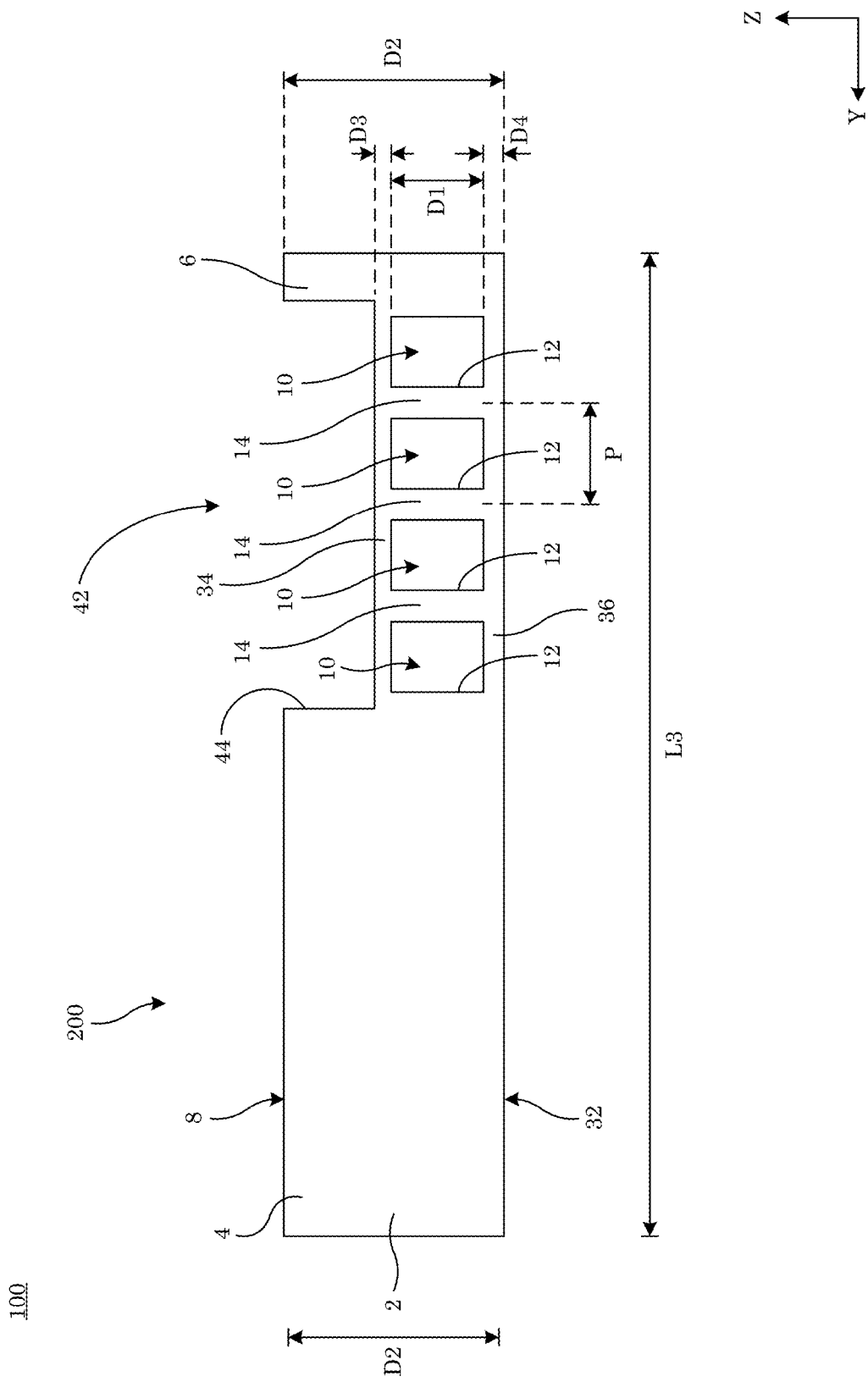
FIG. 6 shows a cross-section along line A-A view of the fluid sampler shown in FIG. 2 according to an embodiment.

In an embodiment, as shown in FIG. 6 (an exemplary cross-section through line A-A of FIG. 2), cell 200 includes recess 42 bounded by wall 44 at viewing reservoir 10 to provide a selected thickness for viewing reservoir 10. Here, first end 4 can have thickness D2 that is different than thickness D1 of viewing reservoir 10. Moreover, first view membrane 34 and second view membrane 36 of viewing reservoir 10 respectively have thicknesses (D3, D4) that can be the same or different from each other.

Figure 7:
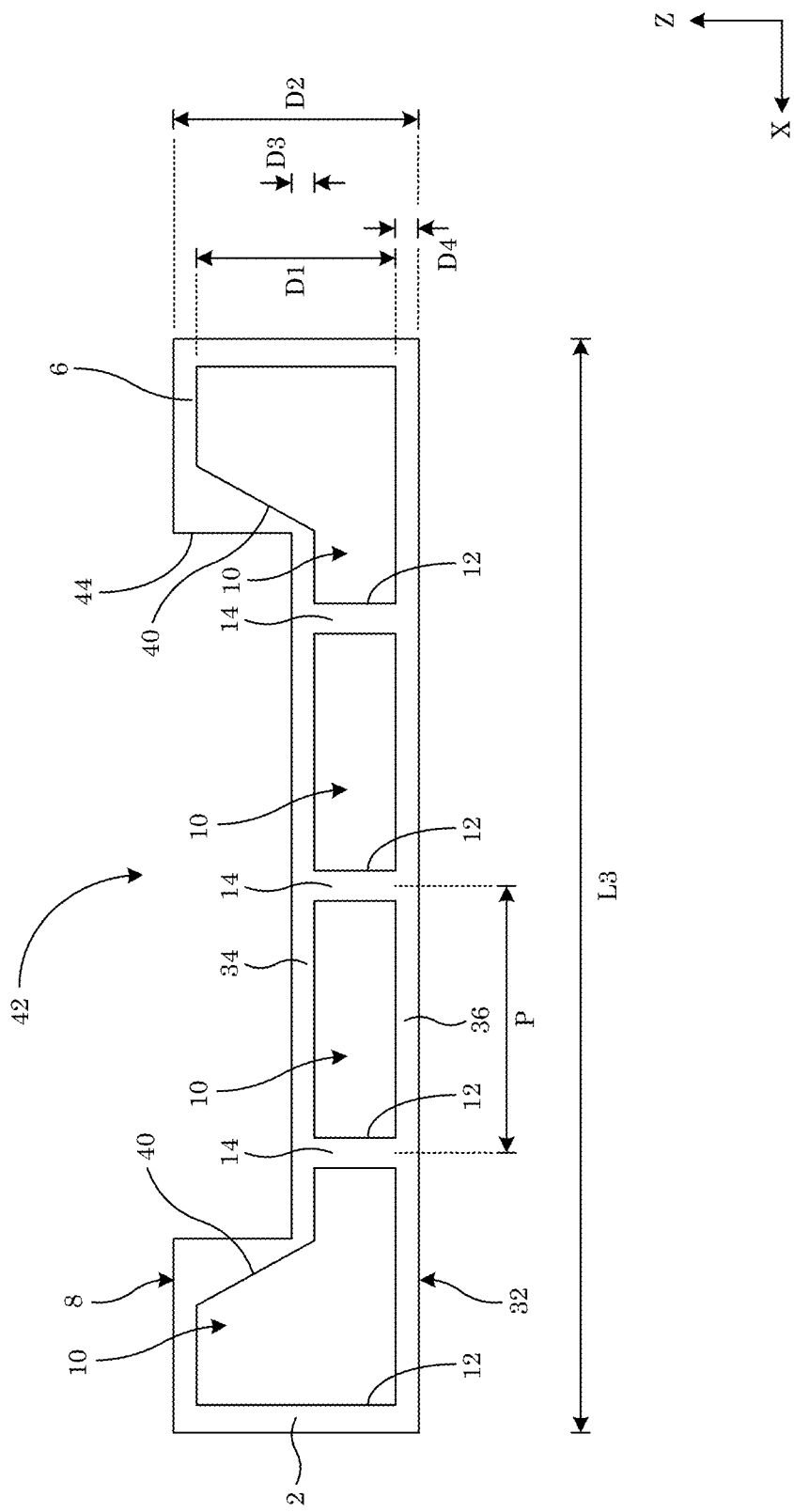
FIG. 7 shows a cross-section along line B-B of the fluid sampler shown in FIG. 2.
Figure 8:
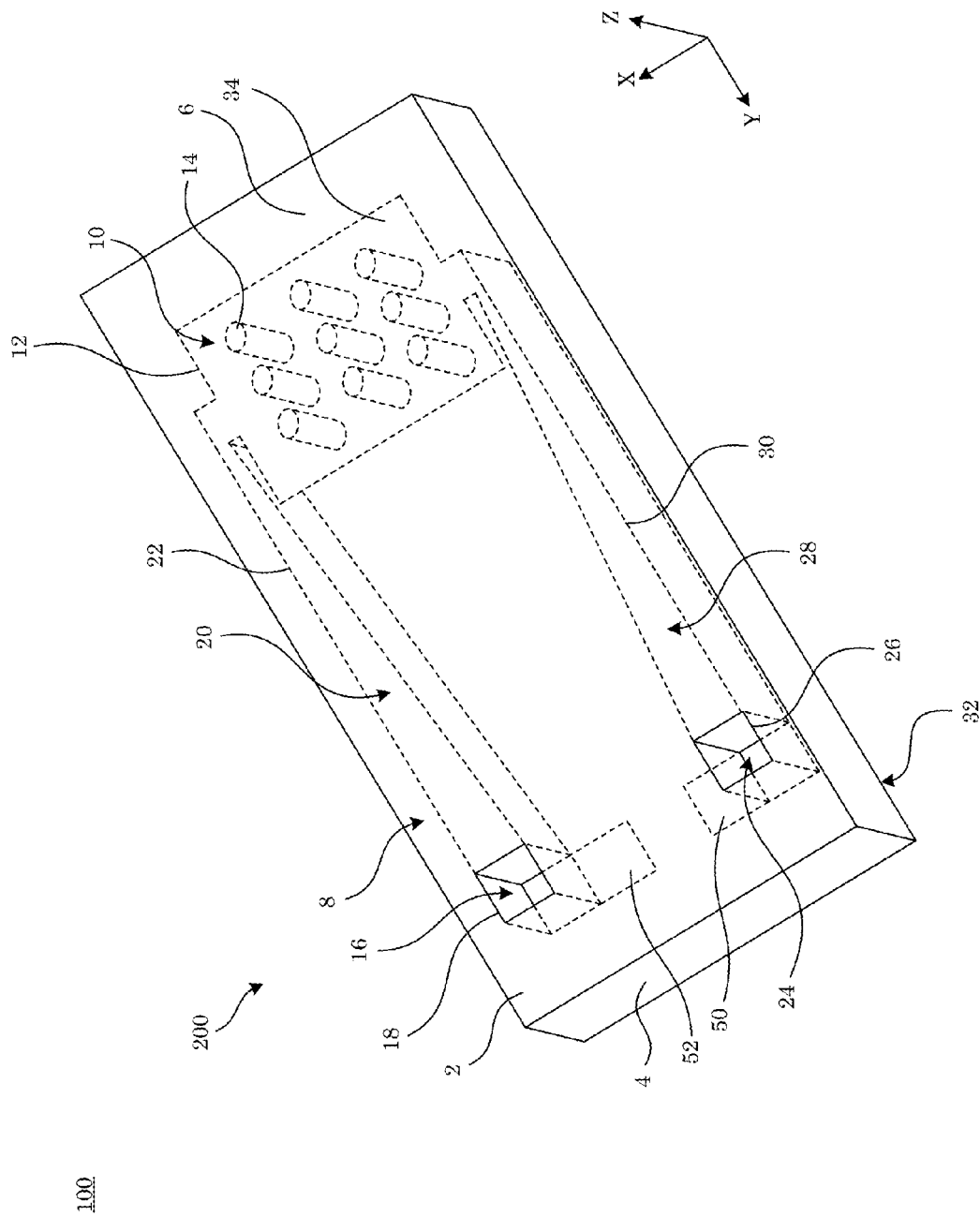
FIG. 8 shows a perspective view of a fluid sampler that includes a sample cell.
Figure 9:
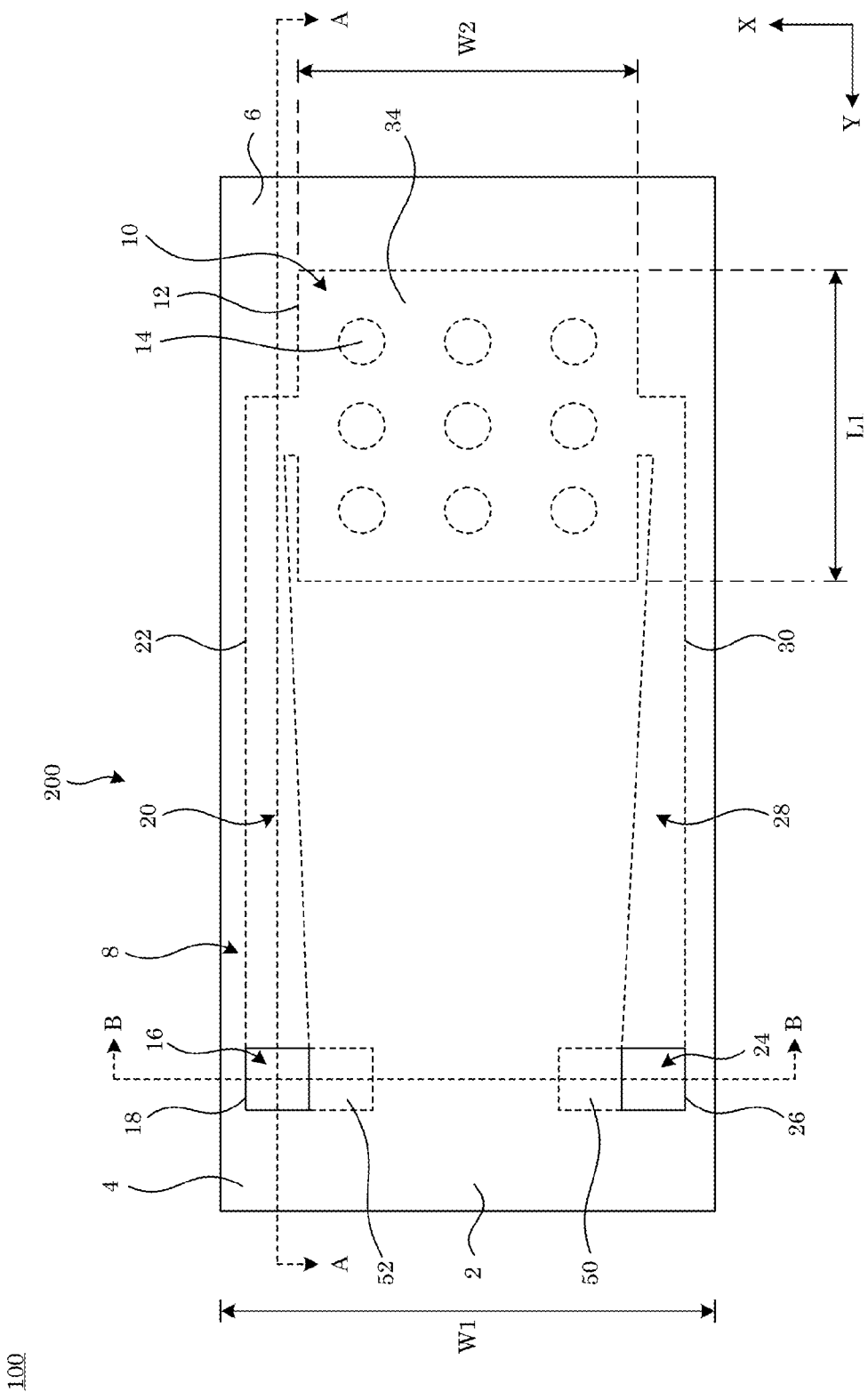
FIG. 9 shows a top view of the fluid sampler shown in FIG. 8.
Figure 10:
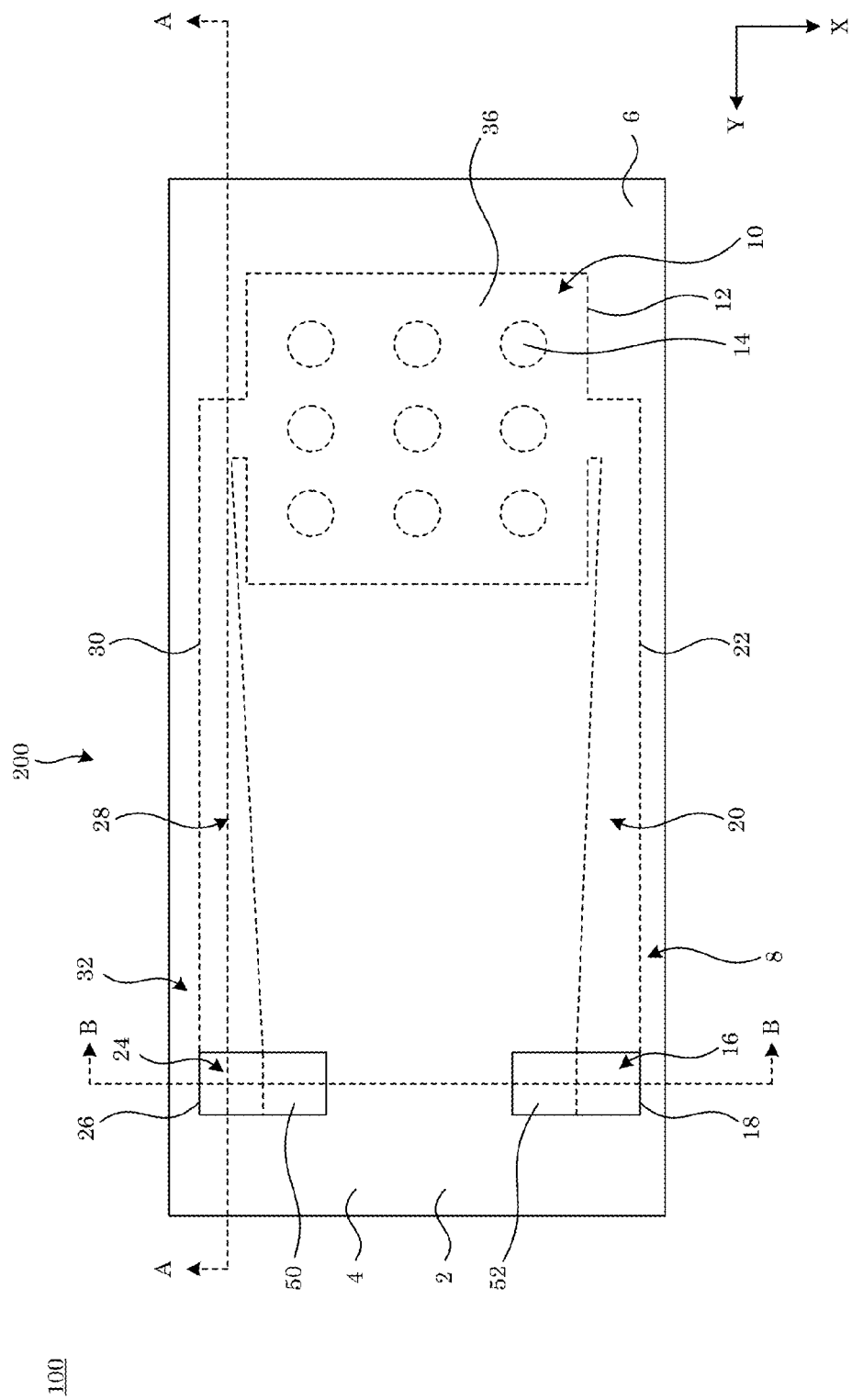
FIG. 10 shows a bottom view of the fluid sampler shown in FIG. 8.
Figure 11:
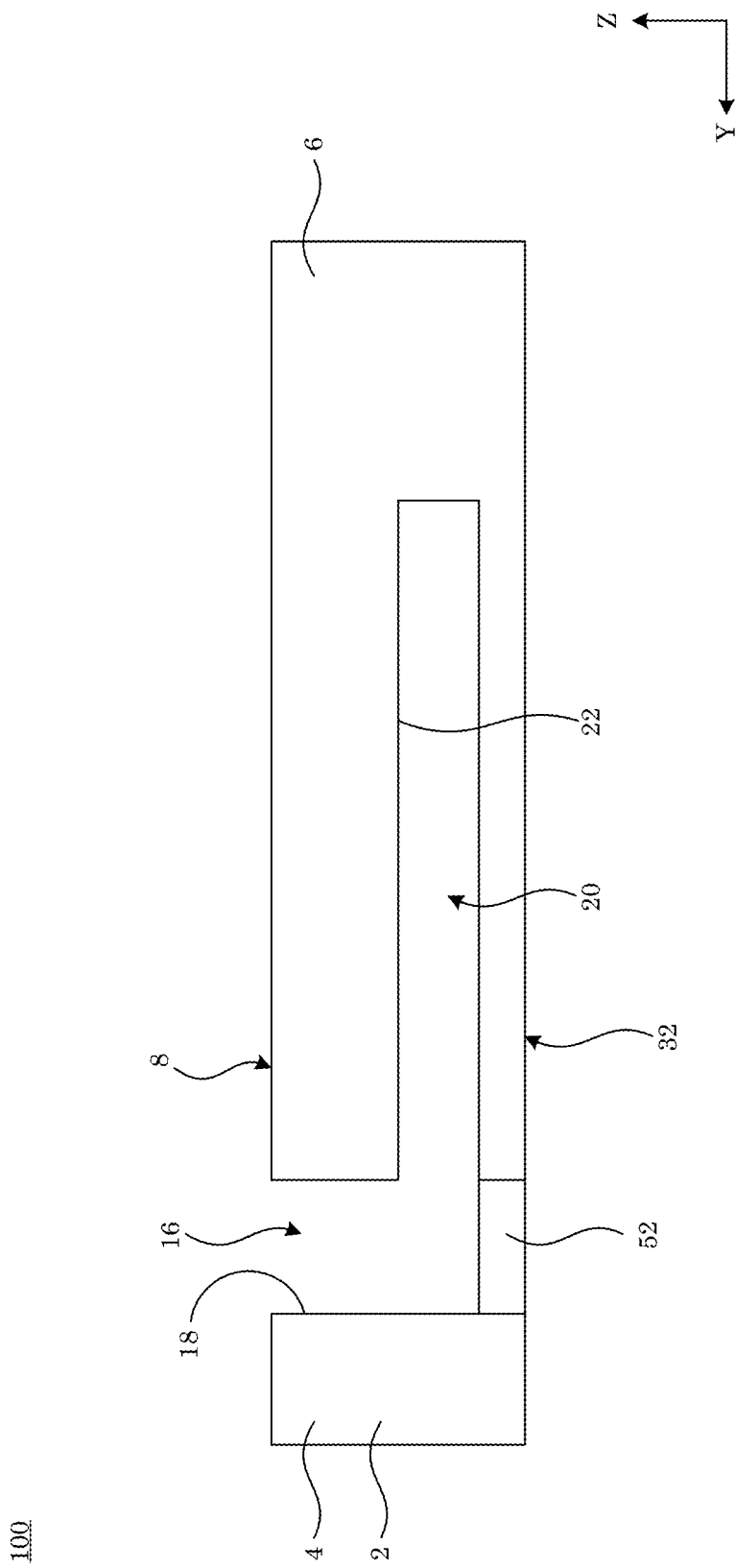
FIG. 11 shows a cross-section along line A-A of the fluid sampler shown in FIG. 9 according to an embodiment.
Figure 12:
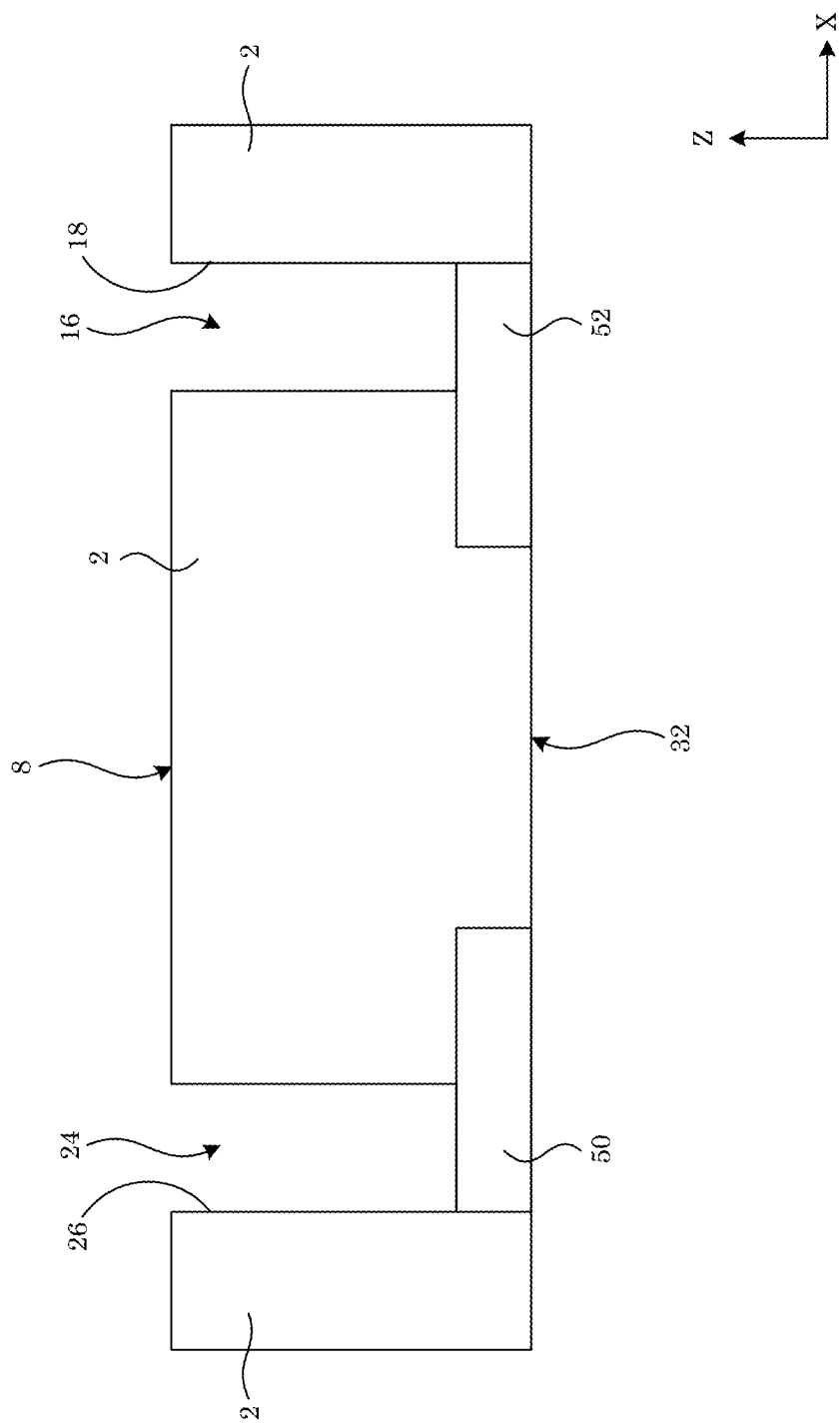
FIG. 12 shows a cross-section along line B-B of the fluid sampler shown in FIG. 9.
Figure 13:
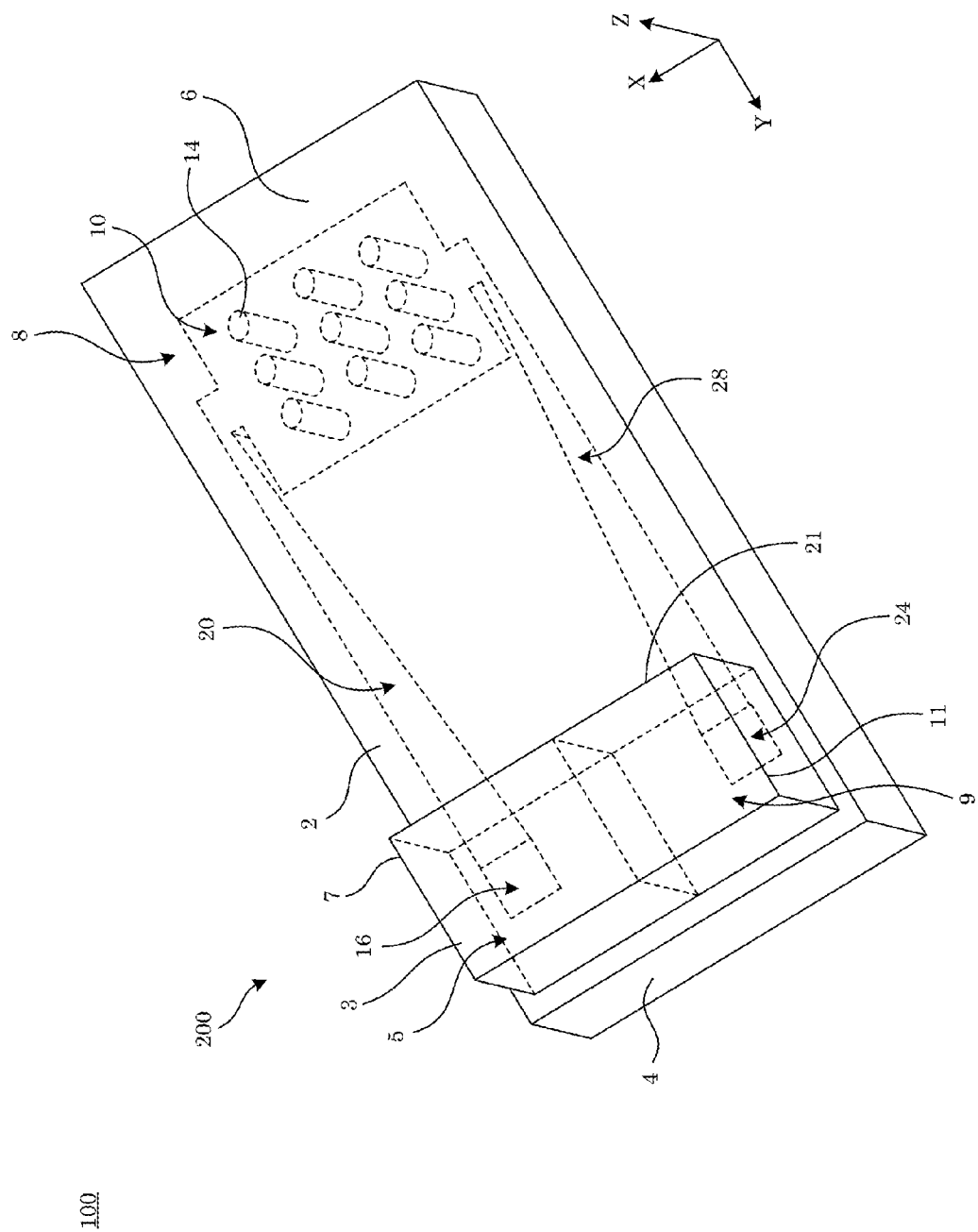
FIG. 13 shows a perspective view of a fluid sampler that includes a sample cell having a fluid reservoir.
Figure 14:
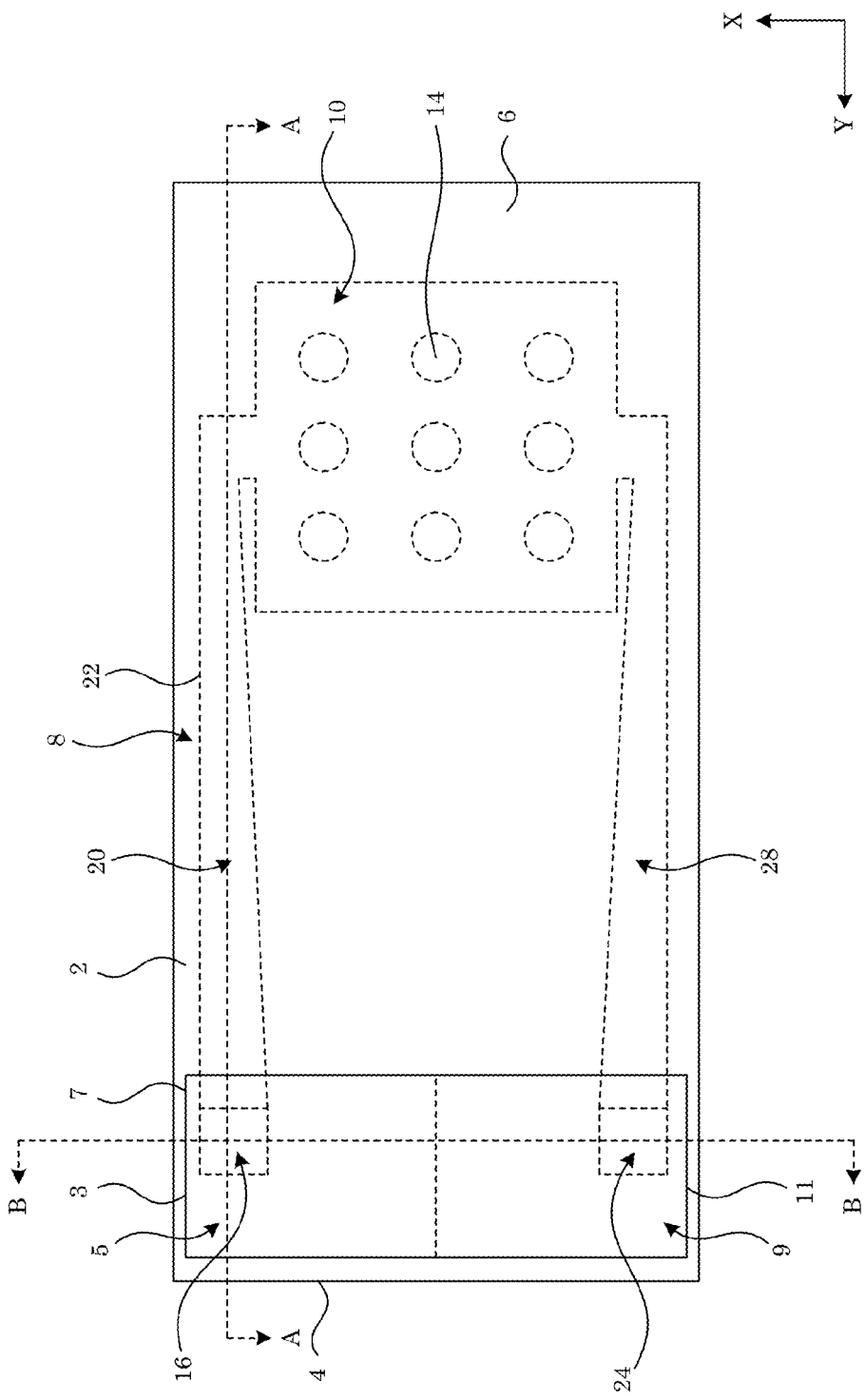
FIG. 14 shows a top view of the fluid sampler shown in FIG. 13.
Figure 15:
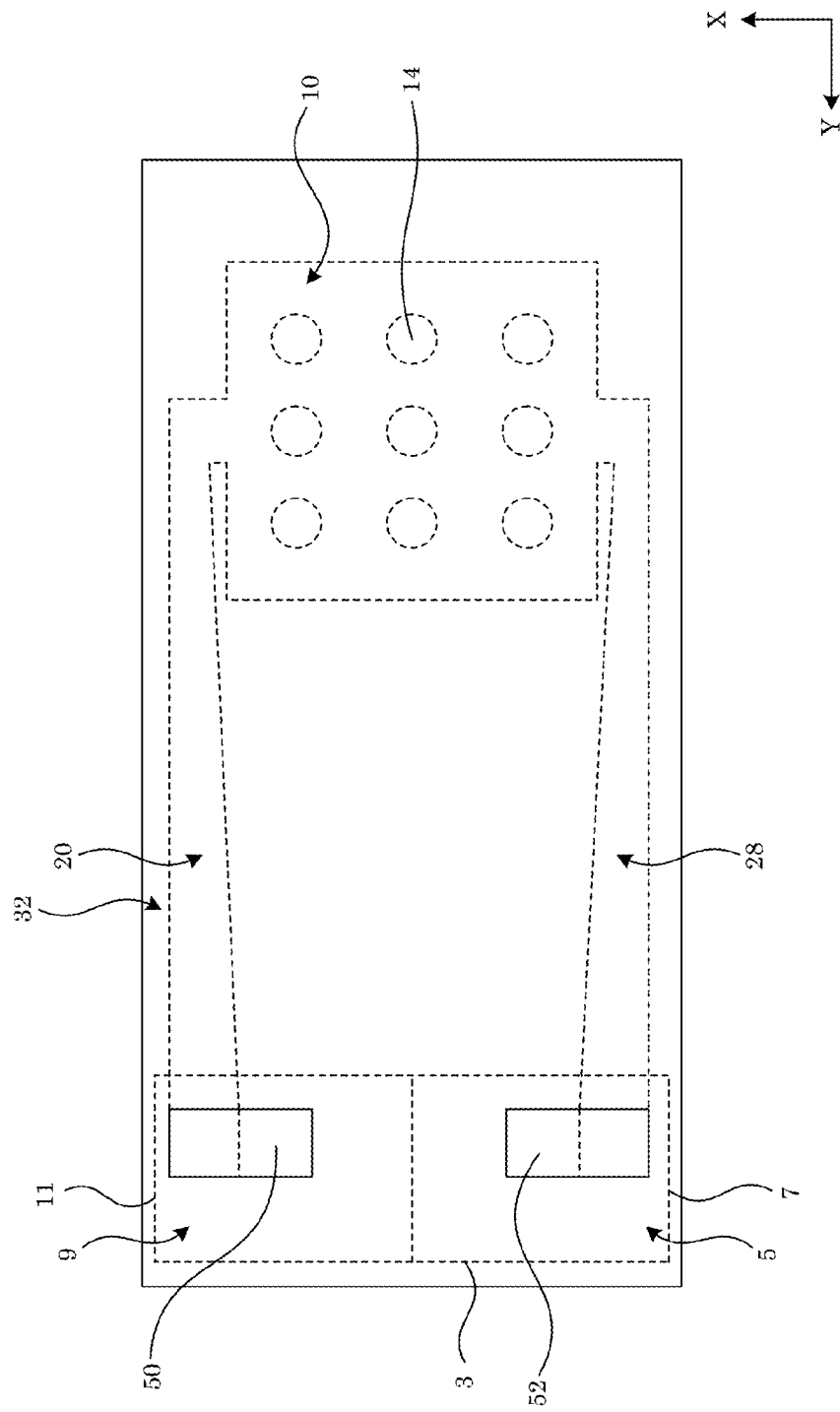
FIG. 15 shows a bottom view of the fluid sampler shown in FIG. 13.
Figure 16:
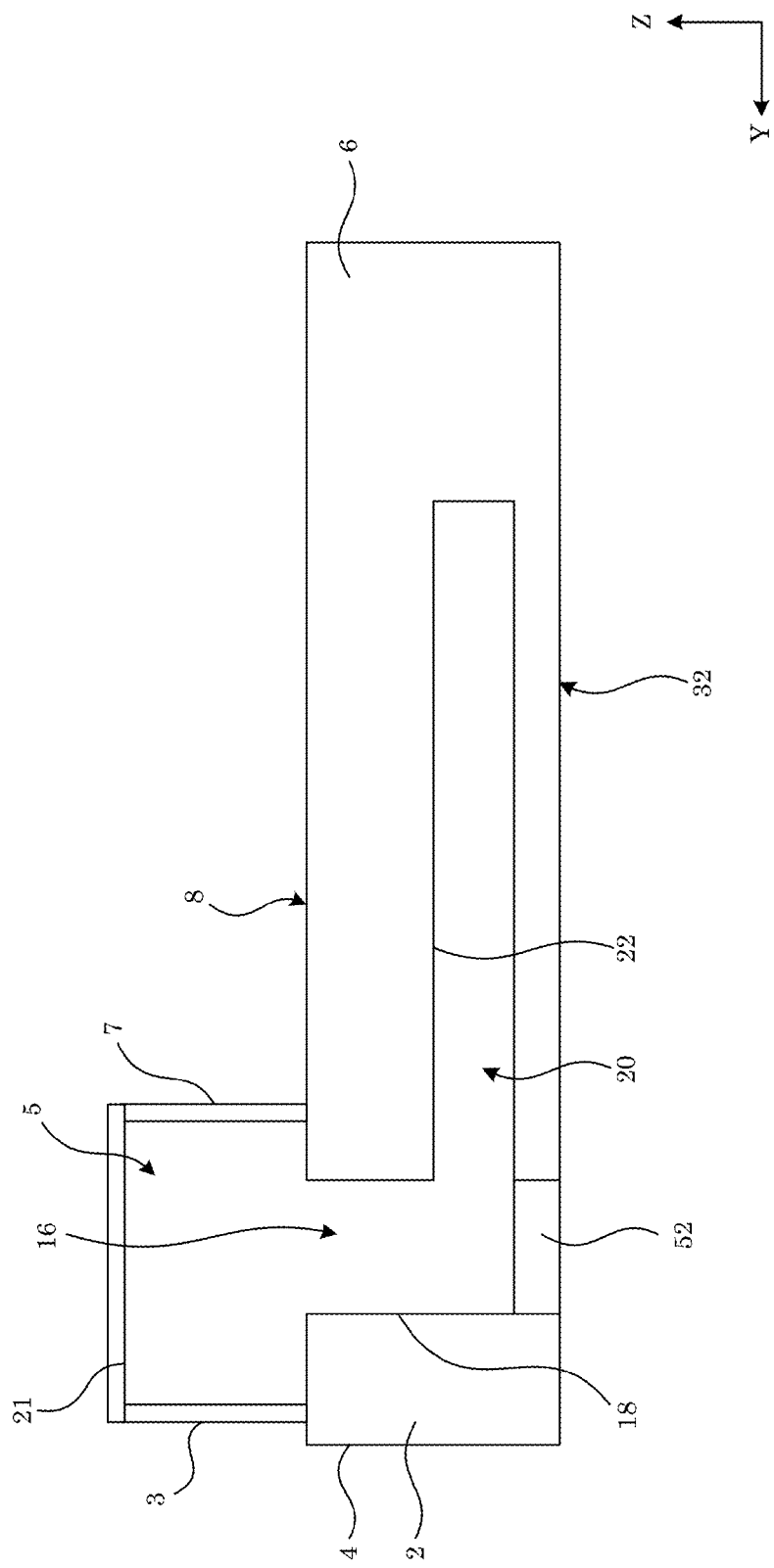
FIG. 16 shows a cross-section along line A-A of the fluid sampler shown in FIG. 14 according to an embodiment.
Figure 17:
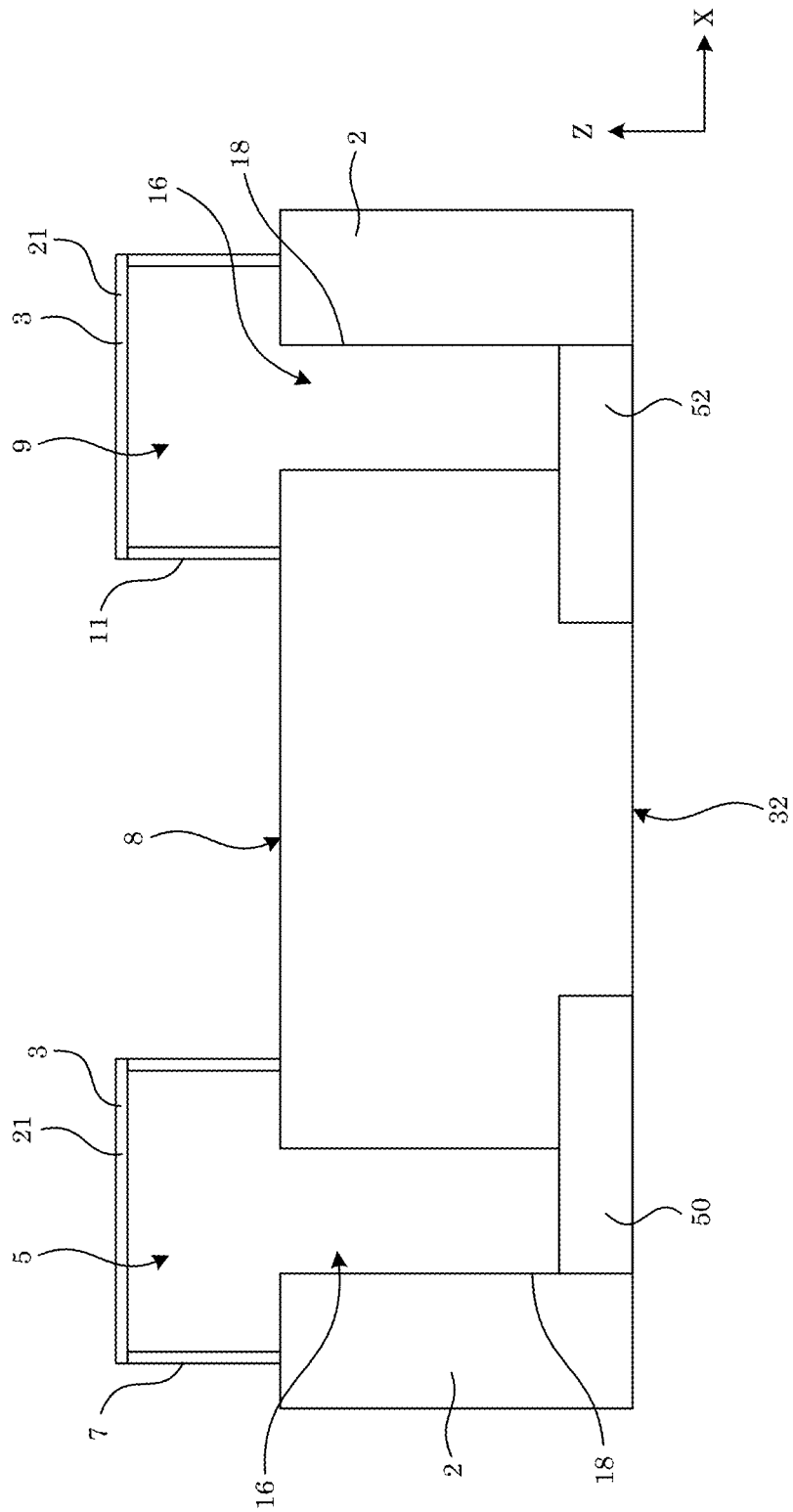
FIG. 17 shows a cross-section along line B-B of the fluid sampler shown in FIG. 14.
Figure 18:
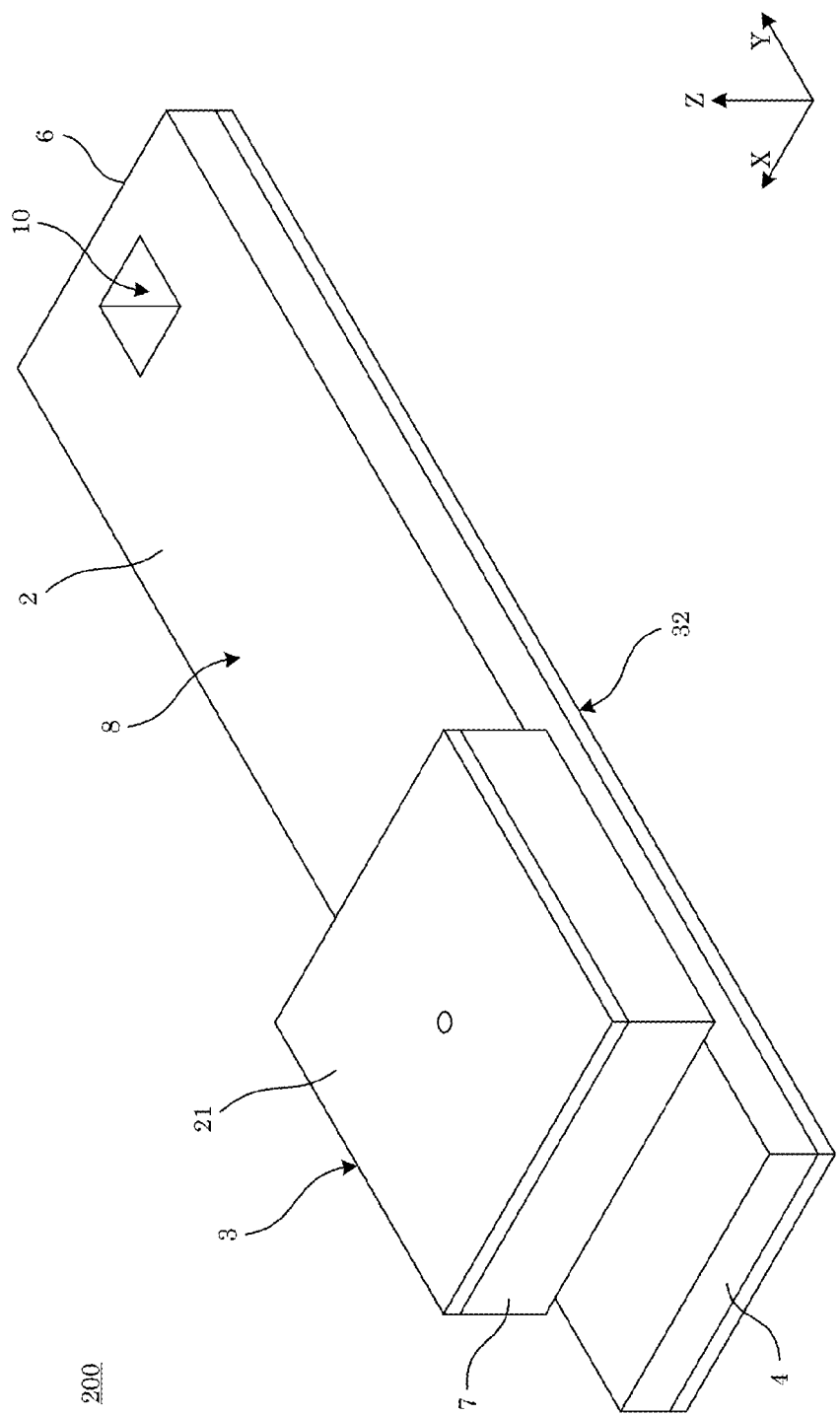
FIG. 18 shows a top perspective view of a fluid sampler that includes a sample cell having a fluid reservoir.
Figure 19:
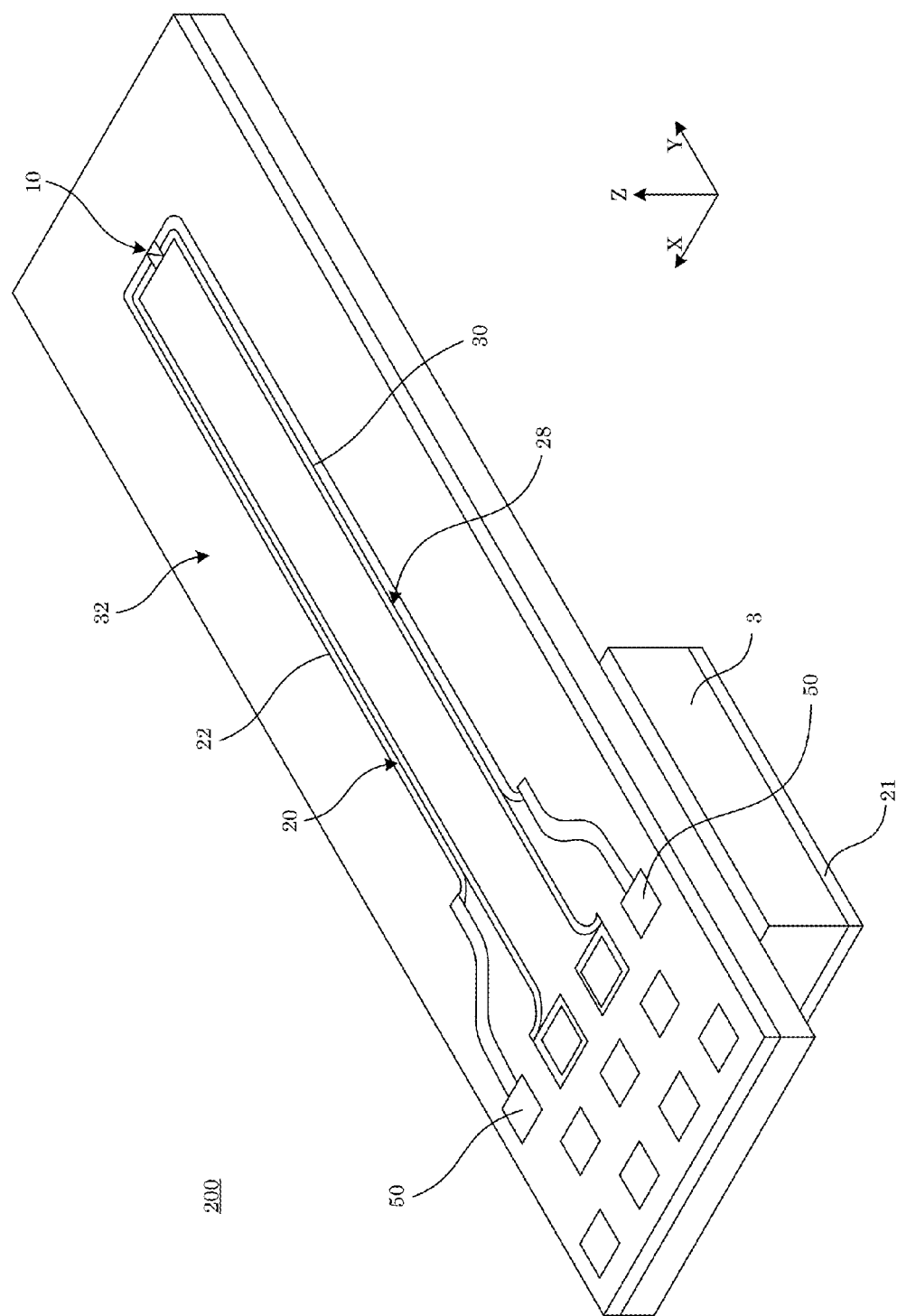
FIG. 19 shows a bottom perspective view of the fluid sampler shown in FIG. 18.
Figure 20:
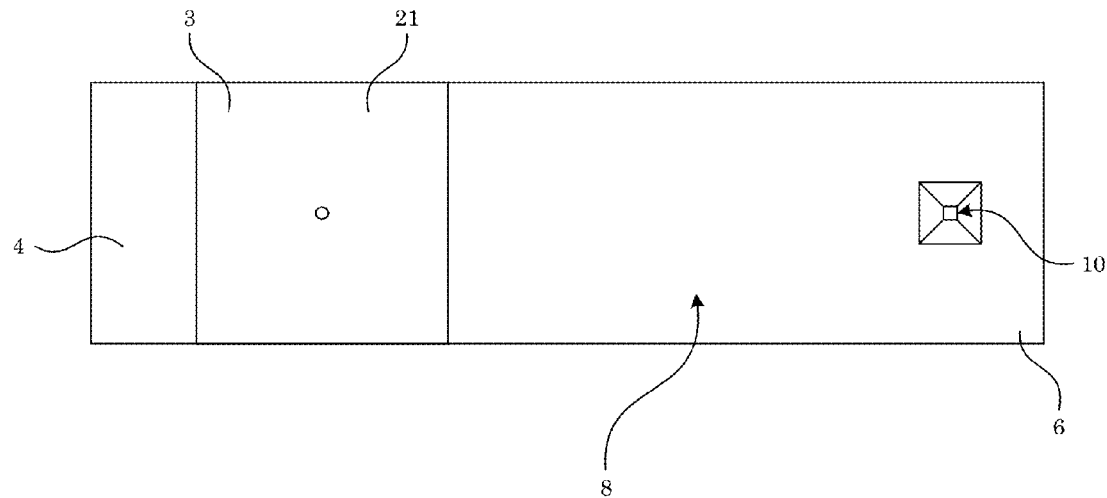
FIG. 20 shows a top view and bottom view of the fluid sampler shown in FIG. 18.
Figure 20:
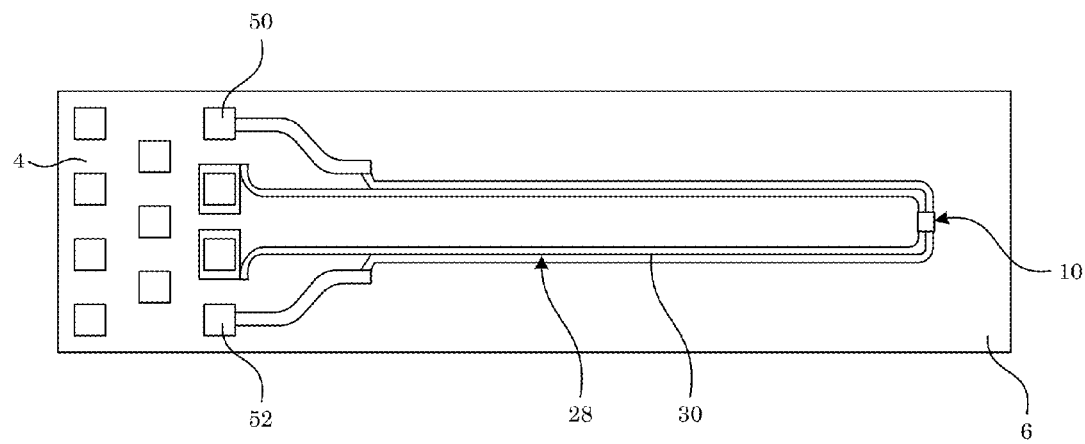
Figure 21:
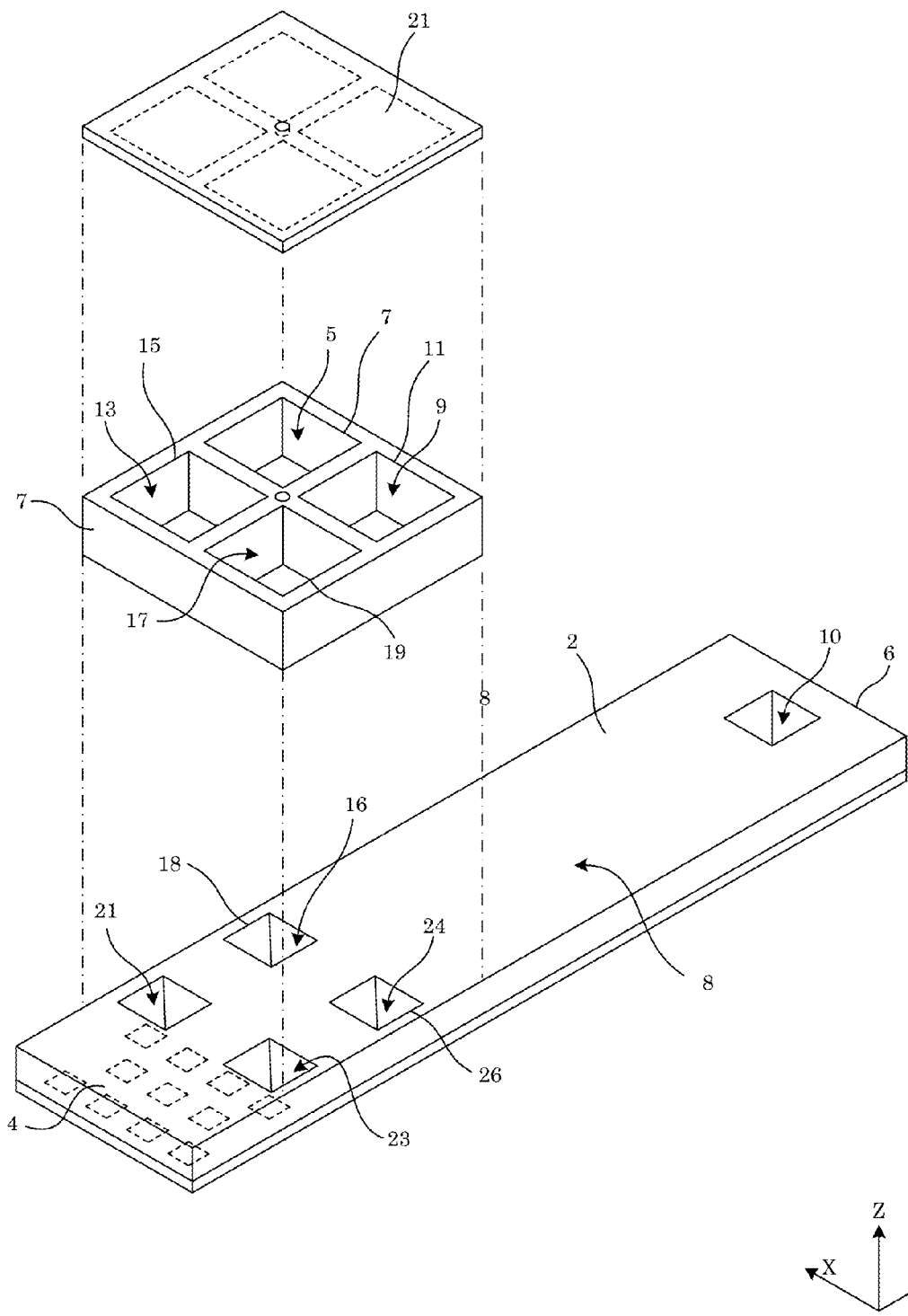
FIG. 21 shows a side views of the fluid sampler shown in FIG. 18 according to an embodiment.
Figure 22:
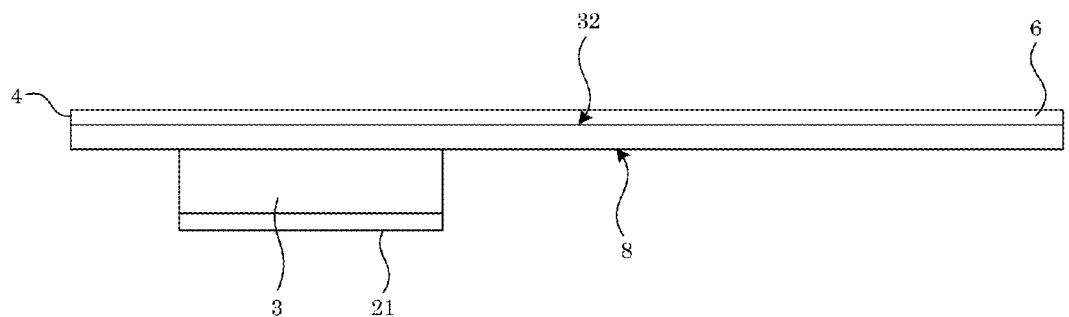
FIG. 22 shows an exploded view of the fluid sampler shown in FIG. 18.
Figure 22:
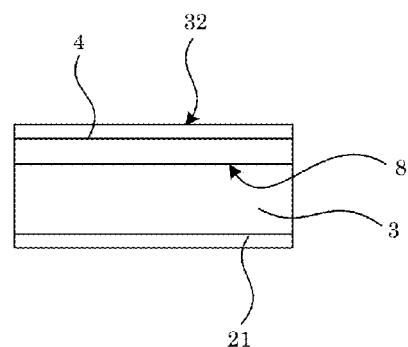

In an embodiment, with reference to FIG. 7 (an exemplary cross-section through line B-B of FIG. 2), a physical geometry (e.g., a contour of a bounding wall 40) of first conduit 20 provides microfluidic flow of fluid from first port 16 and transitions microfluidic flow to nanofluidic flow into viewing reservoir 10. Similarly, a physical geometry of second conduit 28 can provide nanofluidic flow of fluid from viewing reservoir 10 and can transition the nanofluidic flow to microfluidic flow to second port 24. As a result, conduit (20, 24) provide microfluidic flow of the fluid, and viewing reservoir 10 provides nanofluidic flow of the fluid.

According to an embodiment, with reference to FIG. 8, FIG. 9, FIG. 10, FIG. 11, and FIG. 12, sample cell 200 includes first electrode 52 disposed on substrate 2 and in electrical communication with first port 16; and second electrode 50 disposed on substrate 2 and in electrical communication with second port 24. First electrode 52 and second electrode 50 produce an electric field through the fluid disposed in viewing reservoir 10 in response to application of a first electric potential to first electrode 52 and application of a second electric potential to second electrode 50. In this manner, the fluid electrokinetically flows from first port 16 and through viewing reservoir 10 to second port 24 in response to a presence of the electric field.

In an embodiment, with reference to FIG. 13, FIG. 14, FIG. 15, FIG. 16, and FIG. 17, fluid sampler 100 includes fluid container 3 disposed on substrate 2 of sample cell 200. Fluid container 3 can include first fluid reservoir 5 bounded by wall 7 in fluid communication with first port 16 and that stores fluid for communication to first port 16 and communicates fluid with first port 16. Fluid container 3 also can include second fluid reservoir 9 bounded by wall 11 and in fluid communication with second port 24. Here, second fluid reservoir 9 stores fluid for communication with second port 24; and communicates fluid with second port 24. In an embodiment, lid 21 is disposed on fluid reservoir (5, 7, and the like) to contain the fluid on sample cell 200. In an embodiment, lid 21 seals the fluid in fluid container 3 and ports (16, 24) conduits (20, 28) and viewing reservoir 10. Fluid can be introduced in to fluid reservoirs (e.g., 5, 7) such that sample cell 200 can be disposed in a vacuum chamber in an absence of further introduction of fluid into fluid container 3 from an external source. In an embodiment, fluid container 3 can be interfaced to an external fluid source while being disposed, e.g., in a vacuum chamber for fluid communication of the fluid between fluid container 3 and the external fluid source (e.g., see FIG. 23). A number of fluid reservoirs can be selected based on a number of fluid ports (e.g., 16, 24, and the like) disposed on substrate 2. The fluid disposed in the different fluid reservoirs (e.g., 5, 9, and the like) can be the same or can be different.

Electrodes (e.g., 50, 52, and the like) provide electrical connections for heating, temperature sensing, moving components, electrical biasing, and the like of sample cell 200.

In an embodiment, with reference to FIG. 18, FIG. 19, FIG. 20, FIG. 21, FIG. 22, sample cell 200 can include a plurality of fluid ports (16, 24, 21, 23) in fluid communication with viewing reservoir 10; a plurality of pillars 14 disposed in viewing reservoir 10 and interposed between first view membrane 34 and second view membrane 36; plurality of conduits (20, 28) that communicates fluid from the plurality of fluid ports (16, 24, 21, 23) and viewing reservoir 10; a plurality of electrodes (50, 52) in electrical communication with and exposed to fluid ports (16, 24, 21, 23); and flow container 3 disposed on substrate 2 and including a plurality of fluid reservoirs (5, 9, 13, 17) that are in fluid communication with fluid ports (16, 24, 23, 21), wherein led 21 is disposed on fluid reservoirs (5, 9, 13, 17) to seal the fluid in sample cell 200. Although flow container 3 is shown as disposed on first surface 8, and electrodes (50, 52) are disposed on second surface 32, it is contemplated that any permutation of the locations and arrangements of fluid container 3 and electrodes (50, 52) can be provided on substrate 2.

Figure 23:
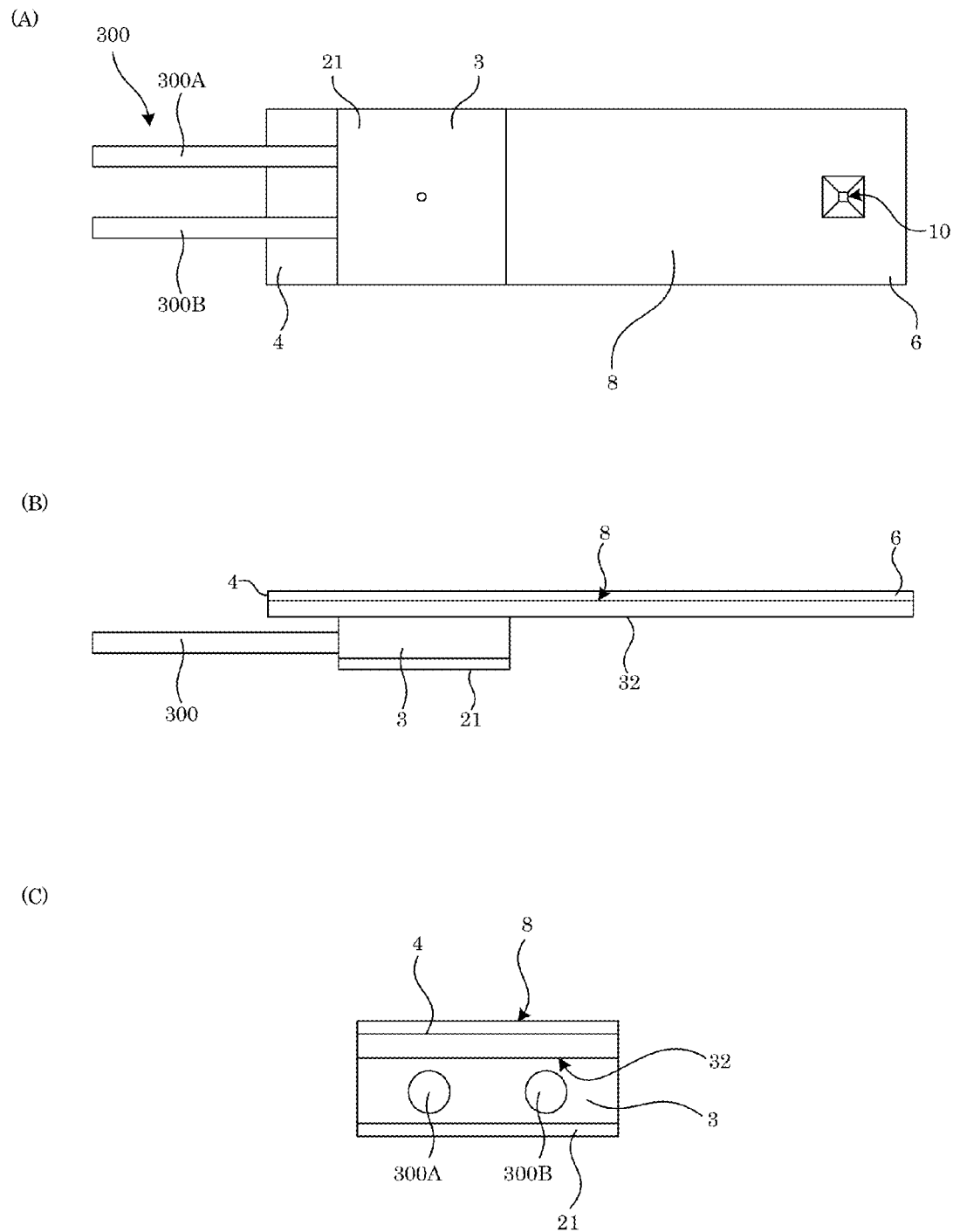
FIG. 23 shows a perspective view of a fluid sampler that includes a sample cell and fluid line.

In an embodiment, with reference to FIG. 23, fluid sampler 100 can include fluid line 300 connected to fluid container 3. Fluid line 300 communicates fluid with fluid reservoir (e.g., 5, 9, and the like). A number of fluid lines 300 can be selected based on a number of fluid reservoirs disposed in fluid container 3. In an embodiment, fluid sampler 100 includes: first gas line 300A in fluid communication with first fluid reservoir 5 and that supplies the fluid to first reservoir 5; and second gas line 300B in fluid communication with second fluid reservoir 9 and that receives the fluid from second reservoir 9, such that the fluid flows from first fluid line 300A to first fluid reservoir 5, from first fluid reservoir 5 to viewing reservoir 10, from viewing reservoir 10 to second port 24, and from second port 24 to second fluid line 300B.

Figure 24:
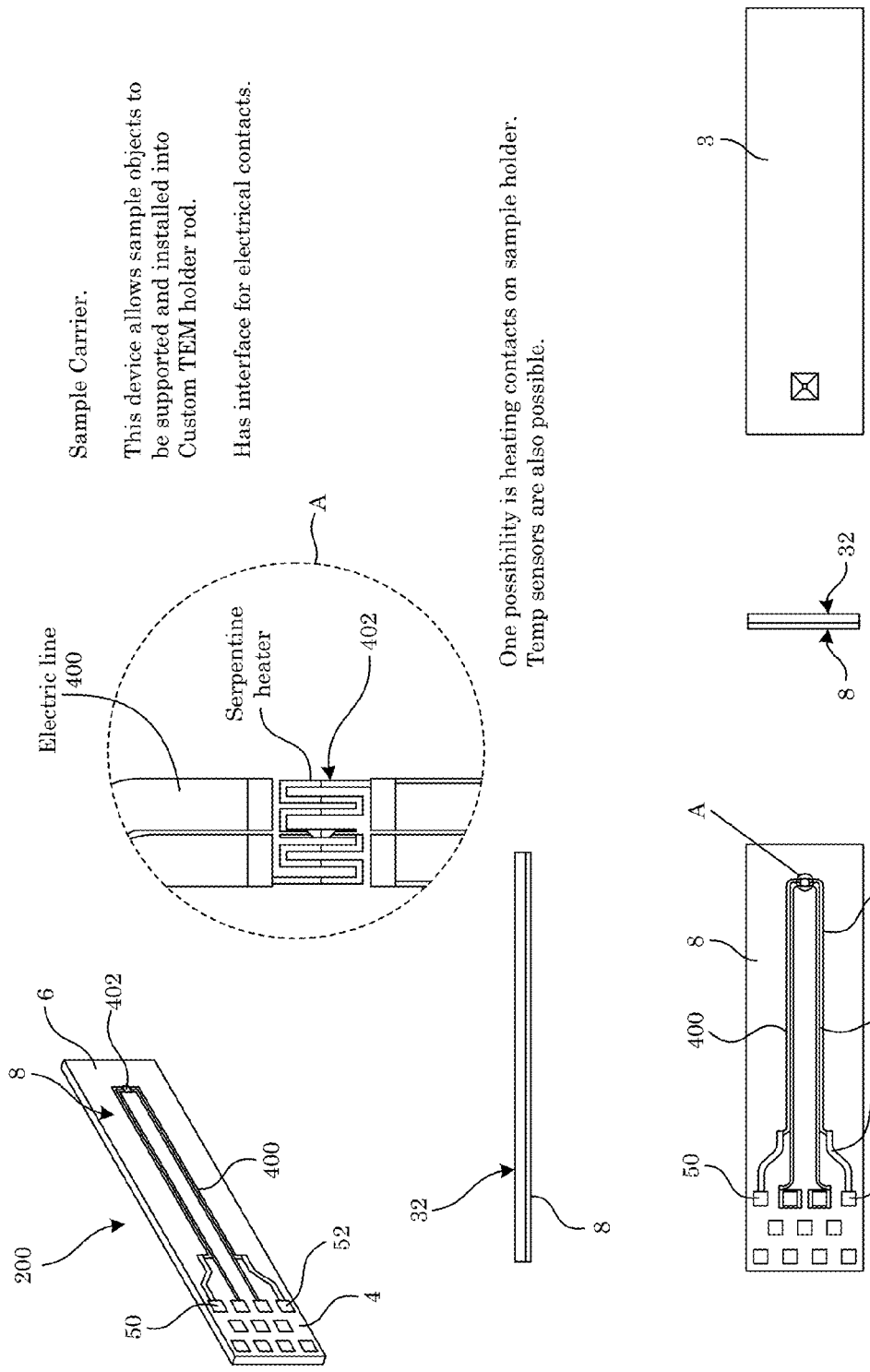
FIG. 24 shows a perspective view of a fluid sampler that includes a sample cell and fluid line.
Figure 25:
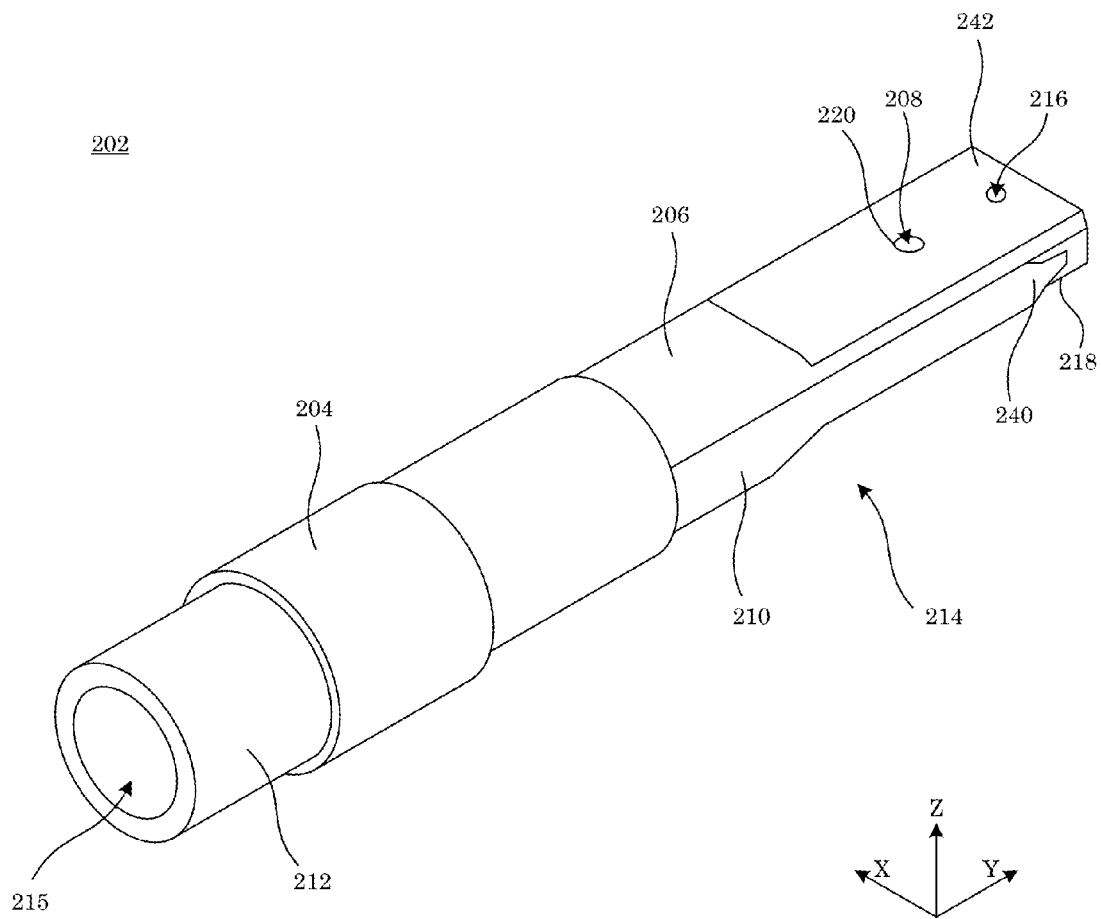
FIG. 25 shows a perspective view of a holder.
Figure 26:
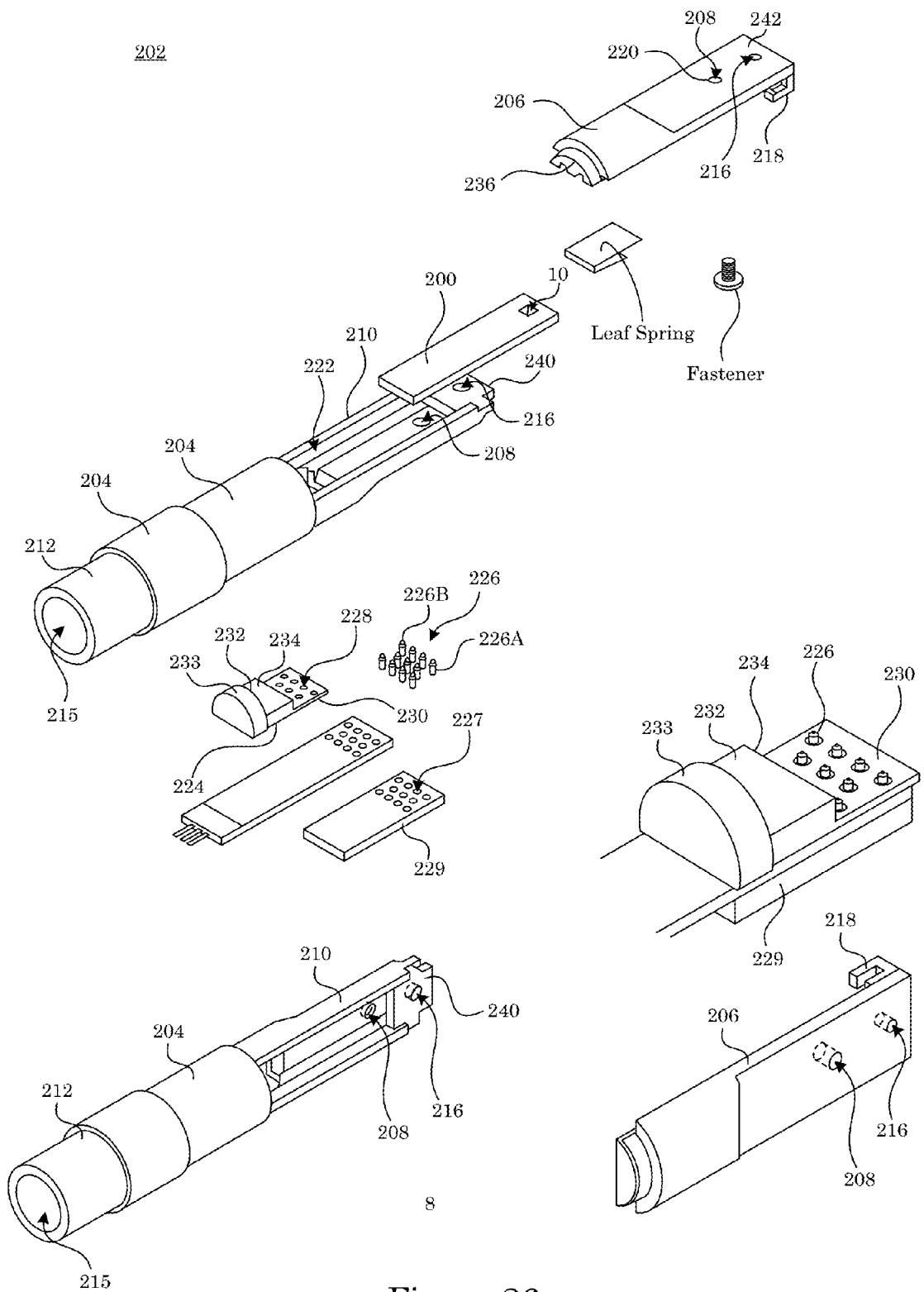
FIG. 26 shows an exploded view of the holder and components shown in FIG. 25.
Figure 27:
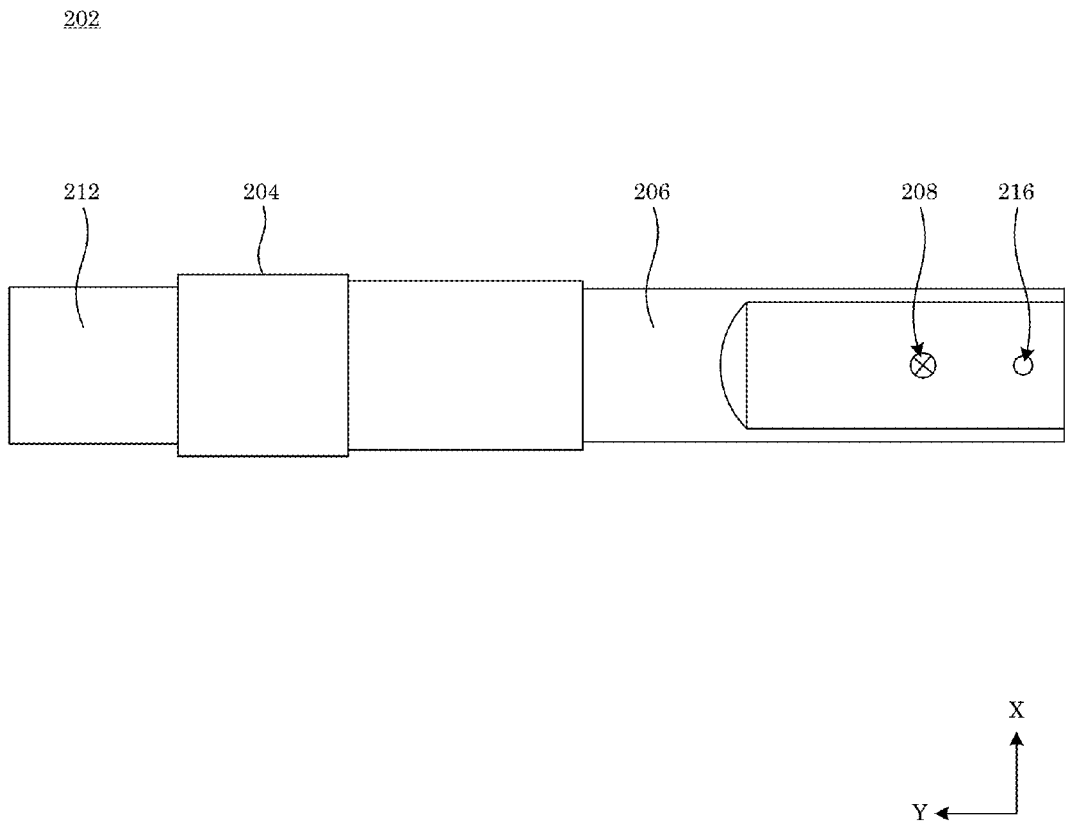
FIG. 27 shows a top view of the holder shown in FIG. 25.
Figure 28:
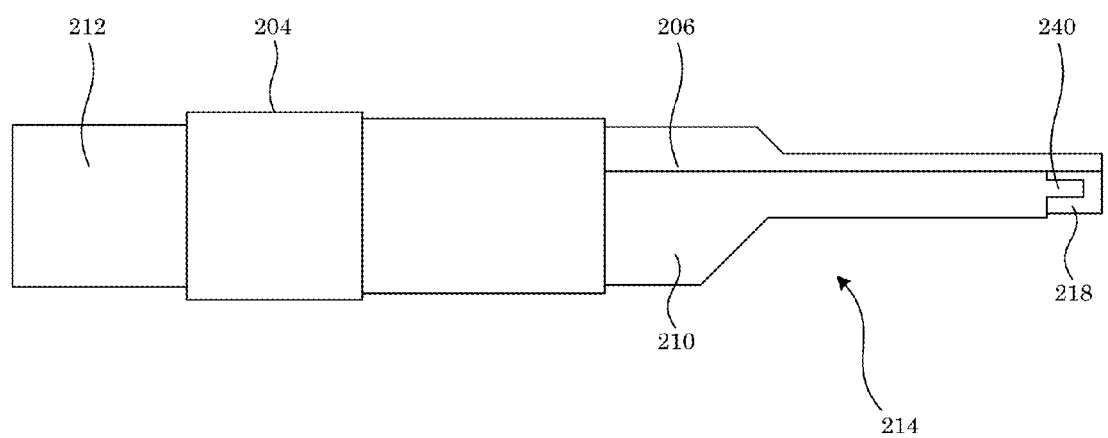
FIG. 28 shows a side view of the holder shown in FIG. 25.
Figure 29:
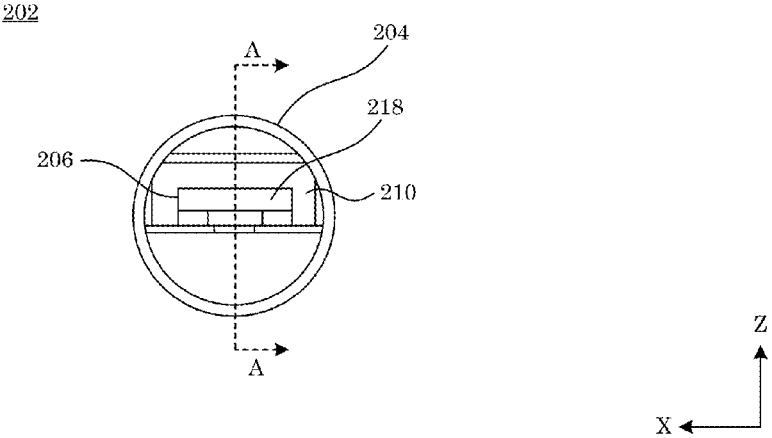
FIG. 29 shows a cross-section along line A-A of the holder shown in FIG. 27.
Figure 29:
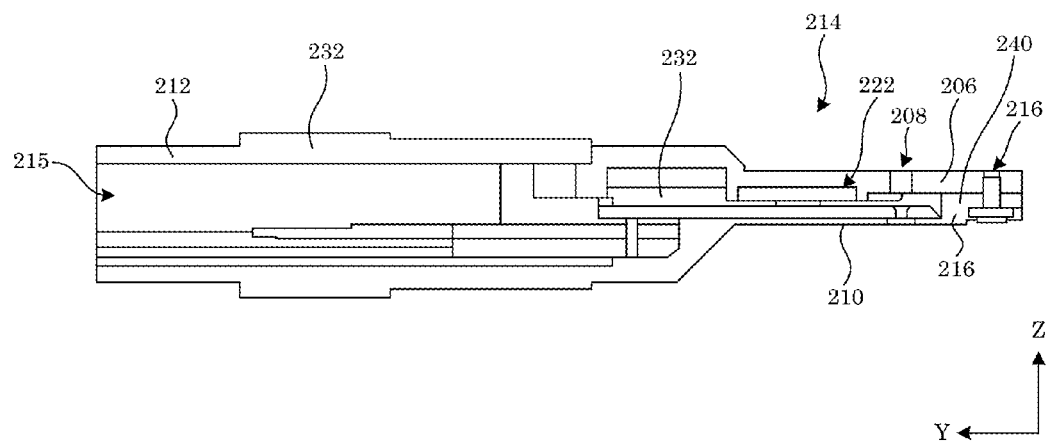

In an embodiment, with reference to FIG. 24, sample cell 200 includes electrical lines 400 in communication with electrodes (50, 52, and the like) and heater 402 disposed at second end 6. A sample, e.g., a solid sample can be disposed on heater 402 and probed by a probe beam (e.g., electron beam, laser beam, and the like. Heater 402 can heat sample cell 200 and the sample disposed thereon.

In an embodiment, with reference to FIG. 25, FIG. 26, FIG. 27, FIG. 28, FIG. 29, fluid sampler 100 includes holder 202 in which sample cell 200 is disposed. Holder 202 includes transmission aperture 208 bounded by wall 220 and arranged to be transmissively coincident with viewing reservoir 10 of sample cell 200 such that a probe beam (e.g., an electron beam, laser beam, neutron beam, X-ray beam, and the like) subjected to fluid sampler 100 is transmitted tandemly through transmission aperture 208 and viewing reservoir 10. Additionally, holder 202 includes a plurality of electrical contactors 226 disposed in electrode member 224. In an embodiment, sample cell 200 includes first electrode 52 in electrical communication with first port 16; and second electrode 50 in electrical communication with second port 24, and holder 200 to includes electrode member 224 that includes: first electrical contactor 226A (e.g., a pogo pin) in electrical communication with first electrode 52 through mechanical engagement with first electrode 52; and second electrical contactor 226B (e.g., a pogo pin) in electrical communication with second electrode 50 through mechanical engagement with second electrode 50. Here, first electrode 52 and second electrode 50 can produce an electric field in response to application of a first electric potential to first electrode 52 from first electrical contactor 226A and application of a second electric potential to second electrode 50 from second electrical contactor 226B. In this manner, the fluid electrokinetically flows from first port 16 and through viewing reservoir 10 to second port 24 in response to presence of the electric field.

Figure 30:
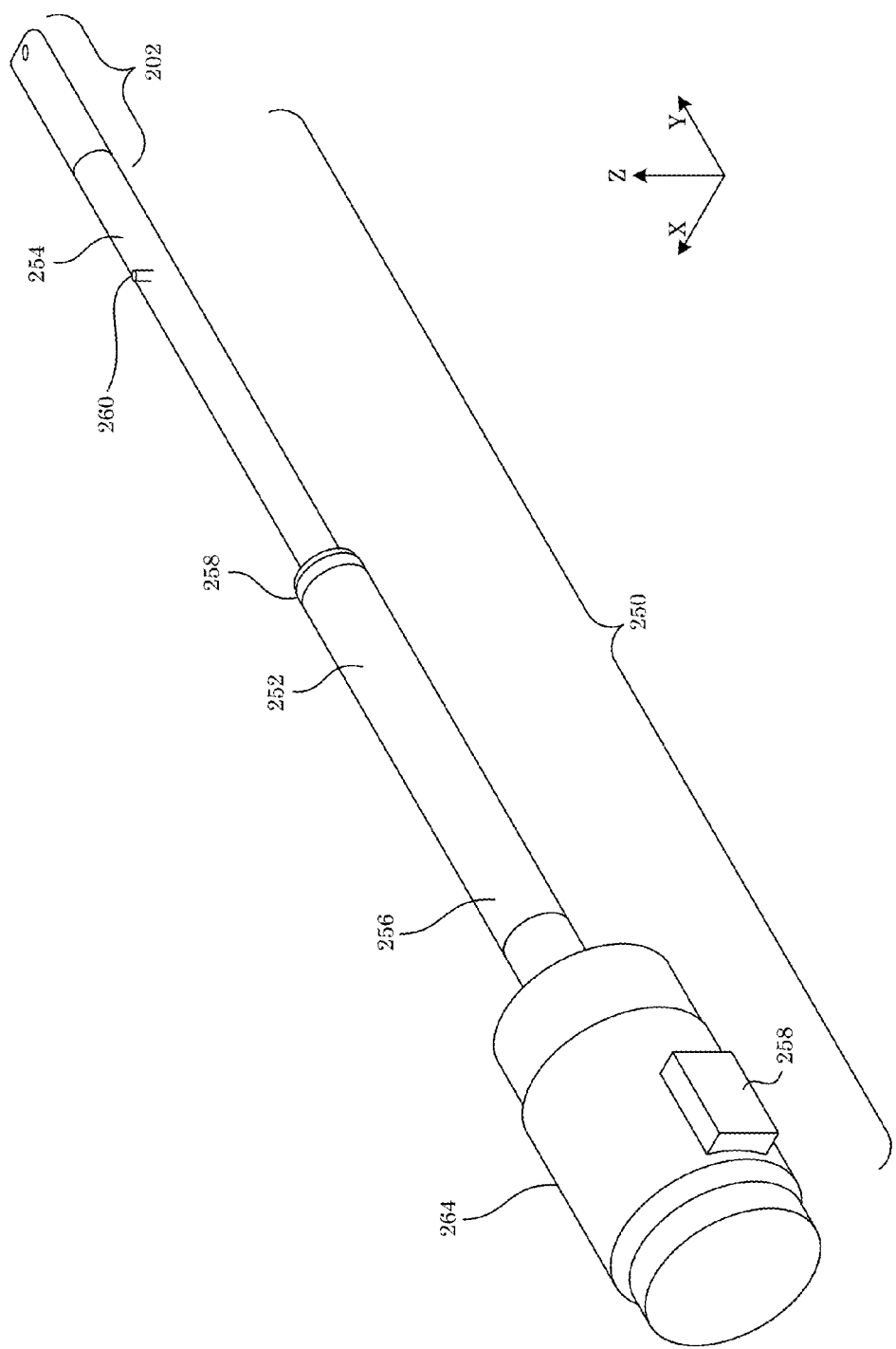
FIG. 30 shows a perspective view of a transfer arm.
Figure 31:
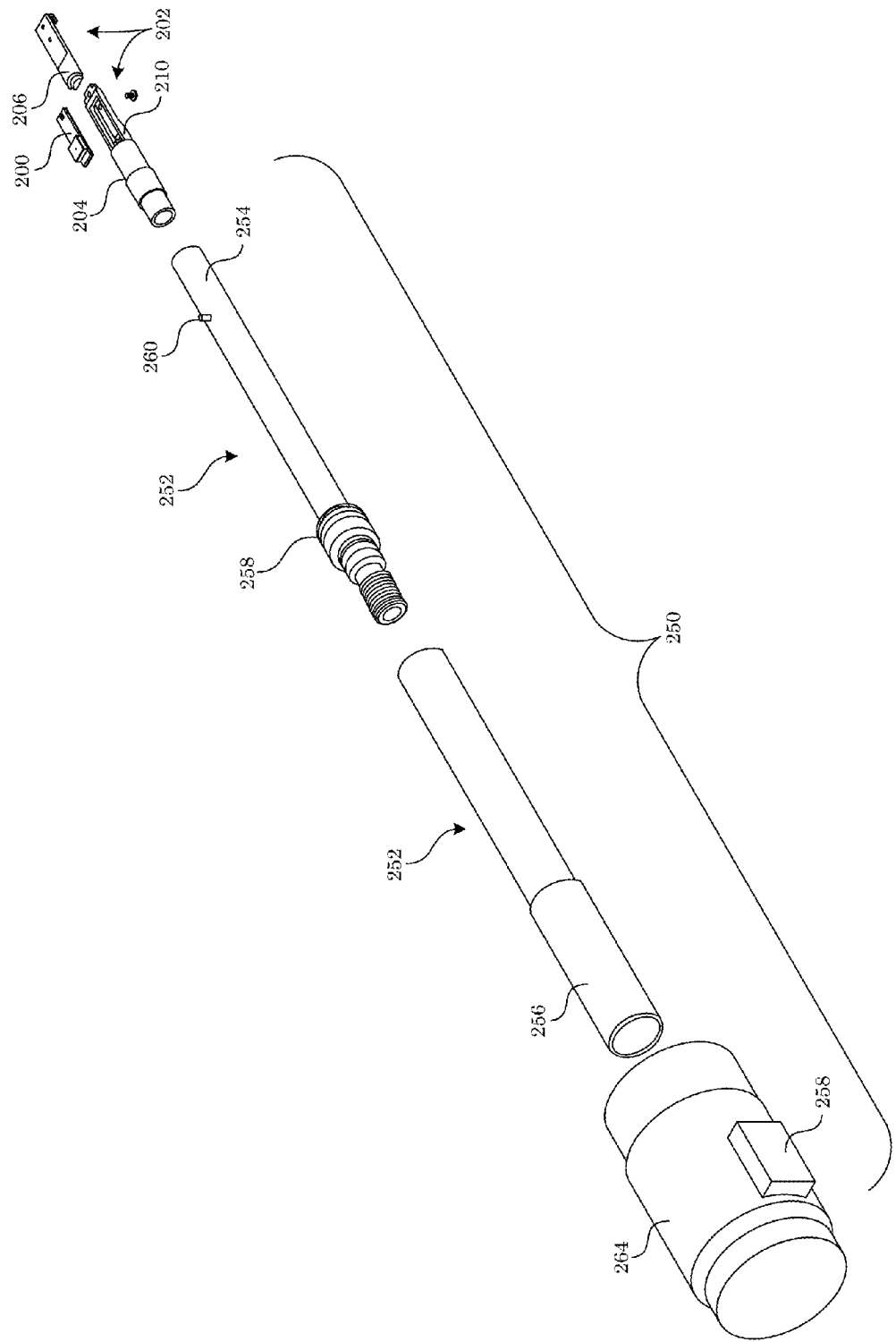
FIG. 31 shows an exploded view of the transfer arm shown in FIG. 30.
Figure 32:
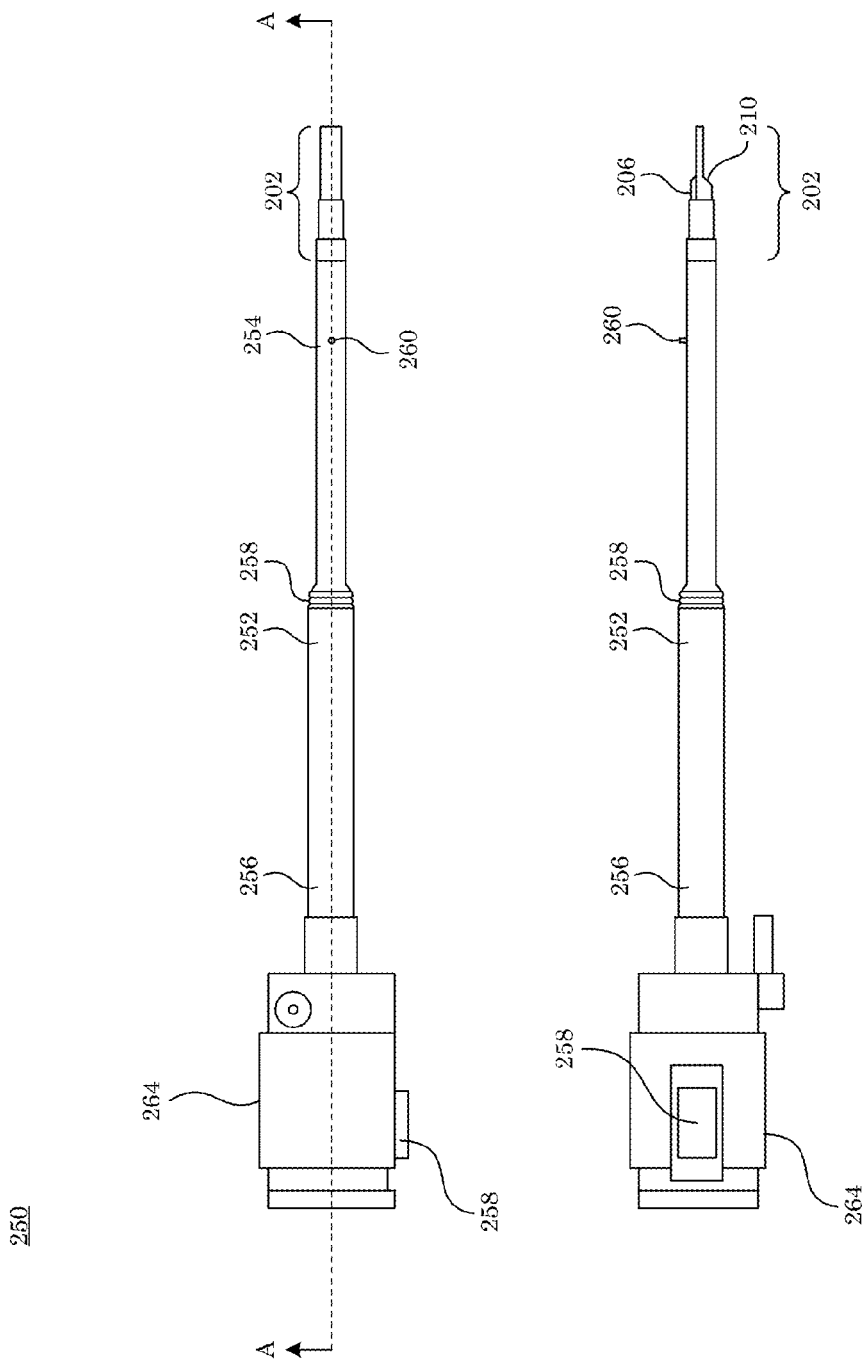
FIG. 32 shows a top view of the transfer arm shown in FIG. 30.
Figure 33:
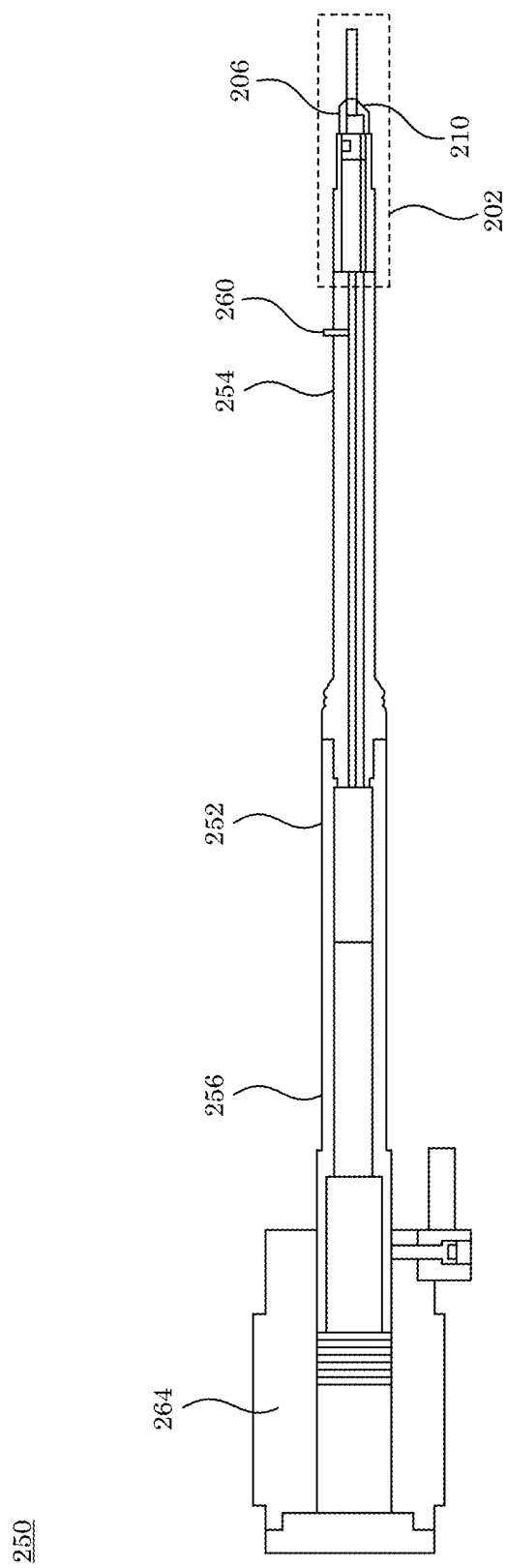
FIG. 33 shows a cross-section along line A-A of the transfer arm shown in FIG. 32.

Holder 202 can include lidded compartment 214 in which sample cell 200 and electrode member 224 are disposed. Lidded compartment 214 includes lid 210; lid 206 disposed on and in mechanical contact with lid 210; and armature receiver 212 disposed on lidded compartment 214 and that receives transfer arm 250 (see, e.g., FIG. 30). Lid 206 and lid 210 bound internal compartment 222 in which sample cell 200 is disposed. Lid 206 of lidded compartment 214 can include transmission aperture 208 to transmit the probe beam there is through to viewing reservoir 10 of sample cell 200; fastener hole 216 to receive a fastener (e.g., a screw); prong the 236 disposed at and projecting from a first end of lid 206 to mechanically engage body 204; and hook 218 disposed at a second end of lid 206, wherein hook 218 mechanically engages lid 210 by inserting tab 240 of lid 210 between hook 218 and hook 218 of lid 206. Additionally, lid 206 can include a spring member (e.g., a leaf spring) to mechanically engage first surface 8 of sample cell 200 and to impart a force on sample cell 200 so that electrodes (50, 52) of sample cell 200 are pressed against electrical contactors 226 of electrode member 224.

Lid 210 can include transmission aperture 208 to be transmissively coincident with transmission aperture 208 of lid 206; and tab 240 to mechanically engage with hook 218 of lid 206. Body 204 receives electrode member 224. Electrode member 224 includes electrical contactors 226 disposed in electrode receivers 228 that are disposed on platform 230. Platform 230 can be offset from platform 232 at step edge 234. Step edge 234 can engage first end 4 of sample cell 200. Electrical contactors 226 received in electrode receivers 228 of platform 230 can be held there in by electrode stay 226. Electrode stay 226 can be connected to (e.g., adhered, fastened, and the like) to electro member 224 and can include aperture is 227 to receive a portion of electrical contactors 226. Further, Armature receiver 212 can include receptacle 214 that receives transfer arm 250. It is contemplated that receptacle 214 can include a feature (e.g., threading, slot, groove, alignment pin, and the like) that engages with transfer arm 250.

It is contemplated that holder 202 receives elements (e.g., electrical wiring, fluid line 300, and the like) to interface with sample cell 200. In this manner, sample cell 200 communicates with external sources (e.g., an electrical source, fluid source, and the like). Moreover, holder 202 provides an off-set or non-symmetric placement of sample cell 200 disposed in holder 202 with respect to transfer arm 250 and provide a space between pole pieces in a TEM so that space is available below sample holder 202 to allow other diagnostic tools to be installed in a TEM vacuum chamber. Lidded compartment 214 provides engagement of tab 240 with hook 218 so that sample cell 200 maintains alignment while lids (210, 206) are installed. Lidded compartment 214 can include a leaf spring for a force to maintain a position of sample cell 200 in internal compartment 222 and during probing of fluid in viewing reservoir 10 of sample cell 200. The interlocking design allows for the installation of a locking screw to secure the lid without the risk of sample misalignment. Since clamping and interlocking of lid (206, 210) is offset from a centerline of transfer arm 250, a central region of transfer arm 250 provides communication of electrical wire and fluid lines and being vacuum tight and compatible.

In an embodiment, with reference to FIG. 30, FIG. 31, FIG. 32, and FIG. 33, fluid sampler 100 includes transfer arm 250 on which holder 202 is disposed. Transfer arm 250 includes armature 252 including: first armature end 254 that is received by armature receiver 212 of holder 202; second armature end 256 that is arranged opposite first armature end 254 and distal to armature receiver 212; electrical feedthrough 258 disposed at second armature end 256; and gasket receiver 258 that receives a gasket (e.g., an O-ring) for producing a vacuum seal in combination with a vacuum chamber. Transfer arm 250 also can include alignment pin 260 disposed on armature 252, handle 264 disposed at second armature end 256, and the like. According to an embodiment, transfer arm 250 further includes: a plurality of wires 262 in electrical communication with electrical feedthrough 258. Wire 262 can include a first wire to communicate the first electric potential from electrical feedthrough 258 to first electrical contactor 226A of holder 202; and a second wire to communicate the second electric potential from electrical feedthrough 258 to second electrical contactor 226B. A number of wires 262 can be selected based on a number of electrical contactors 226 or electrodes (e.g., 50, 52). Electrical wires 262 can be independent components or can be coupled together as a group, e.g., in a printed flexible cable, a printed circuit board, a coaxial cable, and the like. It is contemplated that transfer arm 250 can include a radiation shield disposed therein. The radiation shield can include a material (e.g., a metal or alloy that includes an element with a high atomic number such as 82) that blocks certain radiation (e.g., X-rays) from propagating from sample cell 200 to second armature end 256. The radiation shield can be a foil, block, and the like.

Transfer arm 250 can be monolithic or a plurality of parts and have a length selected for inserting sample cell 200 into a vacuum chamber while handle 264 extends external to the vacuum chamber. Moreover, first Armature end 254 of transfer arm 250 can include a threaded portion to mechanically engage with receptacle 214 of holder 202.

Figure 2:
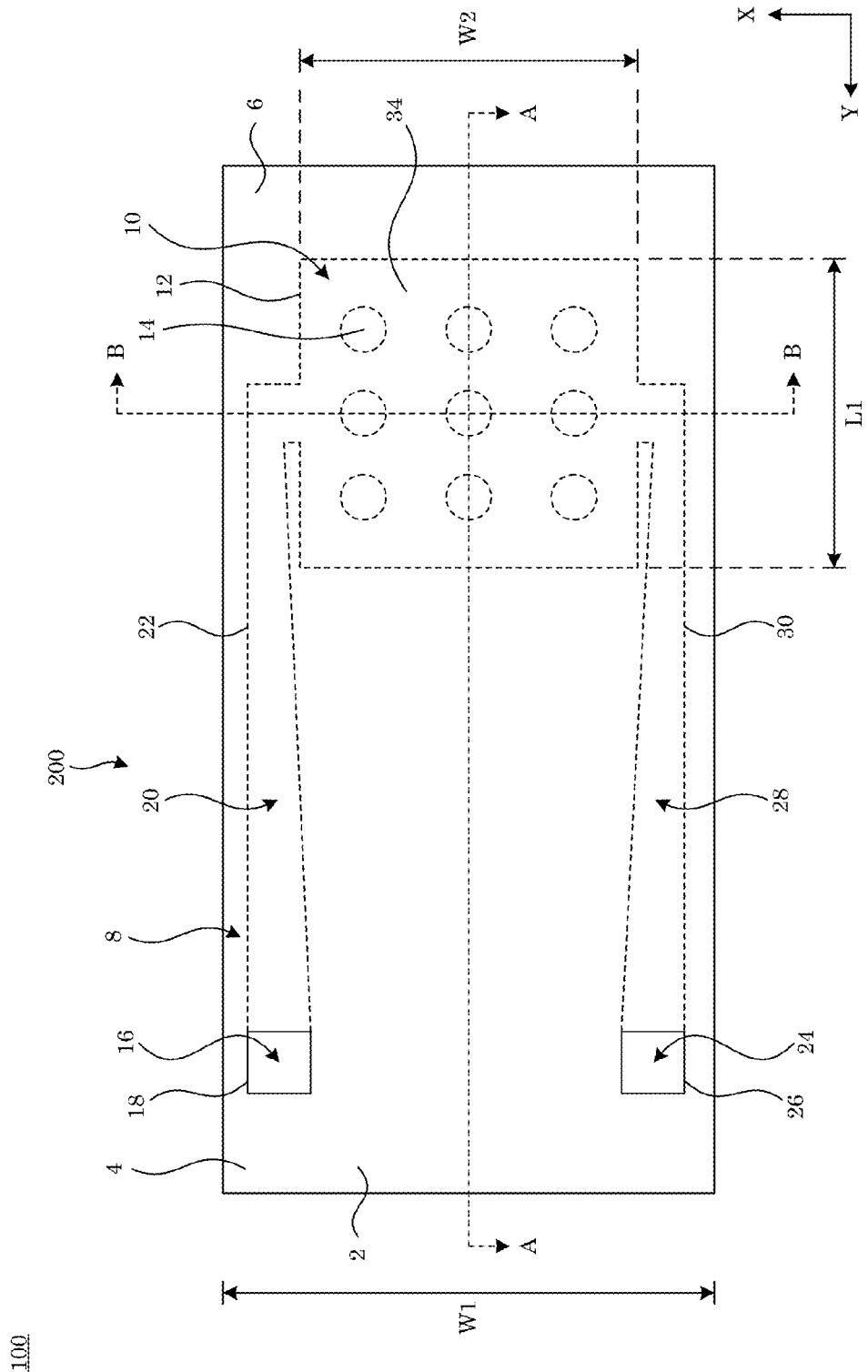
FIG. 2 shows a top view of the fluid sampler shown in FIG. 1.
Figure 3:
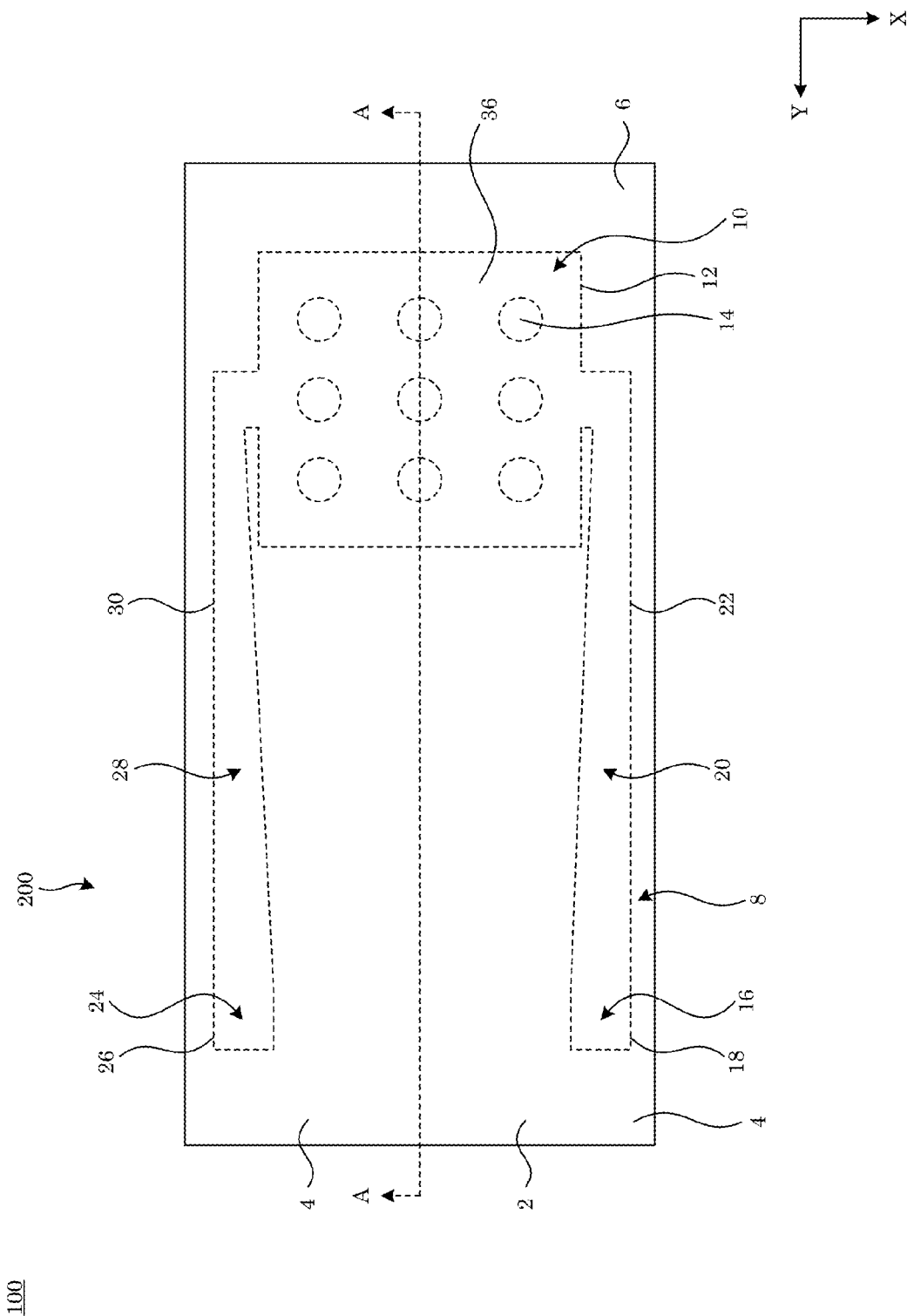
FIG. 3 shows a bottom view of the fluid sampler shown in FIG. 1.
Figure 4:
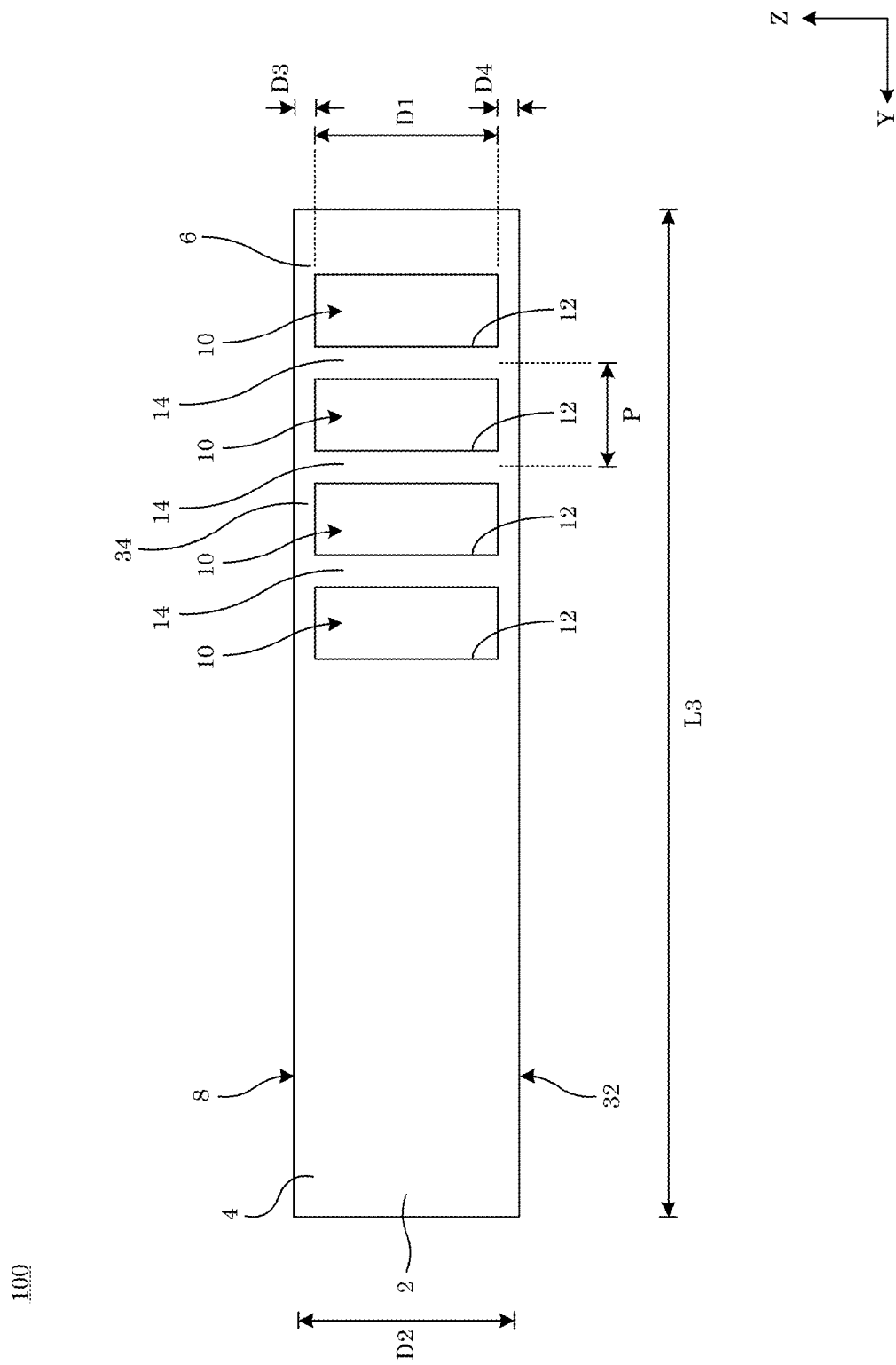
FIG. 4 shows a cross-section along line A-A of the fluid sampler shown in FIG. 2 according to an embodiment.
Figure 5:
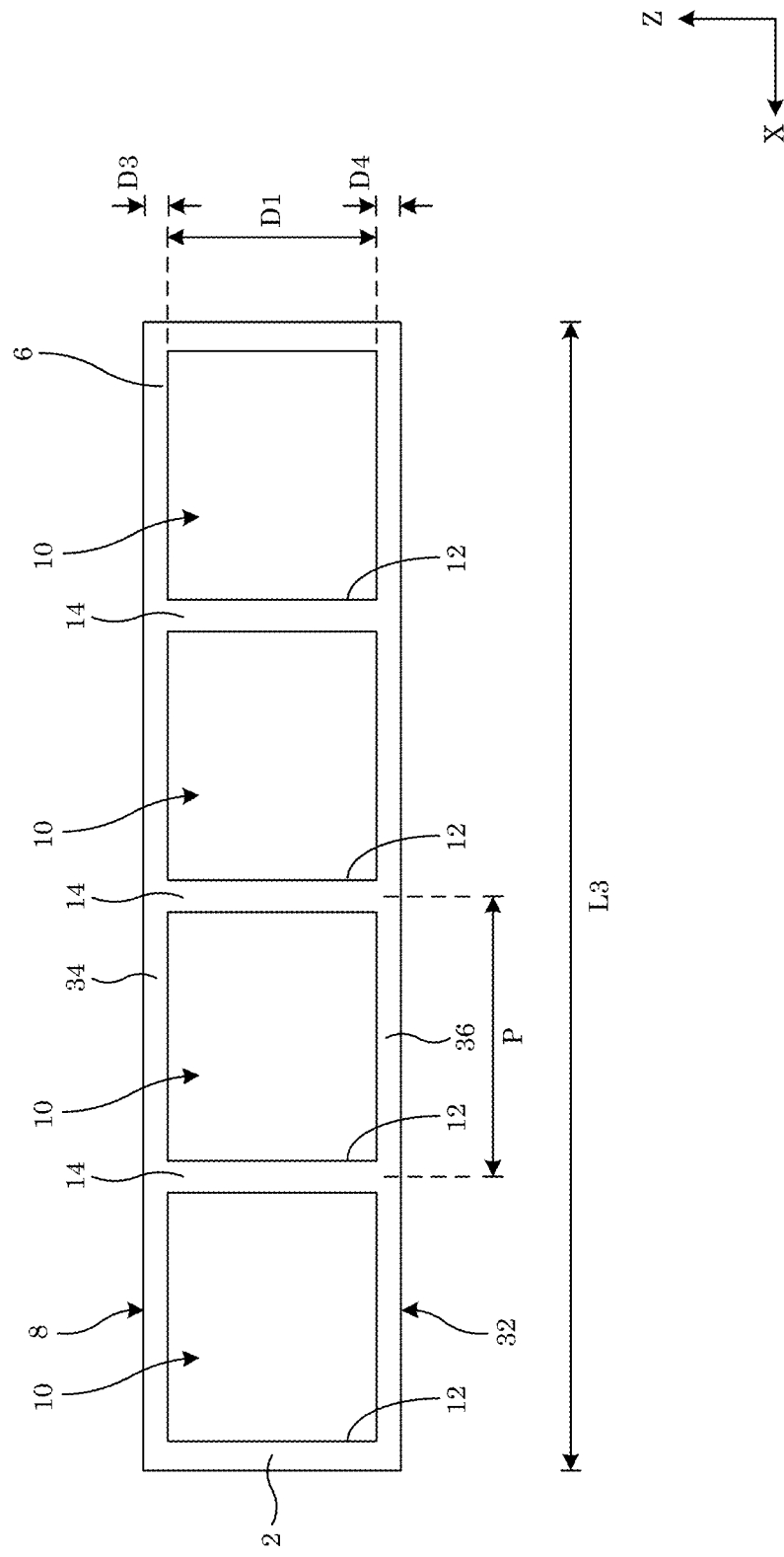
FIG. 5 shows a cross-section along line B-B of the fluid sampler shown in FIG. 2.

In fluid sampler 100, sample cell 200 includes viewing reservoir 10 that can have a shape (e.g., circular, square, polygonal, and the like) effective for viewing fluid disposed therein from first view membrane 34 to second view membrane 36. In an embodiment, viewing reservoir 10 has a rectangular shape (e.g., as shown in FIG. 2) with a length L1 and width D2, wherein sample cell 200 has width W1. Moreover, length L1 can be from 10 micrometers (μm) to 2000 μm, specifically 20 μm to 500 μm, and more specifically from 100 μm to 200 μm. Width W1 and width W2 independently can be from 2 millimeters (mm) to 10 mm, specifically 4 mm to 8 mm, and more specifically from 4 mm to 6 mm.

A number of pillars 14 is selected to provide substantially constant separation distance D1. Separation distance D1 can be from 10 nm to 1000 nm, specifically 20 nm to 500 nm, and more specifically 50 nm to 200 nm. The number of pillars 14 can be, e.g., from 1 to 1,000,000 and selected based on a surface area of first view membrane 34 or second view membrane 36. A cross-sectional thickness of pillars can be from 10 nm to 1000 nm, specifically 20 nm to 500 nm, and more specifically 25 nm to 50 nm. Neighboring pillars 14 can have pitch P from 400 nm to 50000 nm, specifically 1000 nm to 4000 nm, and more specifically 1000 nm to 2000 nm. Pillars 14 can have a same shape or different shapes from one another. The shape of pillars 14 independently can be columnar, cylindrical, frustoconical, polygonal, irregular, contoured, and the like. Pillar 14 can be solid or have an internal cavity that provides a structure to pillar 14 such as an annular shape (e.g., wherein pillar 14 is a frustocone or an annular frustocone (i.e., a frustocone with an annular cross-section)). An aspect ratio (i.e., D1:T (see, e.g., FIG. 4) of pillar 14 can be any ratio effective to provide a substantially constant separation D1 between view membranes (34, 36). Exemplary aspect ratios (D1:T) of pillar 14 is from $1:10^6$ to $10^6:1$, specifically 10:1 to 0.01:1, and more specifically, from 1:1 to 0.1:1.

Pillars 14 provide substantially constant separation distance D1 between first view membrane 34 and second view membrane 36, wherein under a compression force (due to a compressive stress) subjected to pillar 14 across first view membrane 34 and second view membrane 36, separation distance D1 is conserved at pillar 14. Moreover, under a tensive force (due to a tensile stress) subjected to pillar 14, pillar 14 provides substantially constant separation distance D1 between view membranes (34, 36) and remains in physical contact with view membranes (34, 36). The compression force or tensive force can be a result of a temperature or pressure under which sample cell 200 is subjected. It is contemplated that the temperature or pressure subjected to sample cell 200 can be external to sample cell 200, internal to sample cell 200 or a combination thereof. An external temperature or external pressure can be subjected to sample cell 200, e.g., at first surface 8, second surface 32, or a combination from an outside of viewing reservoir 10. Internal temperature or internal pressure can be present in viewing reservoir 10. Moreover, the pressure or temperature can be an absolute pressure or absolute temperature based on a reference scale or can be a differential pressure or a differential temperature across view membrane (34 or 36). Further, the pressure or temperature can be a change in the external pressure or external temperature; or internal pressure or internal temperature of viewing reservoir 10. Accordingly, pillar 14 separates first view membrane 34 from second view membrane 36 at substantially constant separation distance D1 such that separation distance D1 is invariable with respect to a temperature and invariable with respect to a pressure to which sample cell 200 is subjected.

Sample cell 200 can include a number of layers of a same or different material. Substrate 2 can include silicon, silicon dioxide, $SiO_2$, glass, fused silica, SiC, sapphire, GaAs, InP, or a combination thereof. An oxide layer can be disposed on substrate and can include silicon dioxide, aluminum oxide, cerium oxide, hafnium oxide, lanthanum oxide, or other transition metal, or lanthanide oxides, or a combination thereof. A structural layer can be included in sample cell 200 and can include, e.g., silicon nitride, Si, $SiO_2$, SiC, BN, graphene, diamond, or a combination thereof. First view membrane and the second view membrane independently comprise silicon nitride, Si, $SiO_2$, SiC, BN, graphene, diamond, or a combination thereof. Electrodes (e.g., 50, 52) are disposed on substrate 2 and can include an electrically conductive material such as a transition metal (e.g., tantalum and the like), conductive oxide (indium tin oxide and the like), Au, Pt, W, glassy carbon, graphene or a combination thereof.

It is contemplated that viewing reservoir 10 interposed between first view membrane 34 and second view membrane 36 is formed by removal (e.g., etching) of sacrificial member 68. Sacrificial member 68 can include chromium oxide that is selectively removed by a chromium oxide etchant. The chromium oxide etchant can include cerium IV, hydrochloric acid, nitric acid, perchloric acid, or a combination thereof.

The fluid can be disposed in viewing reservoir 10 of sample cell 200 and can include a gas, a liquid, or a combination thereof. In an environment, the fluid is the liquid. In a certain embodiment, particles (e.g., solid, colloidal, gel, nanoparticles, microparticles, and the like) are disposed in the liquid that flow in viewing reservoir 10. The fluid can be hydrophobic, hydrophilic, organic, inorganic, biological, ionically charged, zwitterionic, and the like. A pressure of the fluid can be from $10^{-6}$ Pascals (Pa) to $10^7$ Pa, specifically from $10^{-2}$ Pa to $10^6$ Pa, and more specifically from 1 Pa to $10^5$ Pa. A temperature of the fluid can be from −269° C. to 1200° C., specifically from −196° C. to 1000° C., and more specifically from −100° C. to 1000° C.

Sample cell 200 is disposed in holder 202. Holder 202 can be made from a variety of materials, and elements (e.g., lid 206, lid 210, body 204, armature receiver 212, and the like) independently can be a plastic, metal, ceramic, glass, or a combination thereof. In an embodiment, holder 202 includes Titanium. To allow the device to be used in SEM and TEM systems, the components of the Sample cell 200 and Holder 202 are non-magnetic so as to not distort the electron probe beams.

Holder 202 is disposed on transfer arm 250. Transfer arm 250 can be made from a variety of materials, and elements (e.g., armature 252, handle 264, and the like) independently can be a plastic, metal, ceramic, glass, or a combination thereof. In an embodiment, holder 202 includes copper and receives an elastomeric gasket at gasket receiver 258.

The fluid can be communicated in conduits (20, 28) hydrostatically, pneumatically, electrokinetically, under capillary flow, and the like, or a combination thereof.

In an embodiment, a process for making fluid sampler 100 includes providing sample cell 200 disposed sample cell 200 in holder 202; disposing holder 202 on transfer arm 250.

Sample cell 200 can be made in various ways including selective removal of a sacrificial member from between view membranes (34, 36). According to an embodiment, a process for selectively removing a sacrificial member from a composite structure includes: providing a first structural layer; disposing the sacrificial member on the first structural layer, the sacrificial member including chromium oxide; disposing a second structural layer on the sacrificial member such that: the sacrificial member is interposed between the first structural layer and the second structural layer, and a composite structure is formed by the first structural layer and the second structural layer; contacting the sacrificial member with an etchant, the etchant being selective to etch chromium oxide and substantially inert with respect to etching the composite structure; and selectively etching the sacrificial member by the etchant to selectively remove the sacrificial member from the composite structure, wherein the first structural layer and the second structural layer are spaced apart by a separation distance by removal of the sacrificial member.

The process for selectively removing the sacrificial member from the composite structure further can include: disposing the first structural layer on a substrate; disposing an oxide layer on the first structural layer; disposing an electrode on the oxide layer such that the sacrificial member is partially disposed on the electrode. The process for selectively removing the sacrificial member from the composite structure further can include patterning the sacrificial member with a plurality of apertures prior to disposing the second structural layer. The process for selectively removing the sacrificial member from the composite structure further can include forming a plurality of pillars by disposing the second structural letter in the apertures of the sacrificial member. The process for selectively removing the sacrificial member from the composite structure further can include etching a fluid port in the substrate. The process for selectively removing the sacrificial member from the composite structure further can include forming a viewing reservoir by selectively removing the sacrificial member; and connecting the fluid port in the substrate to the viewing reservoir by selectively removing the sacrificial member such that the fluid port is in fluid communication with the viewing reservoir. In a certain embodiment, in the process for selectively removing the sacrificial member from the composite structure, the composite structure is sample cell 200 in which viewing reservoir 10 and fluid port (e.g., 16, 24, and the like) receive a fluid.

Figure 34:
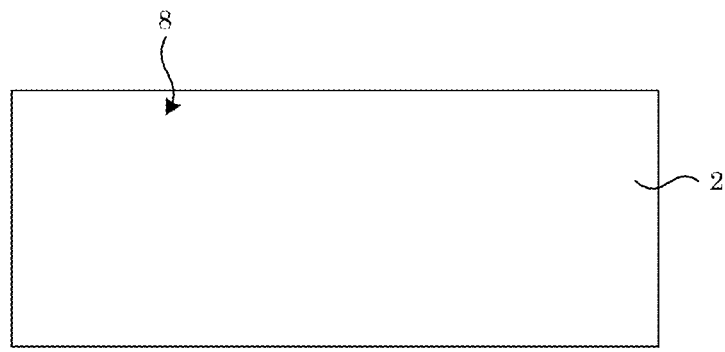
FIG. 34 shows structures formed in making a sample cell.
Figure 34:
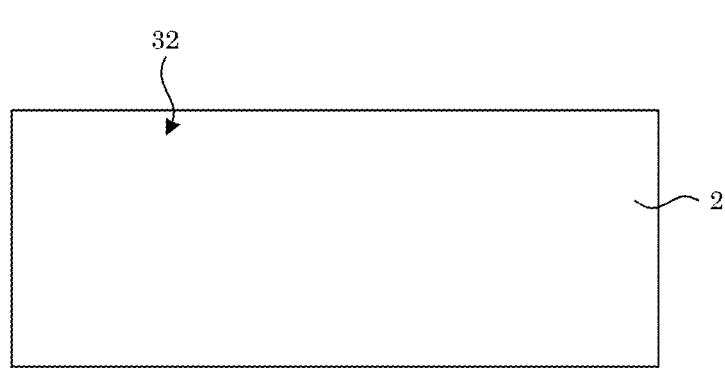
Figure 34:
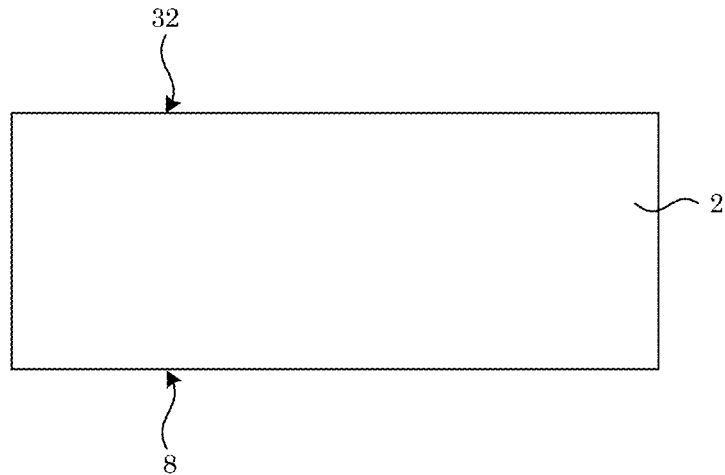
Figure 35:
FIG. 35 shows structures formed in making a sample cell.
Figure 35:
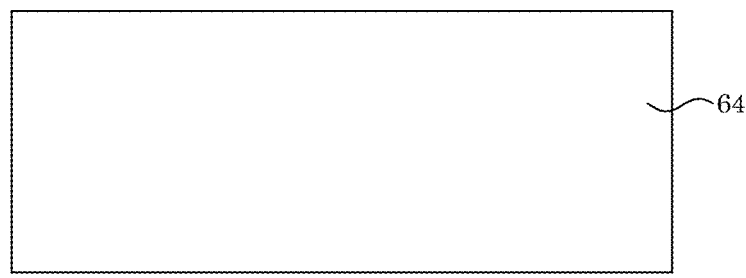
Figure 35:
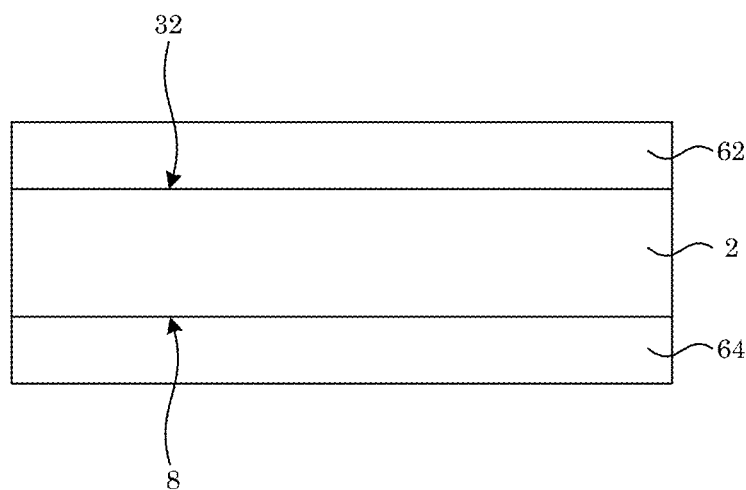
Figure 36:
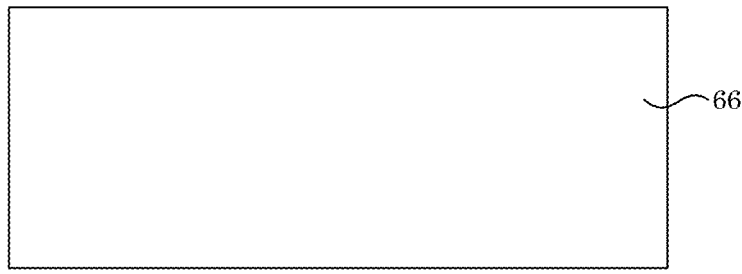
FIG. 36 shows structures formed in making a sample cell.
Figure 36:
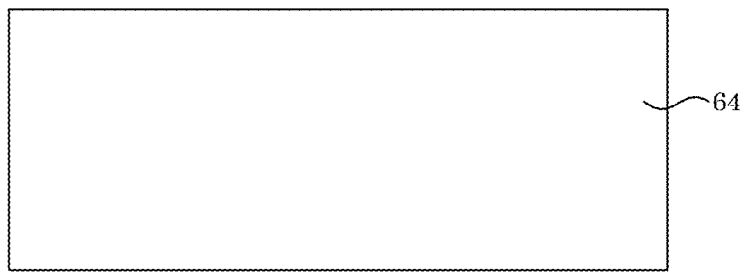
Figure 36:
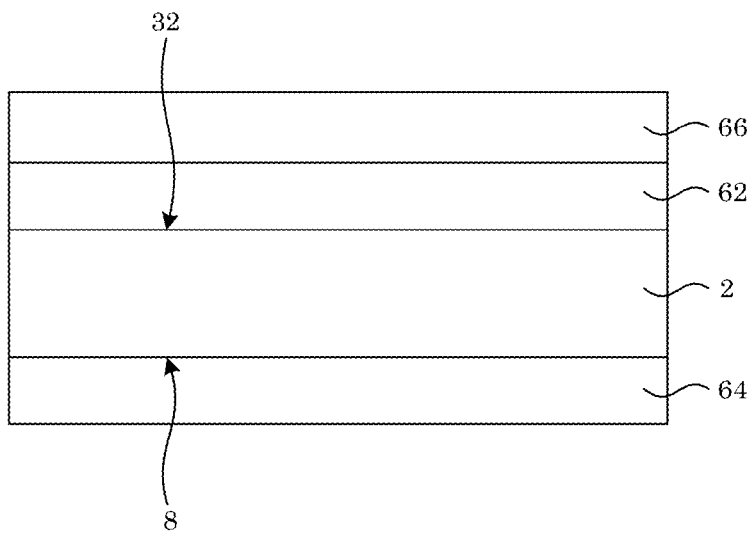
Figure 37:
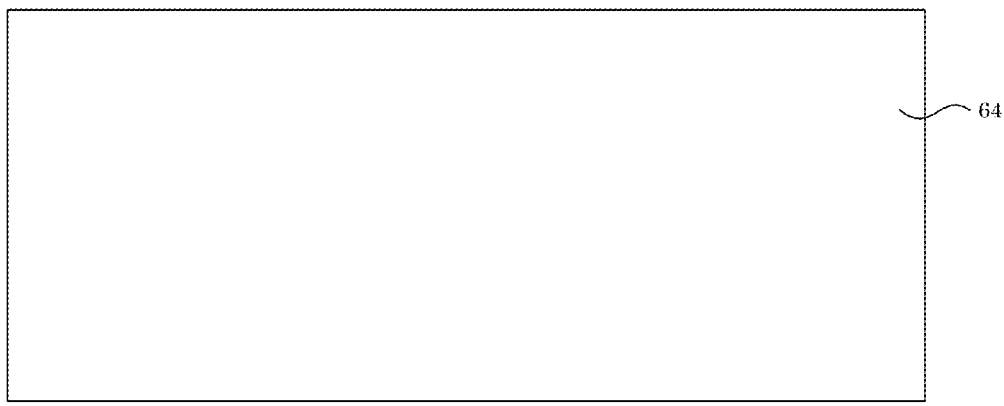
FIG. 37 shows structures formed in making a sample cell.
Figure 37:
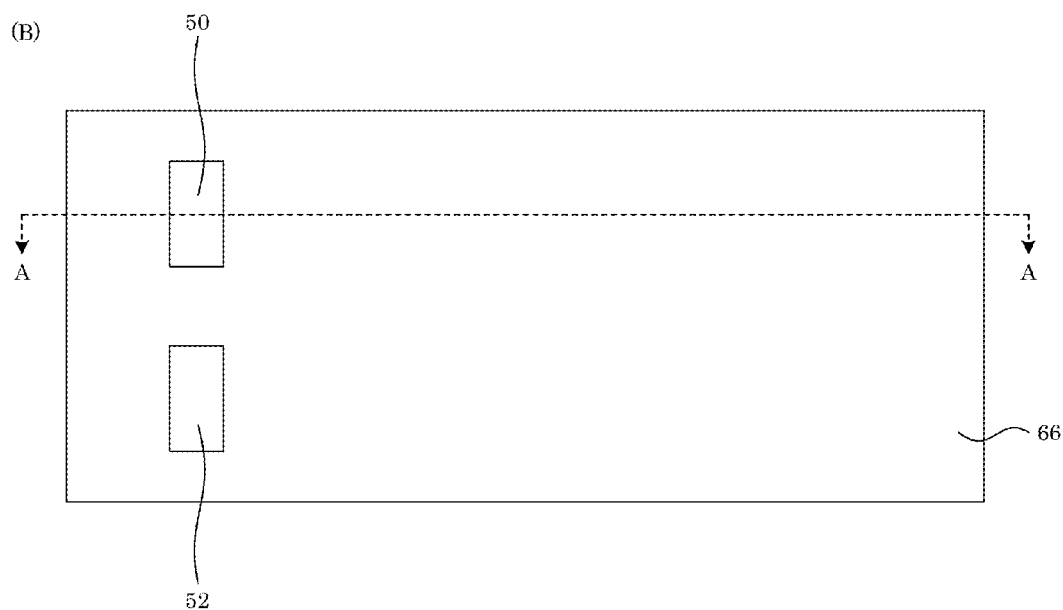
Figure 38:
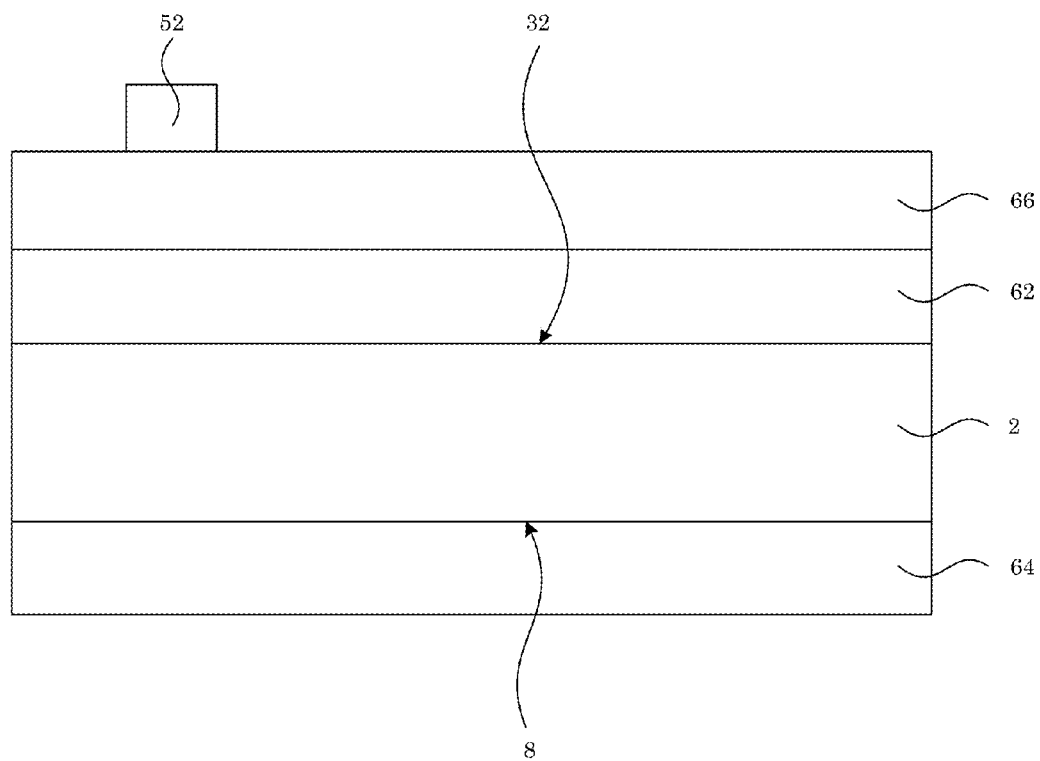
FIG. 38 shows structures formed in making a sample cell.
Figure 39:
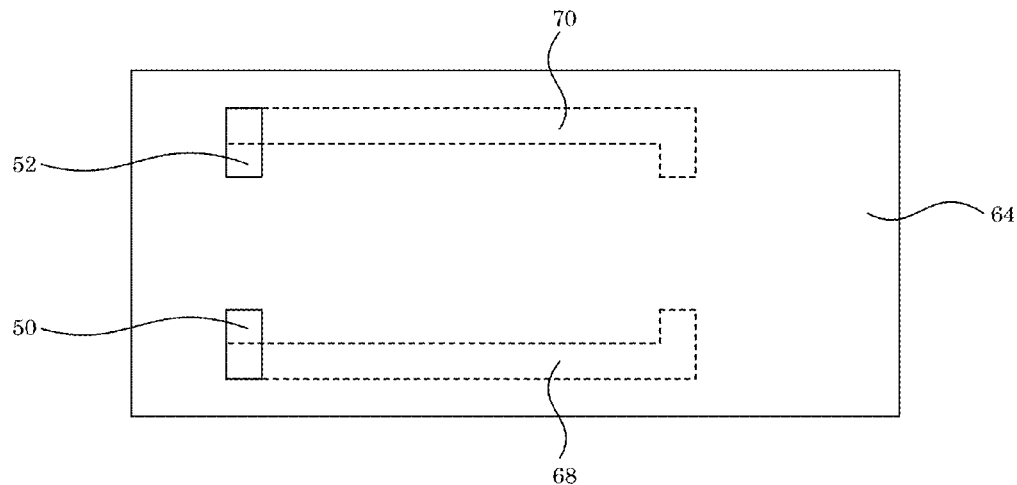
FIG. 39 shows structures formed in making a sample cell.
Figure 39:
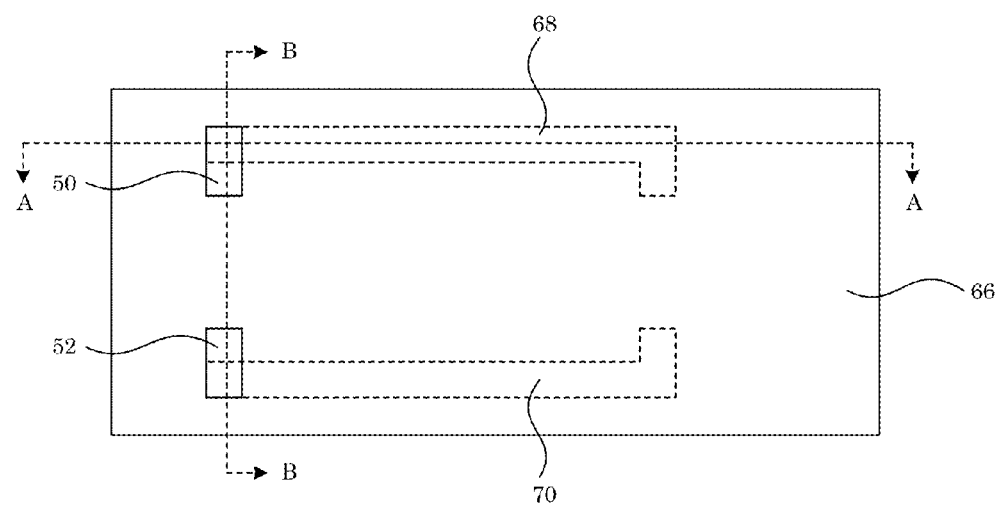
Figure 40:
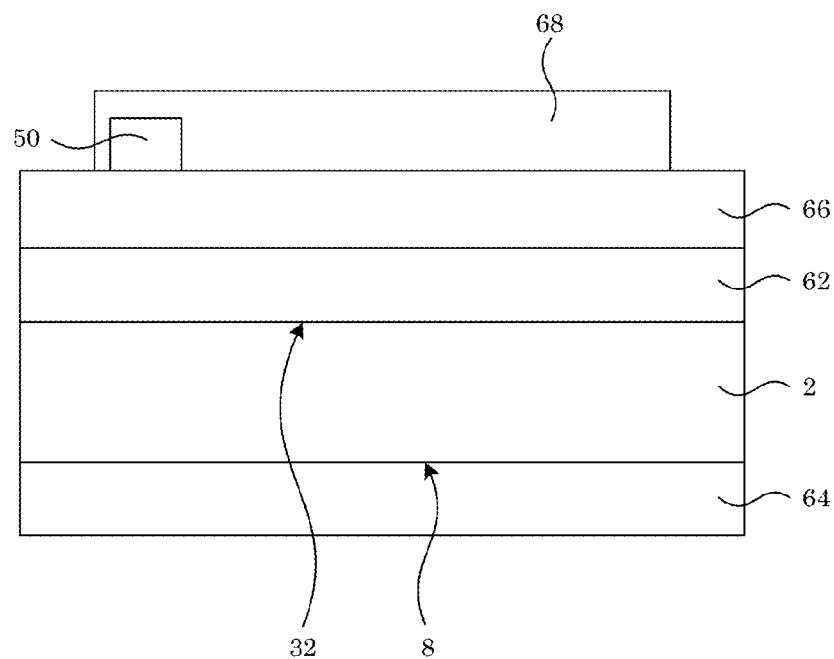
FIG. 40 shows structures formed in making a sample cell.
Figure 40:
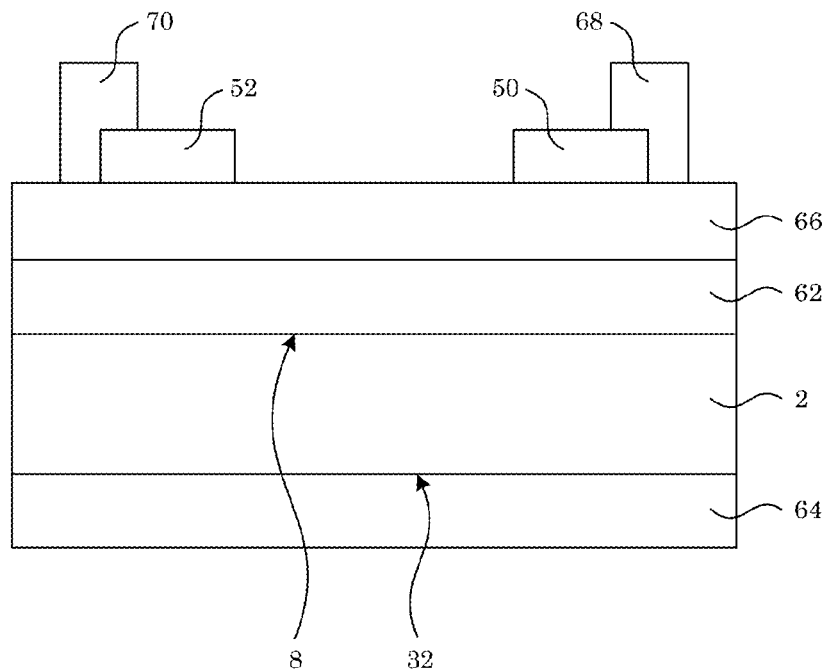
Figure 41:
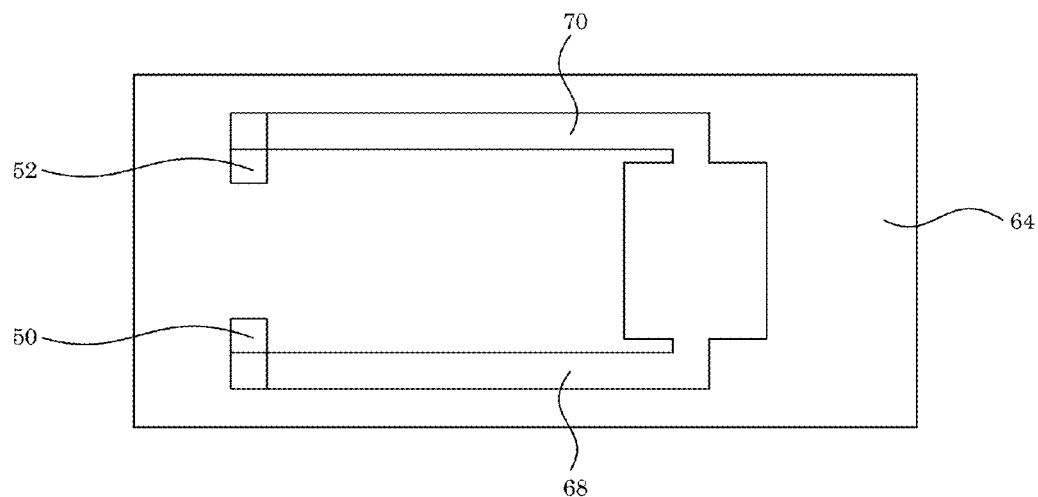
FIG. 41 shows structures formed in making a sample cell.
Figure 41:
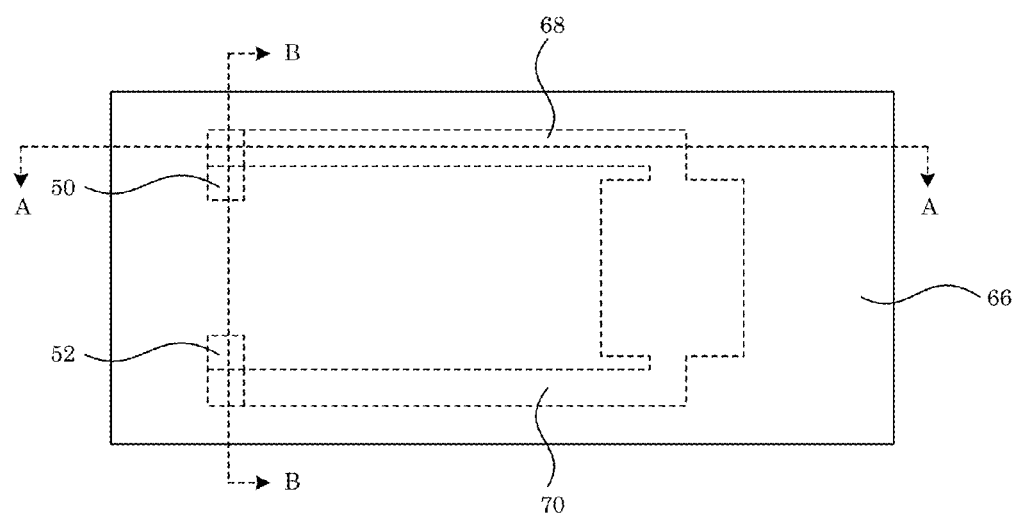
Figure 42:
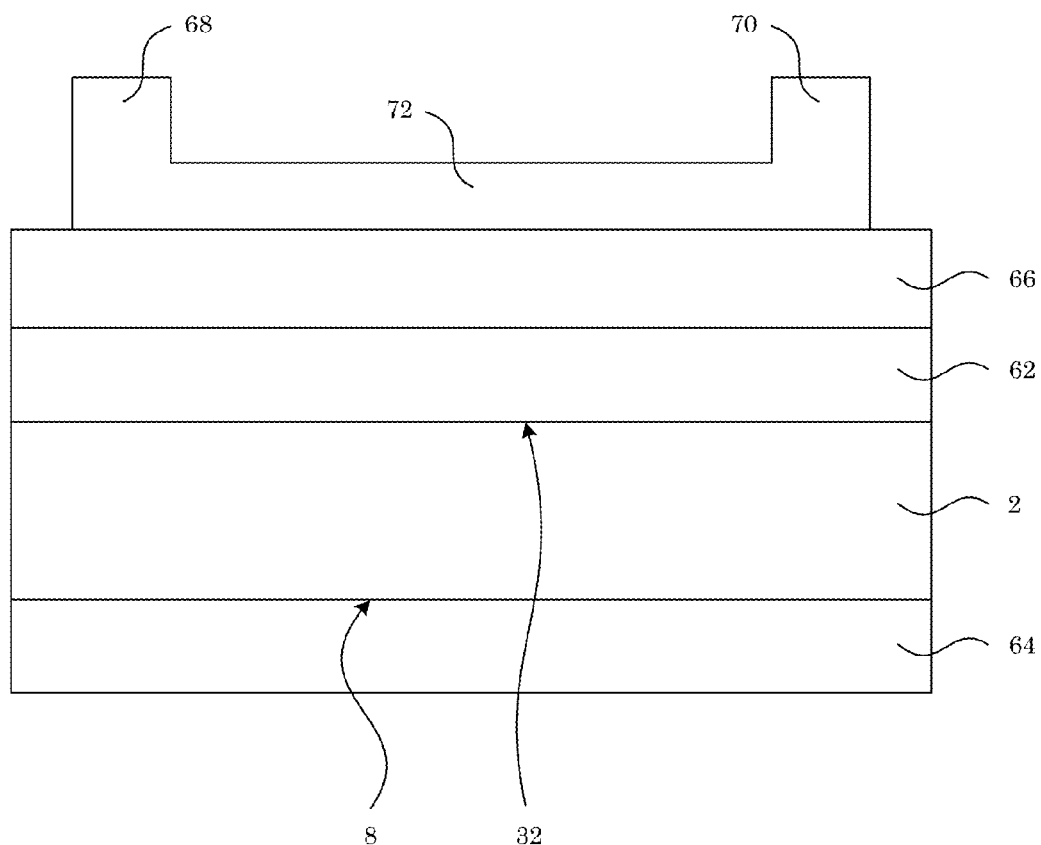
FIG. 42 shows structures formed in making a sample cell.
Figure 43:
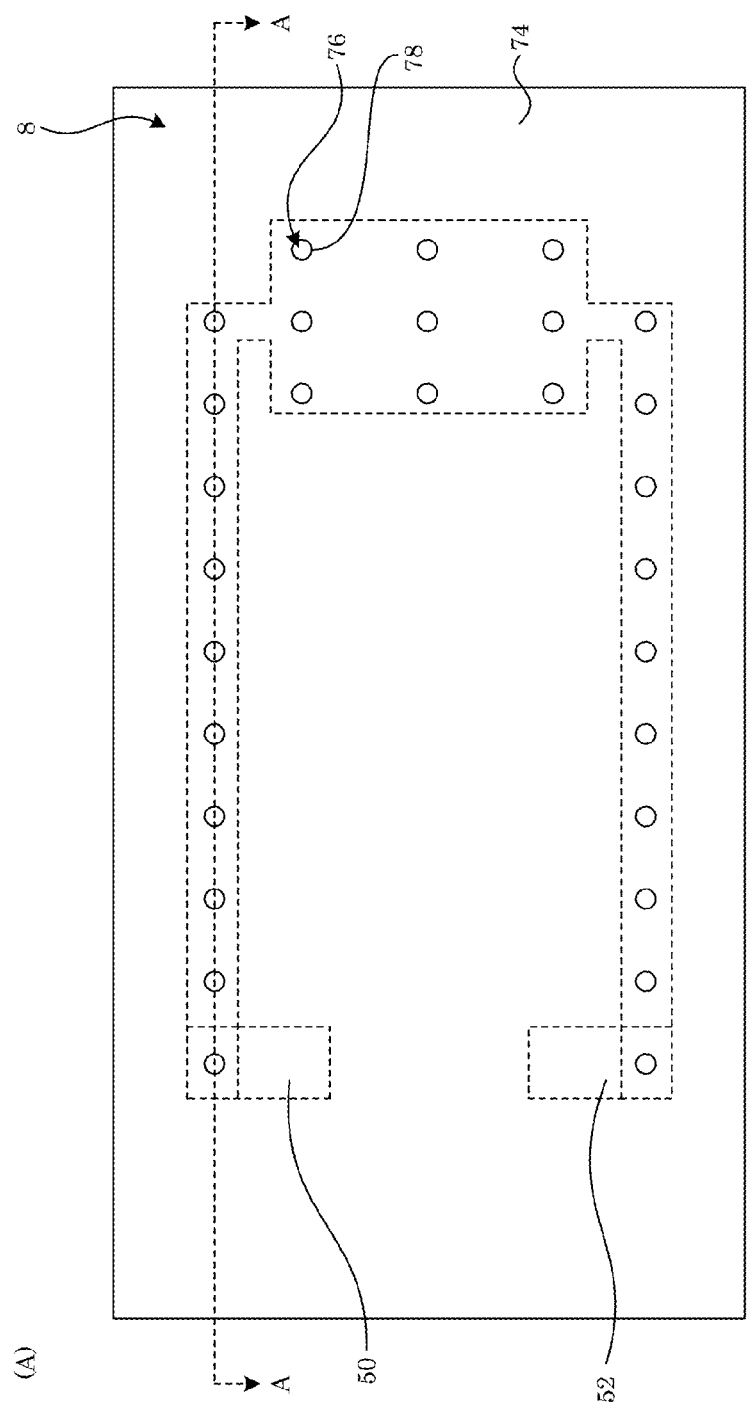
FIG. 43 shows structures formed in making a sample cell.
Figure 44:
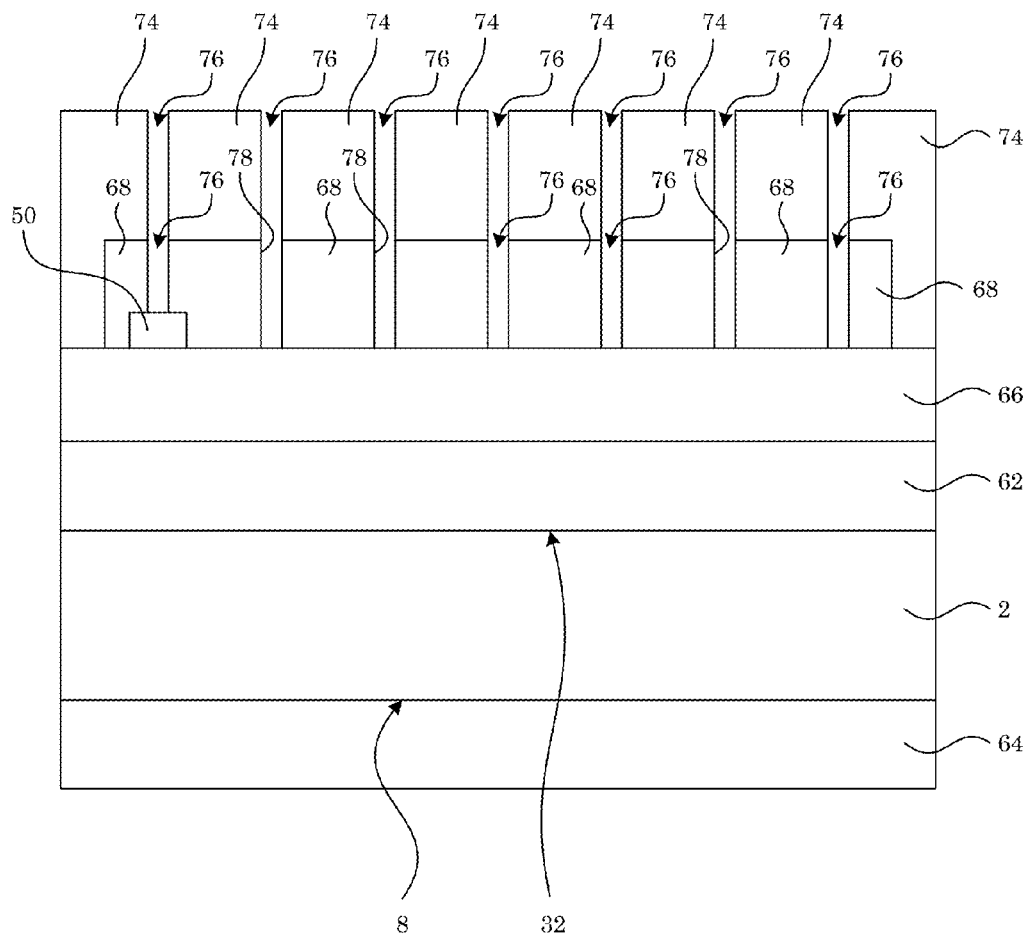
FIG. 44 shows structures formed in making a sample cell.
Figure 45:
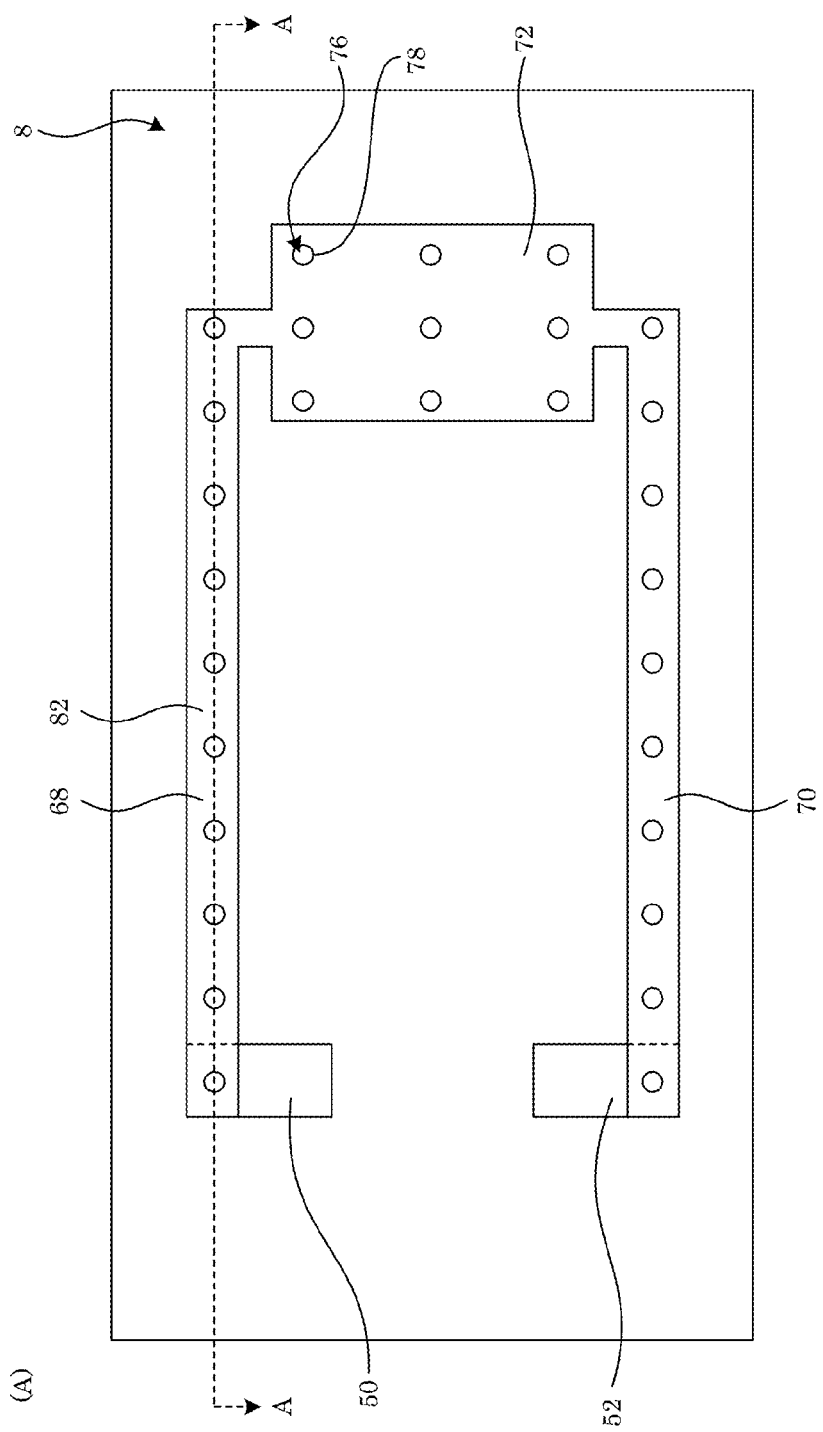
FIG. 45 shows structures formed in making a sample cell.
Figure 46:
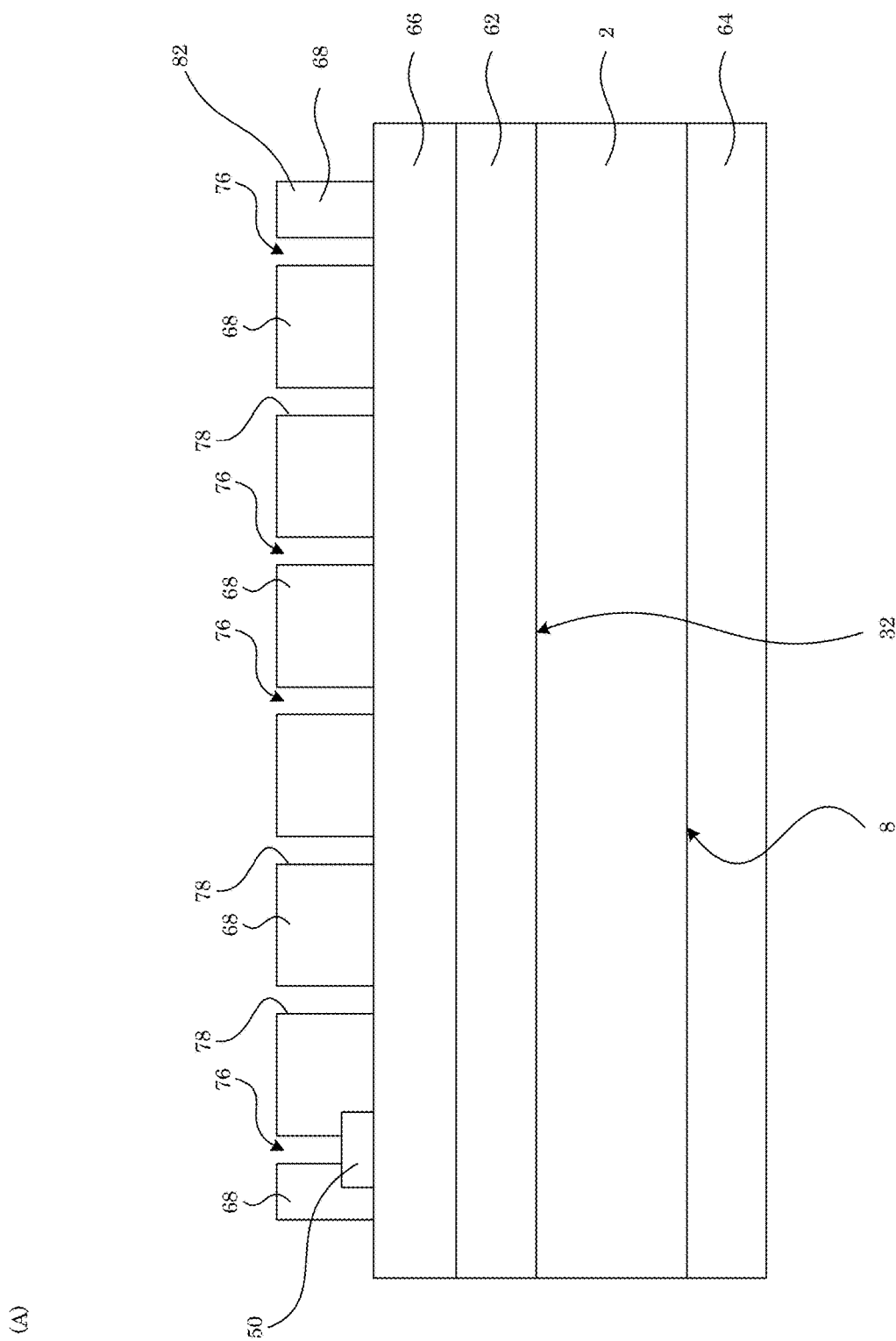
FIG. 46 shows structures formed in making a sample cell.
Figure 47:
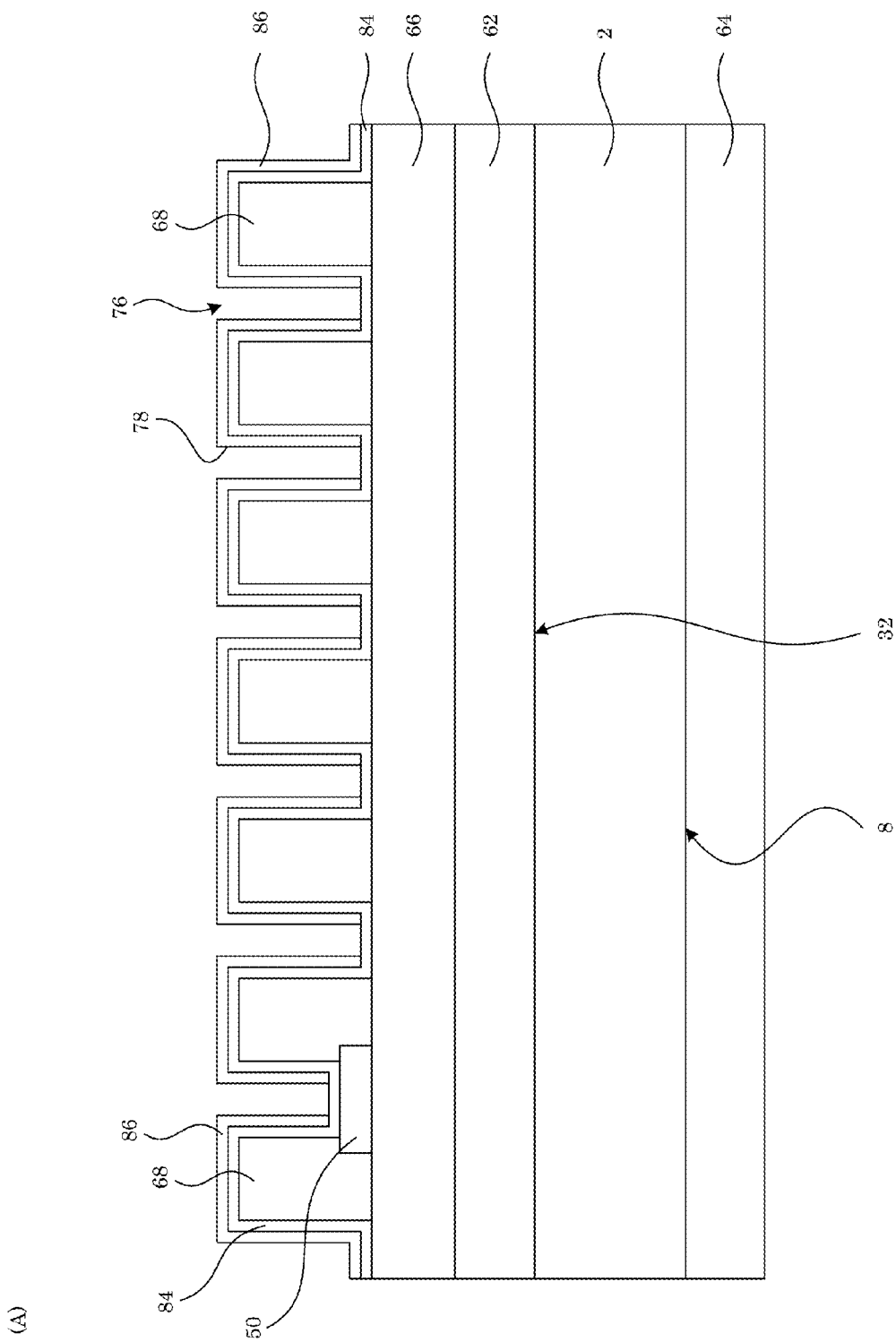
FIG. 47 shows structures formed in making a sample cell.
Figure 48:
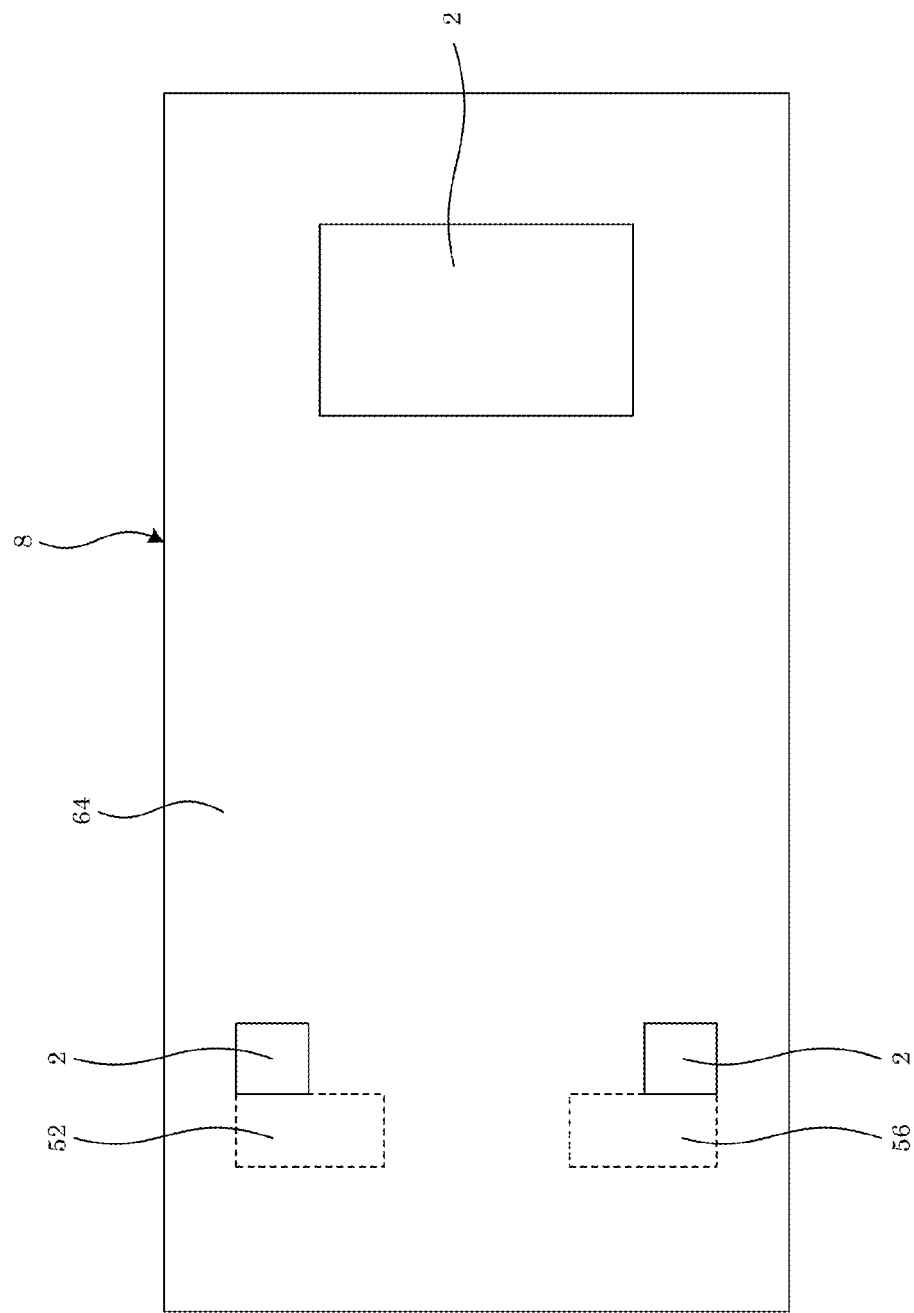
FIG. 48 shows structures formed in making a sample cell.
Figure 49:
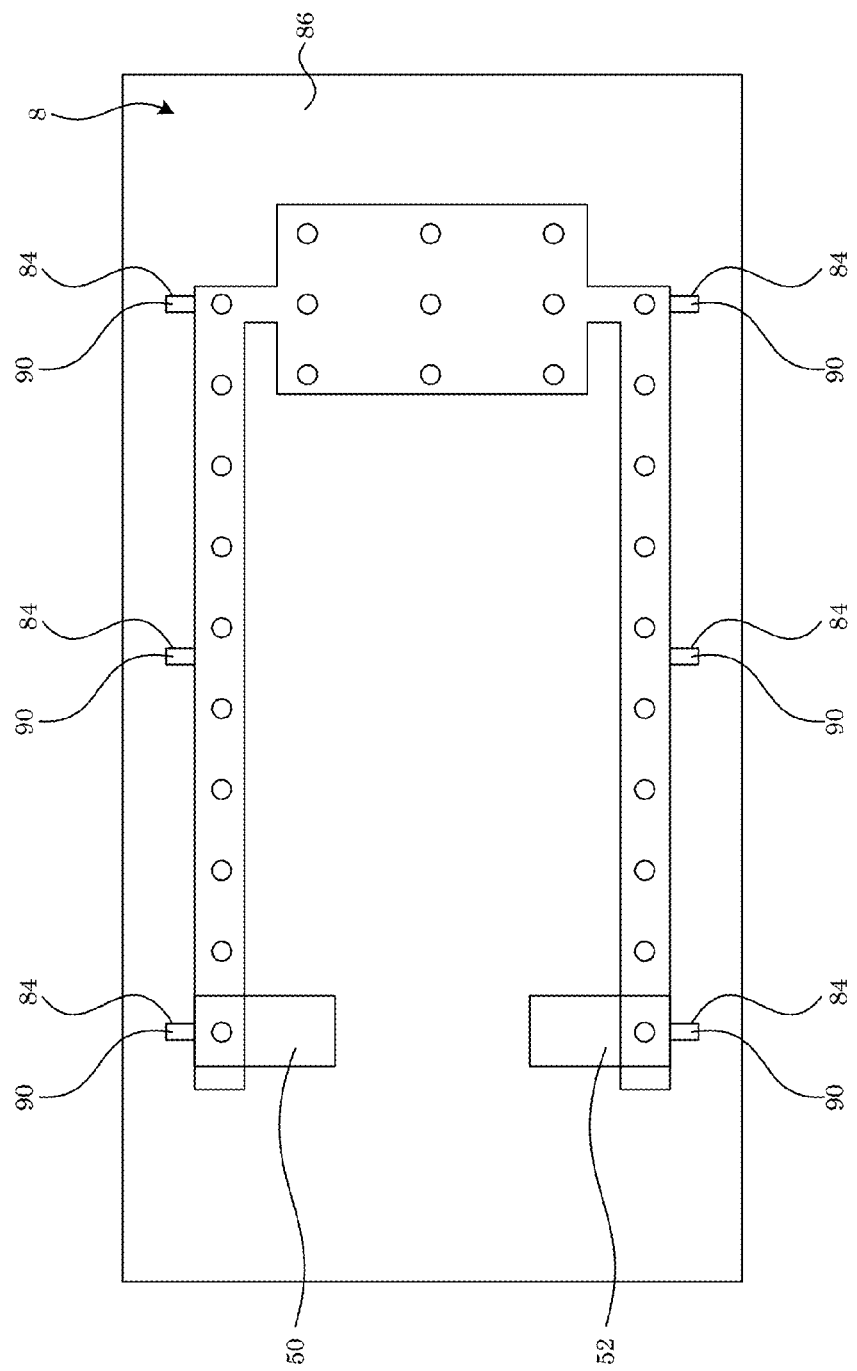
FIG. 49 shows structures formed in making a sample cell.
Figure 50:
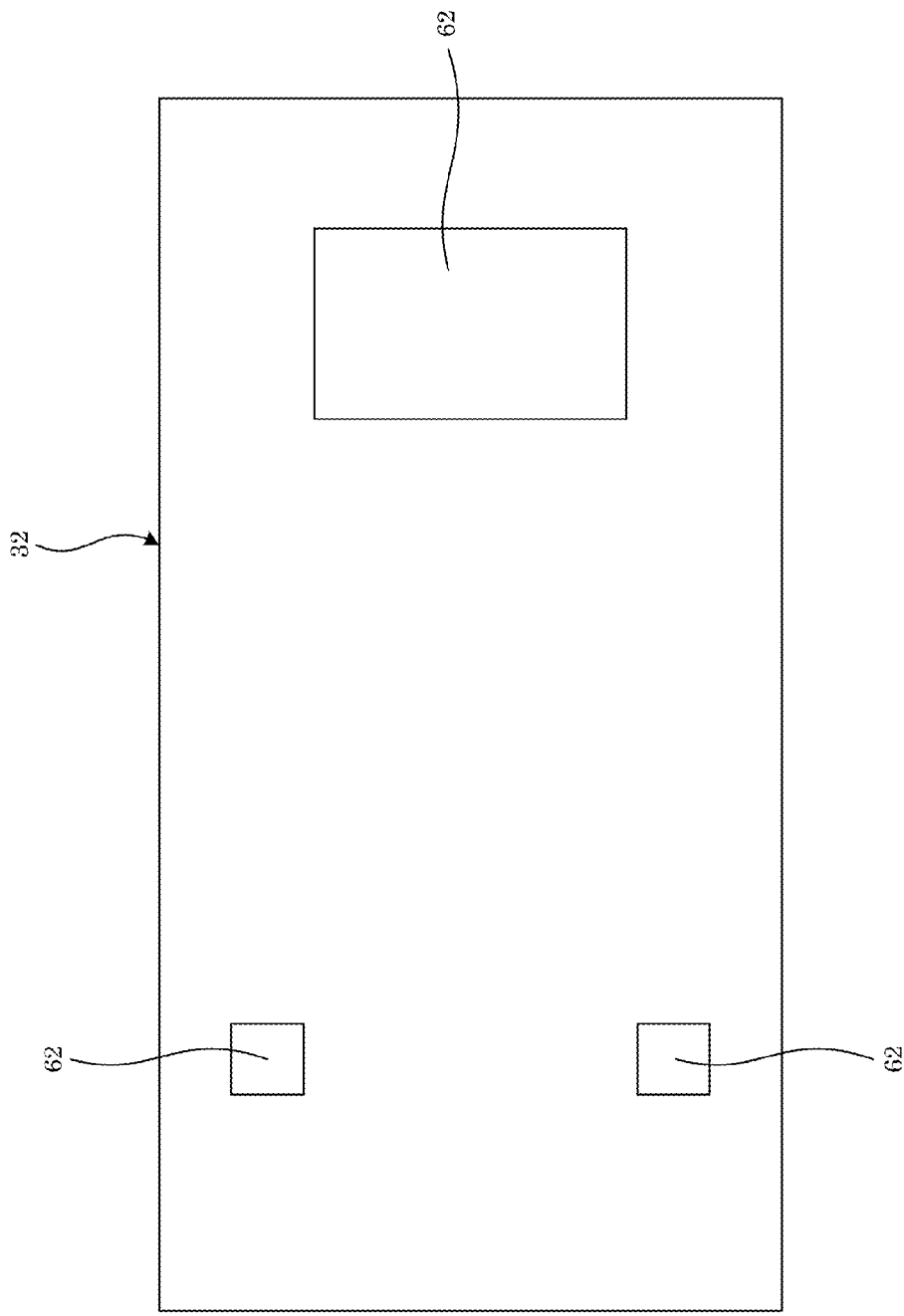
FIG. 50 shows structures formed in making a sample cell.
Figure 51:
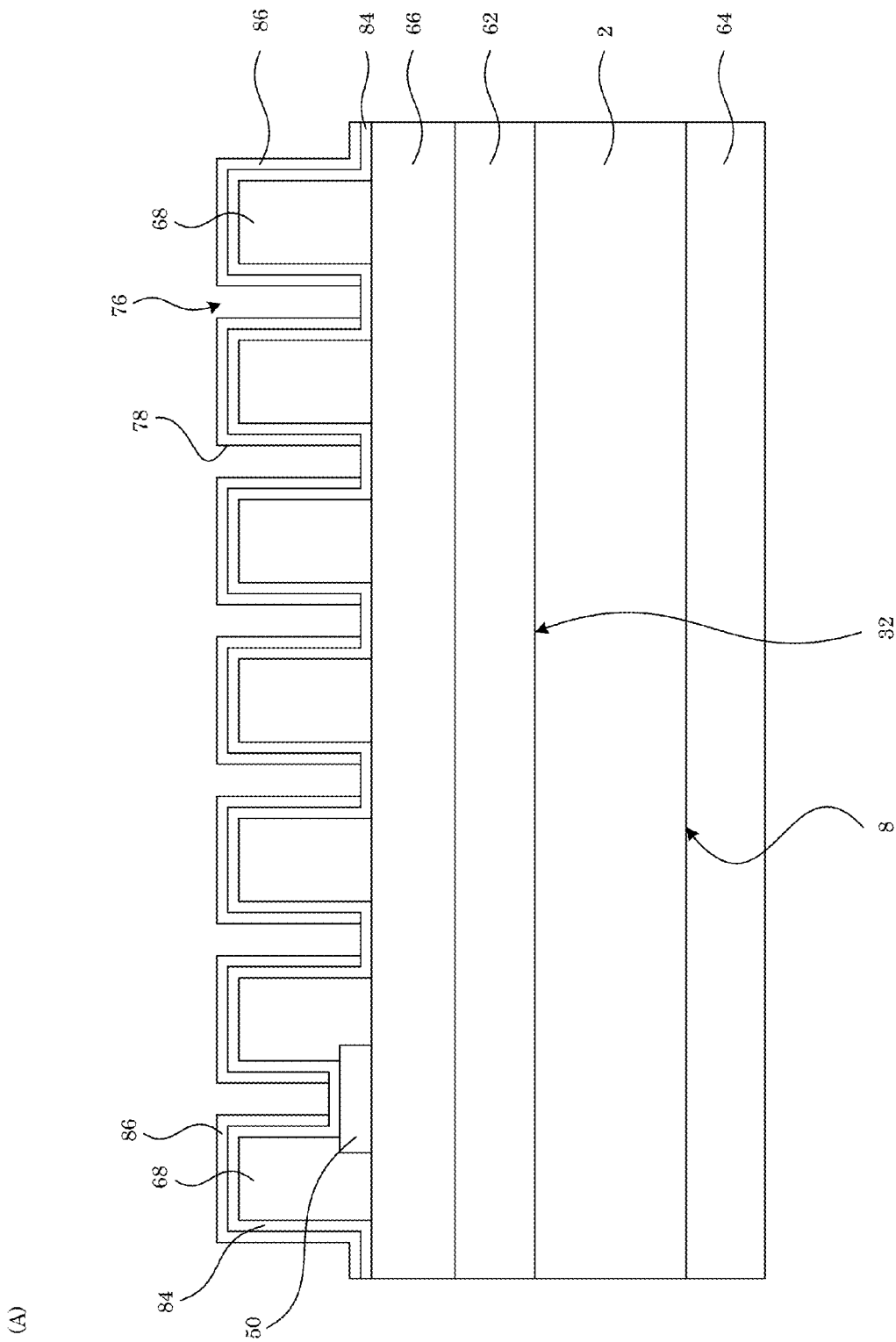
FIG. 51 shows structures formed in making a sample cell.

In an embodiment, with reference to FIG. 34, FIG. 35, FIG. 36, FIG. 37, FIG. 38, FIG. 39, FIG. 40, FIG. 41, FIG. 42, FIG. 43, FIG. 44, FIG. 45, FIG. 46, FIG. 47, FIG. 48, FIG. 49, FIG. 50, FIG. 51, FIG. 52, FIG. 53, FIG. 54, and FIG. 55, a process for making sample cell 200 includes: providing substrate 2 (FIG. 34); disposing first structural layer 62 on second surface 32 of substrate 2 (FIG. 35); disposing third structural layer 64 on first surface 8 of substrate 2 (FIG. 35); disposing first oxide layer 66 on first structural layer 62 (FIG. 36); disposing a plurality of electrodes (e.g., 50, 52) on first oxide layer 66 (FIG. 37, FIG. 38); disposing sacrificial member (68, 70, 72) on first oxide layer 66 (FIG. 39, FIG. 40 (panel A: cross-section along line A-A shown in FIG. 39; panel B: cross-section along line B-B shown in FIG. 39), FIG. 41, FIG. 42 (cross-section along line A-A shown in FIG. 41), sacrificial member (68, 70, 72) including: chromium oxide, a first thickness of sacrificial member (68, 70) in contact with a portion of each electrode (50, 52), and a second thickness of sacrificial member (72) that is less than then the first thickness in an area on substrate 2 that corresponds to viewing reservoir 10 (to be formed upon removal of sacrificial member 72); forming a plurality of apertures 76 bounded by wall 78 in sacrificial member (68, 70, 72) (FIG. 43, FIG. 44 (cross-section along line A-A shown in FIG. 43), FIG. 45, FIG. 46 (cross-section along line A-A shown in FIG. 45)) by: disposing photoresist mask 74 on sacrificial member (68, 70, 72), patterning photoresist mask 74 with a plurality of apertures 80, and removing a portion of sacrificial member (68, 70, 72) coincident with apertures 80 to form apertures 76 in sacrificial member (68, 70, 72); disposing second oxide layer 84 on sacrificial member (68, 70, 72) such that sacrificial member (60, 70, 72) is interposed between second oxide layer 84 and first structural layer 62 (FIG. 47, cross-sectional view); disposing second structural layer 86 on second oxide layer 84 such that the sacrificial member (68, 70, 72) is interposed between second structural layer 86 and first structural layer 62; etching third structural layer 64 disposed on first surface 8 of substrate 2 to expose a portion of substrate 2 at first surface 8 (FIG. 48); forming etchant trench 90 on second surface 32 to expose a portion of oxide layer 84 (FIG. 49); etching a portion of substrate 2 from first surface 8 to second surface 32 to expose a portion of first structural layer 62 in an area that corresponds to viewing reservoir 10 (to be formed) and a fluid port (to be formed) (FIG. 50); and selectively etching sacrificial member (68, 70, 72) to remove sacrificial member (60, 70, 72) from between first structural layer 62 and second structural layer 86 to form sample cell 200 (FIG. 51).

Figure 52:
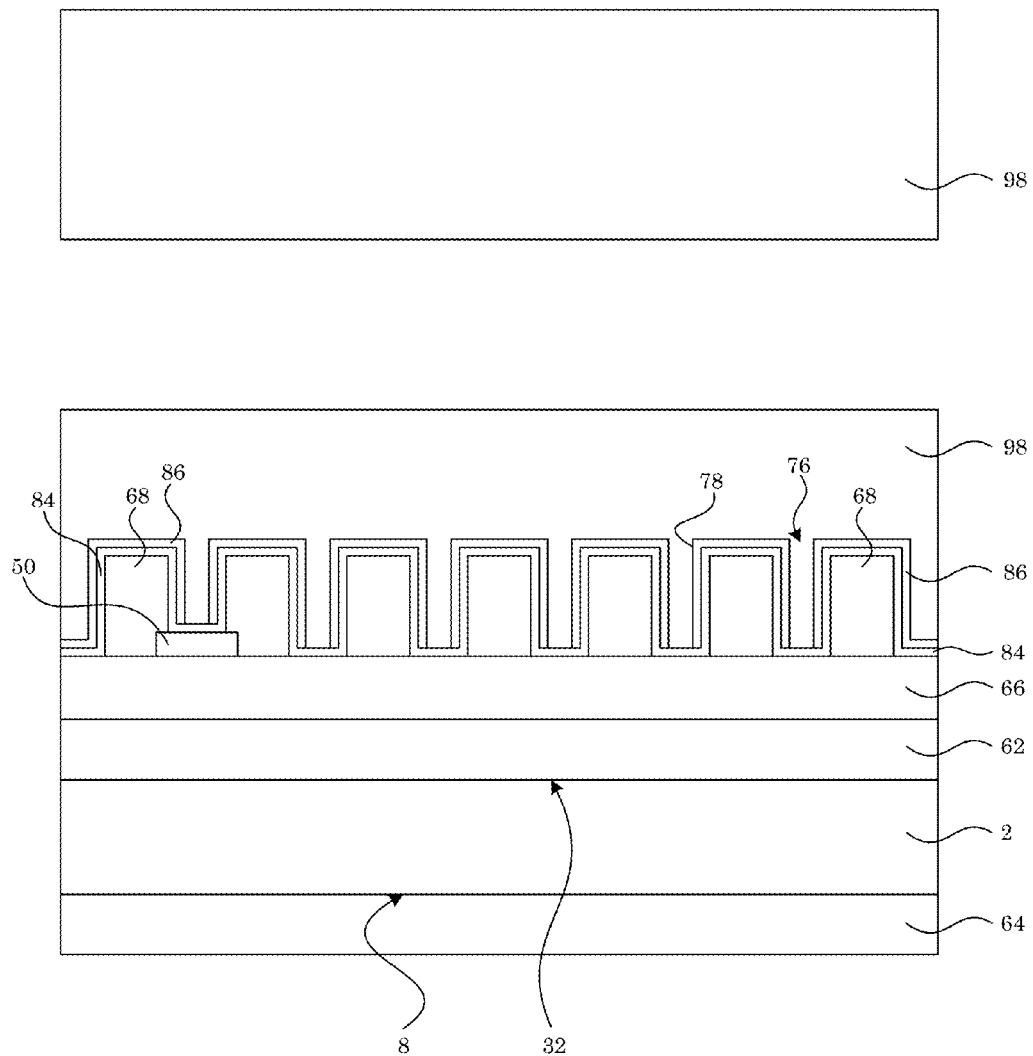
FIG. 52 shows structures formed in making a sample cell.
Figure 53:
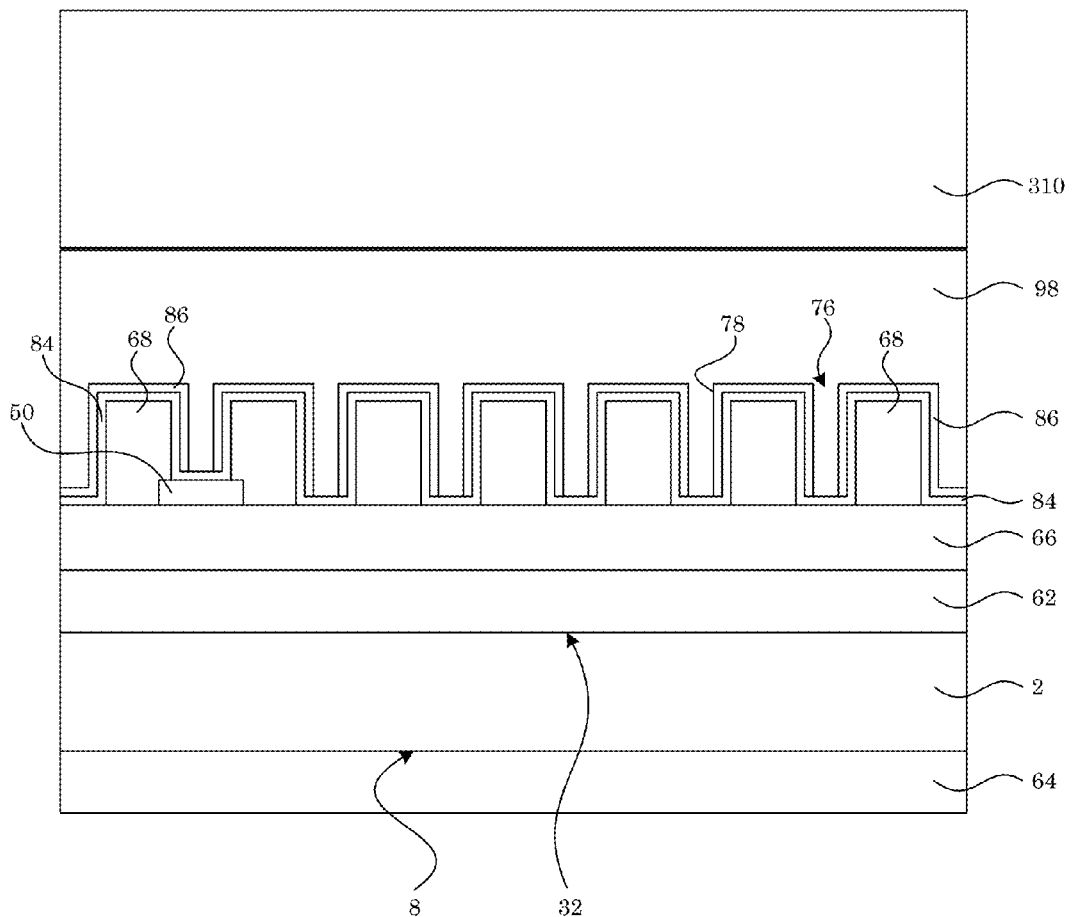
FIG. 53 shows structures formed in making a sample cell.

The process for making sample cell 200 further can include disposing third oxide layer 98 on second surface 32 to fill etchant trench 90 (FIG. 52: panel A top view, and panel B cross-section along line A-A shown in panel A). The process for making sample cell 200 further can include disposing protective layer 310 on third oxide layer 98 (FIG. 53). The process for making sample cell 200 further can include (FIG. 54): patterning protective layer 310; etching third oxide layer 98 to expose viewing reservoir 10; and etching third oxide layer 98 to expose electrodes (e.g., 50, 52).

In an embodiment of the process for making sample cell 200, substrate 2 can include silicon; first structural layer 62 can include silicon nitride; third structural layer 64 can include silicon nitride; first oxide layer 66 can include silicon dioxide; electrodes (e.g., 50, 52) can include tantalum; sacrificial member (68, 70, 72) can include chromium oxide; photoresist mask 74 can include a polymer; second oxide layer 84 can include silicon dioxide; second structural layer 86 can include silicon nitride; third oxide layer 98 can include silicon dioxide; and protective layer 310 can include a polymer such as a polyimide.

In an embodiment of the process for making sample cell 200, disposing first structural layer 62 on second surface 32 of substrate 2 (FIG. 35) can include physical vapor deposition, chemical vapor deposition, low-pressure chemical vapor deposition, plasma-enhanced chemical vapor deposition, atomic layer deposition, plasma-enhance atomic layer deposition.

Disposing third structural layer 64 on first surface 8 of substrate 2 (FIG. 35) can include physical vapor deposition, chemical vapor deposition, low-pressure chemical vapor deposition, plasma-enhanced chemical vapor deposition, atomic layer deposition, plasma-enhance atomic layer deposition.

Disposing first oxide layer 66 on first structural layer 62 (FIG. 36) can include physical vapor deposition, chemical vapor deposition, low-pressure chemical vapor deposition, plasma-enhanced chemical vapor deposition, atomic layer deposition, plasma-enhance atomic layer deposition.

Disposing electrodes (e.g., 50, 52) on first oxide layer 66 (FIG. 37, FIG. 38) can include physical vapor deposition, chemical vapor deposition, low-pressure chemical vapor deposition, plasma-enhanced chemical vapor deposition, atomic layer deposition, plasma-enhance atomic layer deposition, and electrodeposition.

Figure 55:
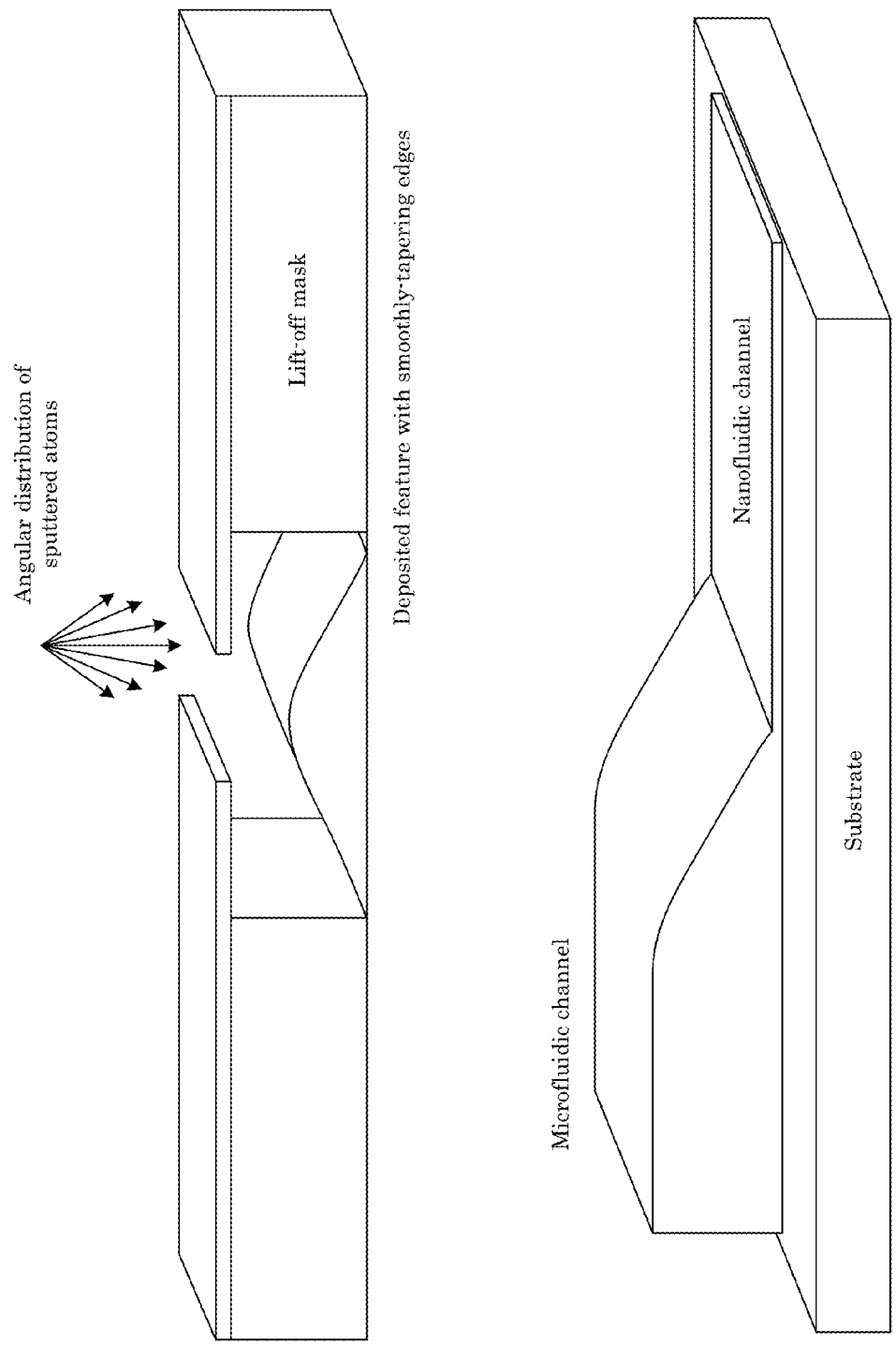
FIG. 55 shows structures formed in making a sample cell.

With reference to FIG. 55, disposing sacrificial member (68, 70, 72) on first oxide layer 66 (FIG. 39) can include physical vapor deposition, chemical vapor deposition, low-pressure chemical vapor deposition, plasma-enhanced chemical vapor deposition, atomic layer deposition, plasma-enhance atomic layer deposition.

Forming a plurality of apertures 76 bounded by wall 78 in sacrificial member (68, 70, 72) can include (FIG. 43): disposing photoresist mask 74 on sacrificial member (68, 70, 72) by spin or spray coating, patterning (by optical, electron-beam or ion-beam lithography) photoresist mask 74 with a plurality of apertures 80, and removing (by application of a selective wet chemical etch, or selective reactive ion etch, or downstream plasma) a portion of sacrificial member (68, 70, 72) coincident with apertures 80 to form apertures 76 in sacrificial member (68, 70, 72).

Disposing second oxide layer 84 on sacrificial member (68, 70, 72) such that sacrificial member (60, 70, 72) is interposed between second oxide layer 84 and first structural layer 62 (FIG. 47, cross-sectional view) can include physical vapor deposition, chemical vapor deposition, low-pressure chemical vapor deposition, plasma-enhanced chemical vapor deposition, atomic layer deposition, plasma-enhance atomic layer deposition.

Disposing second structural layer 86 on second oxide layer 84 such that the sacrificial member (68, 70, 72) is interposed between second structural layer 86 and first structural layer 62 can include physical vapor deposition, chemical vapor deposition, low-pressure chemical vapor deposition, plasma-enhanced chemical vapor deposition, atomic layer deposition, plasma-enhance atomic layer deposition.

Etching third structural layer 64 disposed on first surface 8 of substrate 2 to expose a portion of substrate 2 at first surface 8 (FIG. 48) can include the use of a selective, or timed wet chemical etch, or selective, or timed reactive ion etch, or selective, or timed downstream plasma etch, or timed or end-pointed ion milling.

Forming etchant trench 90 on second surface 32 to expose a portion of oxide layer 84 (FIG. 49) can include the use of a selective, or timed wet chemical etch, or selective, or timed reactive ion etch, or selective, or timed downstream plasma etch.

Etching a portion of substrate 2 from first surface 8 to second surface 32 to expose a portion of first structural layer 62 in an area that corresponds to viewing reservoir 10 (to be formed) and a fluid port (to be formed) (FIG. 50) can include the use of a selective, or timed wet chemical etch, or selective, or timed reactive ion etch, or selective, or timed downstream plasma etch.

Selectively etching sacrificial member (68, 70, 72) to remove sacrificial member (60, 70, 72) from between first structural layer 62 and second structural layer 86 to form sample cell 200 (FIG. 51) can include the use of a selective wet, or vapor phase chemical etch.

Disposing third oxide layer 98 on second surface 32 to fill etchant trench 90 (FIG. 52) can include physical vapor deposition, chemical vapor deposition, low-pressure chemical vapor deposition, plasma-enhanced chemical vapor deposition, atomic layer deposition, plasma-enhance atomic layer deposition.

Disposing protective layer 310 on third oxide layer 98 (FIG. 53) can include spin or spray coating.

Figure 54:
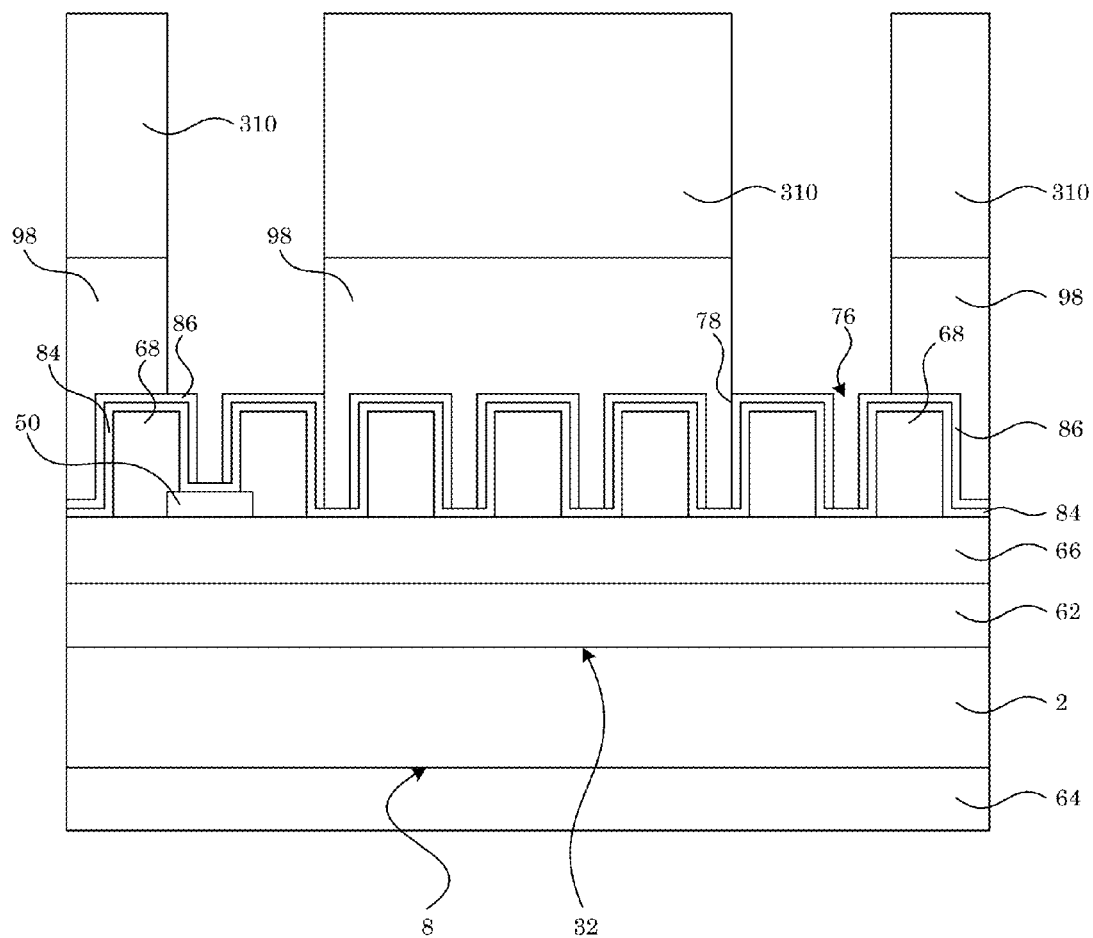
FIG. 54 shows structures formed in making a sample cell.

With reference to FIG. 54, patterning protective layer 310; etching third oxide layer 98 to expose viewing reservoir 10; and etching third oxide layer 98 to expose electrodes (e.g., 50, 52) can include optical, electron-beam, or ion beam lithography, selective, or timed, wet chemical etching, or selective or timed reactive ion, or downstream reactive plasma etching, or timed or end-pointed ion milling.

In forming sacrificial member (68, 70, 72), as shown in FIG. 55, tapered profiles (e.g., wall 40) a broad angular distribution of atomic deposition that occurs in atomic sputtering in combination with an undercut lift-off mask produces a smooth transition from micro- to nanoscale features to provide a flow transition from microfluidic flow to nanofluidic flow.

Fluid sampler 100 has numerous beneficial uses, including containing a fluid in sample cell 200 and performing transmission electron microscopy on the fluid disposed in sample cell 200.

Fluid sampler 100 has numerous advantageous and beneficial properties. In an aspect, fluid sampler 100 provides a substantially uniform and thin fluid layer to enable high-resolution imaging and spectroscopy, a means of confining the chemistry of interest, which may be corrosive, or otherwise deleterious to a microscope or other measurement apparatus, inside the sampler, thus protecting the microscope or other measurement apparatus and enabling the study of a wider range of chemistries, a means of achieving higher pressures than can otherwise be attained, a means to control fluid flows with substantially improved temporal control.

The articles and processes herein are illustrated further by the following Example, which is non-limiting.

EXAMPLE

High-Resolution Imaging and Spectroscopy at High Pressure in a TEM.

This Example describes quantitative core-loss electron energy-loss spectroscopy of iron oxide nanoparticles and imaging resolution of Ag nanoparticles in liquid down to 0.24 nm, in both transmission and scanning-transmission modes, in a novel, monolithic liquid cell developed for the transmission electron microscope (TEM). At typical SiN membrane thicknesses of 50 nm the liquid layer thickness has a maximum change of only 30 nm for the entire TEM viewing area of 200 μm×200 μm.

Transmission electron microscope (TEM), with its ability to deliver atomic-scale spatial, and <100 meV spectroscopic resolution, has enabled countless breakthroughs in materials science. Environmental TEMs (ETEMs) were developed to study reactions in gaseous environments. ETEMs can be limited in terms of the pressures and chemistries that can be accessed. Study of materials and processes in liquid environments is challenging and requires the use of special cells to encapsulate the liquid and protect the microscope. Creating a thin, uniform liquid layer in a device that permits high spatial and spectroscopic resolution was difficult.

Conventional liquid cells comprise a pair electron-transparent windows between which a layer of liquid is sandwiched. Control over the membrane separation is achieved by polystyrene microspheres, silicon dioxide or epoxies, or wafer bonding. Scanning TEM (STEM) imaging in micrometer-thick layers allows atomic resolution in gases. These conventional two-piece cells cannot accurately and reproducibly define a thin liquid layer and maintain its uniformity over a large observation area. The pressure difference between the inside and outside of the cell can cause significant membrane deformation (bulging) and large variations in liquid layer thickness. Both the membrane bulging effect and the difficulty of using spacers to reliably control the liquid layer thickness pose a major challenge to atomic-resolution TEM and quantitative electron energy-loss spectroscopy (EELS).

The sample cell in this Example overcomes these limits and includes a pillar-supported, monolithic liquid cell that eliminates spacers and limits bulging. This Example shows a combination of atomic-scale imaging, in both TEM and STEM modes, and quantitative EELS using this design. We discuss the design of the sample cell and identify structural and material parameters that affect its performance.

The effect of design parameters on the performance of the device was considered. We examined membrane and liquid thickness to achieve atomic-scale resolution in TEM and STEM modes. Conventionally, the image resolution in TEM mode for thick samples or a thick liquid cell has been estimated by considering the effect of chromatic aberration and assuming an energy spread estimated by the so-called Landau energy distribution. This Landau distribution is observed for thicknesses larger than $t/\lambda \approx 3$ (t is thickness and $\lambda$ is the inelastic mean free path) where individual plasmon and core-loss features are obscured. Chromatic aberration causes inelastically scattered electrons to be focused to a different plane from the elastically scattered electrons, contributing a background to the bright-field image; therefore, there will be an increasing loss of image contrast as the fraction of inelastically scattered electrons rises. For a total SiN thickness of 100 nm, a 75 nm thick layer of water, and an accelerating voltage of 300 kV, we find that the fraction of unscattered electrons is close to 25%. The remaining 75% of electrons, which are scattered by the membranes and liquid, include both inelastically and elastically scattered electrons. High-Resolution imaging is possible with a loss in contrast and a diminished signal-to-noise ratio (SNR), and resolution is weakly dependent on thickness in this range.

Image resolution in thick samples in STEM mode with an annular dark-field detector is determined by either broadening of the incident probe by multiple scattering or SNR constraints. Conventional experimental measurements and calculations indicate that for thicknesses of a liquid layer below ≈1 μm, resolution is determined by SNR and estimates of broadening do not match the experimentally obtained resolution for liquid cells or samples on thick substrates. The STEM SNR is estimated by calculating the intensity reaching the detector from elastic scattering in the liquid and membrane, which contributes the background, and the signal is the intensity reaching the detector via elastic scattering from the particle of interest. This method of calculation is applicable for estimating the resolution on the order of ≈1 nm, but will only be a rough approximation for systems which permit lattice resolution because the elastic scattering calculations do not account for Bragg diffraction. Nonetheless, using this method we estimate an SNR sufficient to obtain STEM resolution below 0.2 nm for the conditions applicable to the liquid cell described here, assuming a minimum SNR of 3.

Next, we consider the constraints that must be satisfied to enable quantitative, high-resolution EELS to be performed. First we focus on the design criteria for obtaining EELS of the liquid (rather than a solid particle in the liquid). At liquid layer thicknesses, t, much less than the inelastic scattering length, $\lambda$, the liquid EELS signal will be small compared to that from the membranes, while at large thicknesses ($t/\lambda > 3$) plural scattering obscures both the valence and core-loss regions. A good EELS signal can be obtained if, while minimizing multiple scattering, each electron experiences an average of one inelastic scattering event, i.e., $t/\lambda$ should be ≈1. To make a more detailed estimate of the optimal liquid thickness we calculate the expected SNR of the O K core-loss edge using simulated EEL spectra assuming the atomic density of oxygen for water. The SNR is determined by calculating the expected O K signal over a 30 eV window using hydrogenic cross sections while the noise is calculated from the square root of the intensity under the same window, including the background contribution. The background intensity is given by the sum of the energy losses due to the Si L edge at 99 eV, the N K edge at 402 eV and the combined multiple scattering from core loss and plasmon losses. To approximate the background intensity including multiple scattering, the core-loss spectrum from the $SiN_x$ membrane is simulated and convoluted with a simulated low-loss spectrum. The low-loss spectrum is simulated as a series of Gaussian plasmon peaks where the total plasmon intensity is determined by Poisson statistics for a given $t/\lambda$. The value of $t/\lambda$ used is the total value for the membranes and liquid, again calculated using an Iakoubovskii approximation. All the calculations are performed using computer programs for the core-loss edges are approximated by using the Sigmal3 and Sigmak3 hydrogenic cross section programs and the low-loss is simulated by a SpecGen program. The simulations indicate an optimal O K SNR for a liquid thickness of ≈100 nm which corresponds to a total $t/\lambda$ value of 0.9 (FIG. 1). For low-loss EELS where energy-loss features from the liquid and the membrane will overlap, the membrane thickness should be minimized to prevent mechanical deformation or fracture and the limits of the fabrication approach.

To estimate the capabilities of this liquid cell for core-loss spectroscopy of a nanoparticle in liquid, we calculated the expected SNR for $Fe_2O_3$ for a cell with a 250 nm thick liquid layer and estimate that a 2 nm thick nanoparticle should produce a detectable signal for 1 nA of beam current, a 5 s dwell time and a 20 eV window over the Fe $L_{2,3}$ edge.

The liquid layer thickness can be adjusted during the fabrication over a wide range, depending on whether spectroscopic information is needed from the liquid itself, or from nanoparticles in solution; thinner liquid layers being preferred for EELS analysis of nanoparticles and thicker layers for EELS of the liquid. Reducing the liquid-layer thickness below a certain value, however, will not be worthwhile if the membrane thickness cannot be reduced because the scattering from the membrane will determine the SNR for small liquid layer thicknesses.

For EELS analysis of the low-loss region for liquids where features from the membrane and the liquid will overlap it will be advantageous for low-loss scattering from the liquid to dominate, requiring that the liquid $t/\lambda$ be greater than that of the membrane, if $\lambda$ is determined primarily by the low-loss intensity. For 50 nm $SiN_x$ membranes and water, the liquid layer thickness should be at least 130 nm. Low-loss intensity from the membrane can be removed from a spectrum of the liquid by deconvolving a membrane-only reference spectrum though there will always be some loss in SNR.

Ultimately, the precise values of the desired liquid thickness will depend on the liquid or nanoparticles being studied and the experiment to be conducted. Using calculations of SNR for the O K edge from water gives an optimal liquid thickness of ≈100 nm and based on considerations for low-loss spectroscopy the liquid thickness should be at least 130 nm. A good target liquid thickness for EELS is then in the range of 100 nm to 200 nm. In this thickness range the Fe L signal should be detectable for hematite nanoparticles≈2 nm in thickness.

Figure 56:
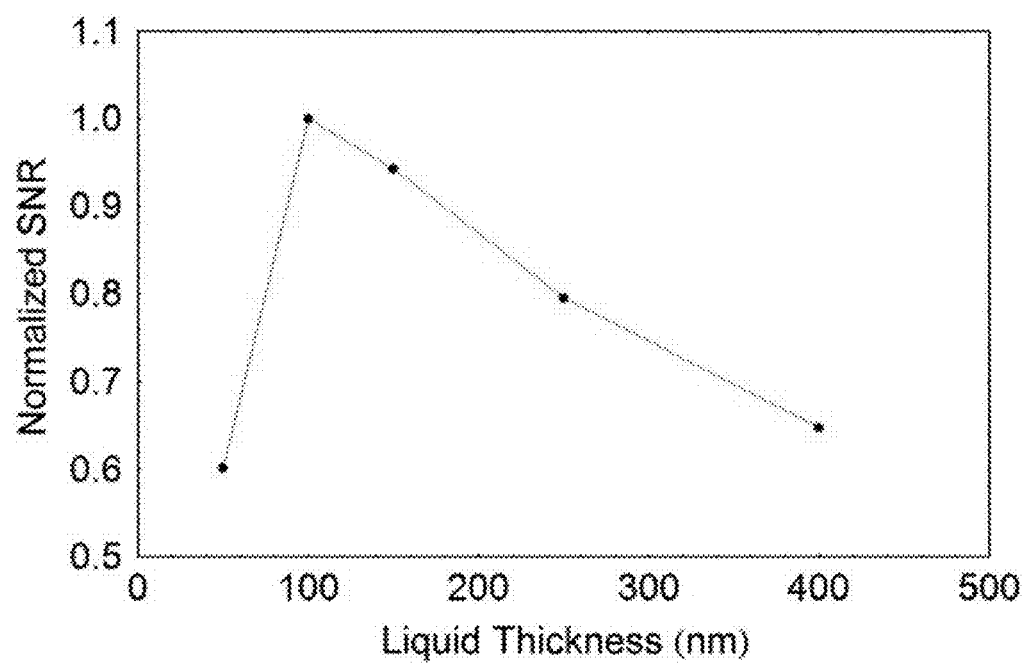
FIG. 56 shows a graph of signal-to-noise ratio versus liquid thickness.

FIG. 56 shows an estimated SNR normalized to the maximum value for the O K edge as a function of liquid thickness for a cell with two 50 nm SiN membranes. Optimal liquid thickness for studying the O K edge of liquids is ≈100 nm.

The sample cell is designed to resist mechanical failure. SiN membranes have high strength and exhibit a high level of fracture toughness. In conventional cell designs, windows are unsupported across the viewing area (supported only at the edges of the window) and are subject to pressure-driven bulging. The relationship between membrane deflection and pressure, for a square membrane, is given by $$P = \frac{393 t \delta \sigma_0}{a^2} + \frac{1.834 E t \delta^3}{(1-v) a^4} \qquad (1)$$

where $\sigma_0$ is the initial stress in the membrane, E the Young's modulus, v the Poisson's ratio, t the thickness, a the half-width of the membrane, and $\delta$ the deflection (note that for a given value of a, the deflection is approximately a factor of 2 larger for a long rectangular membrane). Equation 1 is valid for the situation when the thickness t is much smaller than the half-width, a; for smaller widths, finite-element analysis (FEA) is necessary. The options for controlling the deflection are limited: the size of membrane, a, can be reduced, or the initial stress increased.

Reducing the width of the membrane below approximately 20 μm is impractical for fabrication reasons (typical wafer thickness variations cause membrane widths to vary by as much as a factor of two at these sizes), while the initial stress cannot be increased above 1 GPa without compromising the strength of the membrane. Even for a long rectangular SiN membrane of width 20 μm, thickness 50 nm, and initial stress of 0.3 GPa, the center deflection for each membrane will be approximately 140 nm under 1 atmosphere, translating to an undesirable liquid layer thickness variation of more than 200% for an initial cavity thickness of 100 nm.

Figure 57:
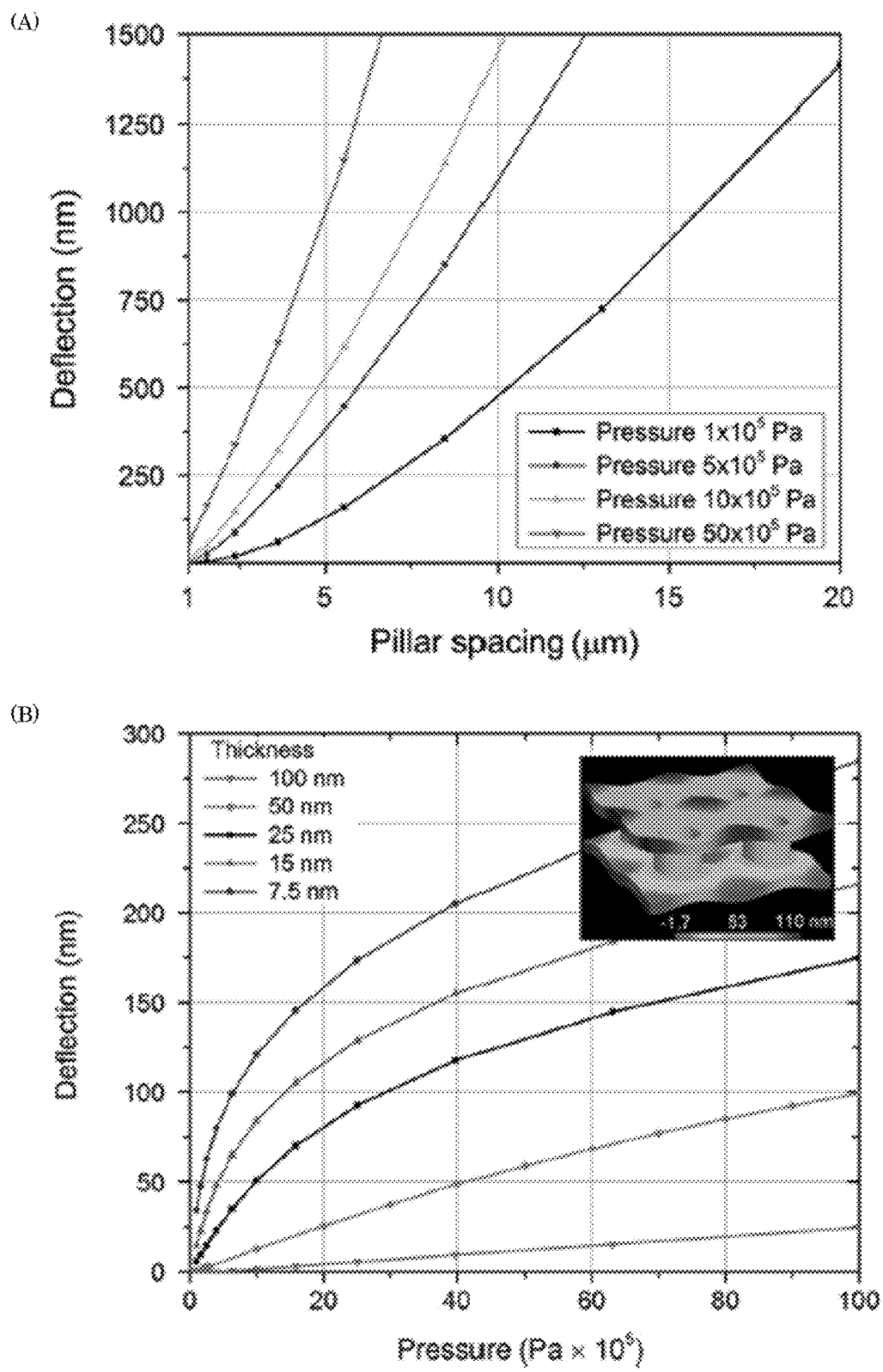
FIG. 57 shows a graph of deflection versus spacing in panel A and a graph of deflection versus pressure in panel B.

Instead of reducing the total membrane width to the level of a few micrometers, a more suitable alternative to achieve the desired small membrane deflections is to introduce regular support structures to periodically connect the upper and lower membranes, equivalent to reducing the width, a, in equation 1, while permitting the total membrane width and viewing area to remain large (hundreds of micrometers). FEA calculations for a pillar-supported, monolithic cell show that membrane deflections can be reduced to acceptable levels (≤20 nm for $10^5$ Pa (1 atm) pressure) once the pillar-to-pillar separation is reduced below 2 μm to 3 μm (FIG. 57). This decouples the size of the viewing area from membrane deflection and enables precise control over the liquid layer thickness. FIG. 57 shows (panel A) membrane deflection as a function of pillar spacing for different pressures, and panel B shows membrane deflection as a function of pressure for membranes of different thicknesses and a constant pillar edge-to-edge spacing of 1 μm. In all cases the initial membrane stress is 180 MPa. The inset shows a finite element simulation of the deflections of a structure with a membrane thickness of 50 nm and a support pillar pitch and edge-to-edge spacing of 2 μm and 1 μm respectively. The vertical displacements in the image are exaggerated by 5× for clarity.

Figure 58:
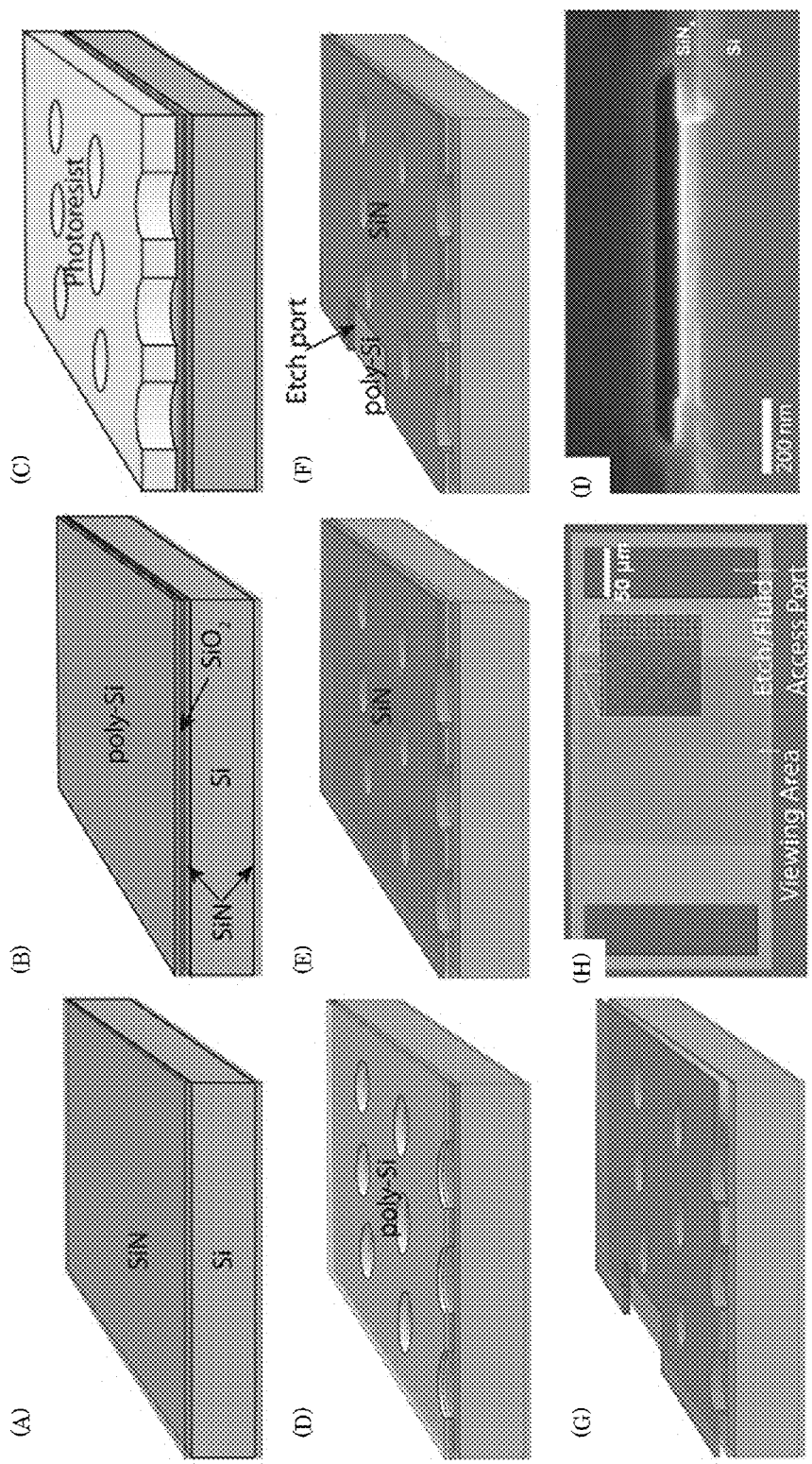
FIG. 58 shows structures formed in making a sample cell.

With reference to FIG. 58, the sample cell was fabricated by first depositing a layer of SiN, followed by a layer of silicon oxide and a layer of polysilicon. Holes are then etched through the poly-Si/$SiO_2$ bilayer to the underlying SiN before the second SiN membrane layer is deposited. Two etch ports are opened in the upper layer of SiN on either side of the viewing area, and out of the electron beam path. A hot KOH etch is then used to leach out the poly-Si/$SiO_2$ bilayer, leaving a cavity with a precisely controlled height. Because SiN etches very slowly as compared to Si in KOH (3.3 nm/h versus 2.2 μm/min), lateral etches over hundreds of micrometers are possible in a relatively short time (≈2 hours), without compromising the SiN membranes, enabling the creation of cells with large viewing areas. The etch ports also serve as in/outlets for a microfluidic system.

Again, FIG. 58 shows fabrication of the sample cell for fluids in which (panel A) LPCVD SiN is deposited on both sides of a Si wafer; panel B shows deposition of sacrificial bilayer of poly-Si/$SiO_2$, wherein poly-Si etches laterally rapidly in KOH, leaving the thin $SiO_2$ layer to be etched vertically, and $SiO_2$ layer acts as a protective layer should metal patterns be used on the lower SiN layer; panel C shows bilayer patterning via photolithography and reactive ion etching; panel D shows photoresist removal; panel E shows second LPCVD SiN deposition; panel F shows etch ports formed in upper SiN layer by photolithography and reactive ion etch; panel G shows removal of sacrificial layer by KOH etch; panel H shows an optical micrograph of completed device (overall width=2 mm); inset shows higher magnification view of pillar-supported membrane, wherein pillar spacing is 1 nm edge-to-edge, and panel I shows a scanning electron microscope image of cross-section of cavity between two pillars.

The small spacing between the membrane supports not only helps to keep deflections at the few-nanometer level (<10 nm) when the cell is in operation, it also serves to prevent capillary forces from collapsing and sticking together the membranes when the cell is dried after etching, or when fluid is introduced during sample loading. The Young-Laplace pressure for a cylindrical meniscus of radius r and surface energy γ is γ/r. For water (γ=0.073 J/$m^2$ at 20° C.) the pressure difference across the meniscus in a 100 nm tall cavity is approximately $1.5 \times 10^6$ Pa (15 atm). Using Equation (1) and ignoring corrections for large deflections, this constrains the maximum distance between supports to be less than 3 μm for 100 nm thick membranes. An attractive feature of such a cell is its ability to support very high pressures—up to $5 \times 10^6$ Pa (≈50 atm) before there is any danger of the membrane breaking. This may permit the observation of catalytic processes that occur at high pressure. Once completed, the cells can be loaded via a pulled-glass micropipette and filled by capillary action through the etch ports. The cells may then be sealed with UV-curing resin, or, if fluid flow is desired, with a microfluidic system.

To demonstrate the capabilities of the cell, we have performed high-resolution imaging in both TEM and STEM modes using suspensions of Ag nanoparticles in water/isopropanol mixtures, and collected images and EELS data from $Fe_2O_3$ nanorods in water/ethanol. The data were collected at 300 keV using both an ETEM equipped with an aberration corrector for the image-forming lens and a non-corrected TEM, both with imaging filters, and with the liquid cell in static (no-flow) mode. The HRTEM images were collected with a parallel beam (convergence semi-angle α=0 mrad) on the aberration-corrected ETEM. The HR-STEM images were collected using an annular dark-field detector with collection semi-angles between 30 mrad and 75 mrad, and a condenser aperture-spot size combination capable of a nominal resolution of 0.136 nm. EELS data in STEM mode (shown in panel A of FIG. 59) were collected with a collection semi-angle β=21 mrad and convergence semi-angle α=10 mrad. Additional EELS data were also acquired in TEM mode with α=2.6 mrad and β=9.6 mrad (shown in panel B of FIG. 59). EELS data acquired under these conditions were also used to calculate the hematite nanorod oxidation state.

Figure 59:
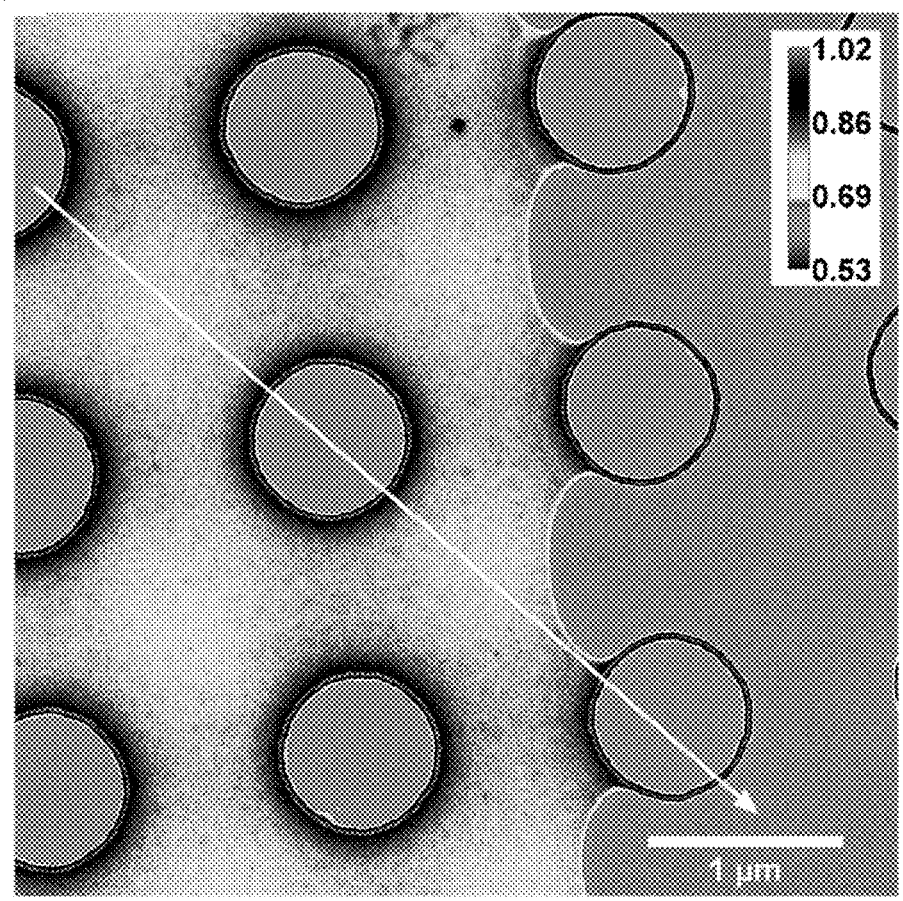
FIG. 59 shows a micrograph of a viewing reservoir in panel A and a graph of thickness there is a distance and panel B.
Figure 59:
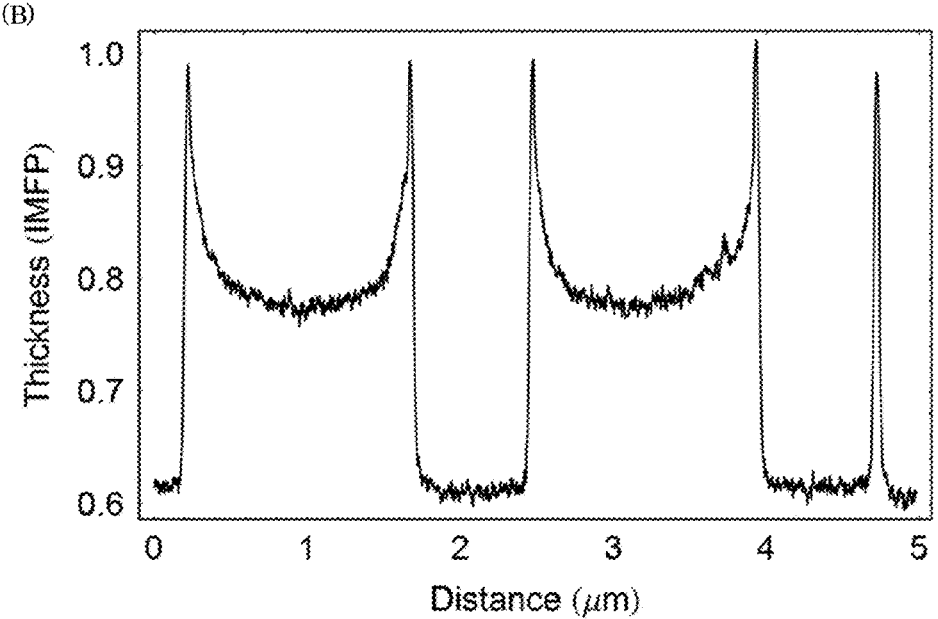

With regard to FIG. 59, panel A shows energy-filtered TEM t/λ map of a cell partially-filled with a water/isopropanol mixture showing the liquid meniscus. The calibration bar is in units of t/λ. Panel B shows a thickness profile taken along the line in panel A. (IMFP: Inelastic mean free path). The maximum reduction in liquid layer thickness caused by capillary forces in the liquid-filled region is approximately 25 nm. The deflection in the vapor-filled region at $10^5$ Pa (≈1 atm) is negligible.

Figure 60:
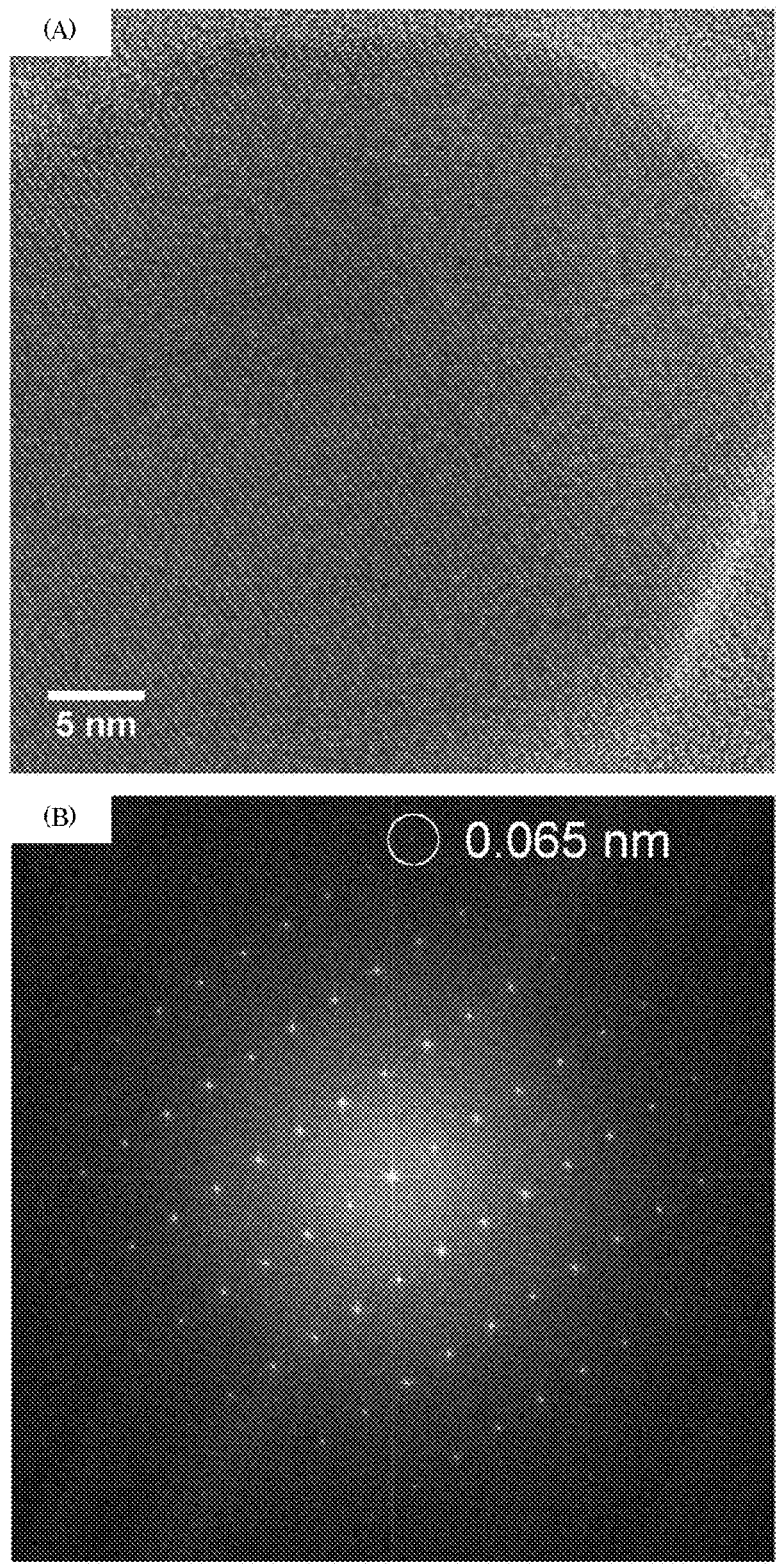
FIG. 60 shows a transmission electron microscope image of a nanorod in panel A and a Fourier Transform of the image in panel B.

With regard to FIG. 60, panel A shows an HRTEM image of an $Fe_2O_3$ nanorod. Panel B shows a Fourier transform of the image in panel A demonstrating the presence of lattice fringes out to a spacing of 0.065 nm.

Panel a of FIG. 59 is a thickness map of a liquid-filled cell near a boundary with a vapor-containing region and a line profile of the map is shown in panel B. The regular array of support pillars is seen and the liquid region is on the left-hand side of the image. The thickness profile indicates that the membranes are bowed inward, rather than outward, due to the capillary force of the liquid. The t/λ value in the liquid region decreases from ≈0.9 near the pillar to ≈0.8 between the pillars. Using a known value of the liquid thickness near the pillar and accounting for the 100 nm of SiN in the beam path indicates a λ value of ≈330 nm for the liquid mixture of water and ethanol. This value is significantly larger than values calculated for liquid water using various approximations derived from measurements on solids, and the experimentally measured value for liquid water is ≈400 nm. Using this λ value we can deduce a variation in the liquid layer thickness from 90 nm to 66 nm going from the pillar edge to between the pillars. No significant variation in these values was measurable across the entire cell viewing area.

FIG. 59 shows the HRTEM image and corresponding fast Fourier transform (FFT) demonstrating lattice fringes out to 0.065 nm of a 40 nm diameter $Fe_2O_3$ nanorod. The image was acquired with a total SiN thickness of 100 nm, and a liquid-layer thickness of ≈80 nm (≈40 nm over the nanorod) in the beam path. 10 frames were aligned and summed for the image to improve the SNR giving a total acquisition time of 2.5 s. The membrane and liquid contribute a background and noise, but do not prevent high-resolution imaging. We note that the observation of a peak in the FFT corresponding to 0.065 nm does not indicate a resolution of 0.065 nm, but does demonstrate good stability of the system. For thick liquid cells, the best resolution in TEM mode is achieved for particles on the lower membrane, while the opposite is true for STEM. For a particle on the bottom membrane, beam broadening in the upper membrane and liquid degrades the STEM resolution; in TEM mode, the image of a particle on the upper membrane is degraded by broadening as the electrons pass through the liquid and lower membrane. STEM images using an annular dark-field (ADF) detector offer better signal-to-noise than TEM images for thick samples and have therefore been preferred previously for imaging in thick liquid layers. To explore the range of applicability of the top-bottom criterion we have performed lattice imaging in both STEM and TEM modes at various locations across the cell membrane area and we find that lattice resolution is attainable on the same object in both TEM and STEM, repeatedly and reproducibly. FIG. 60 shows an example of a cluster of Ag nanoparticles exhibiting 0.24 nm lattice fringes ((111) planes of Ag) in both TEM and STEM images. This demonstrates that the "top-bottom" effect is negligible for an appropriately designed cell.

Figure 61:
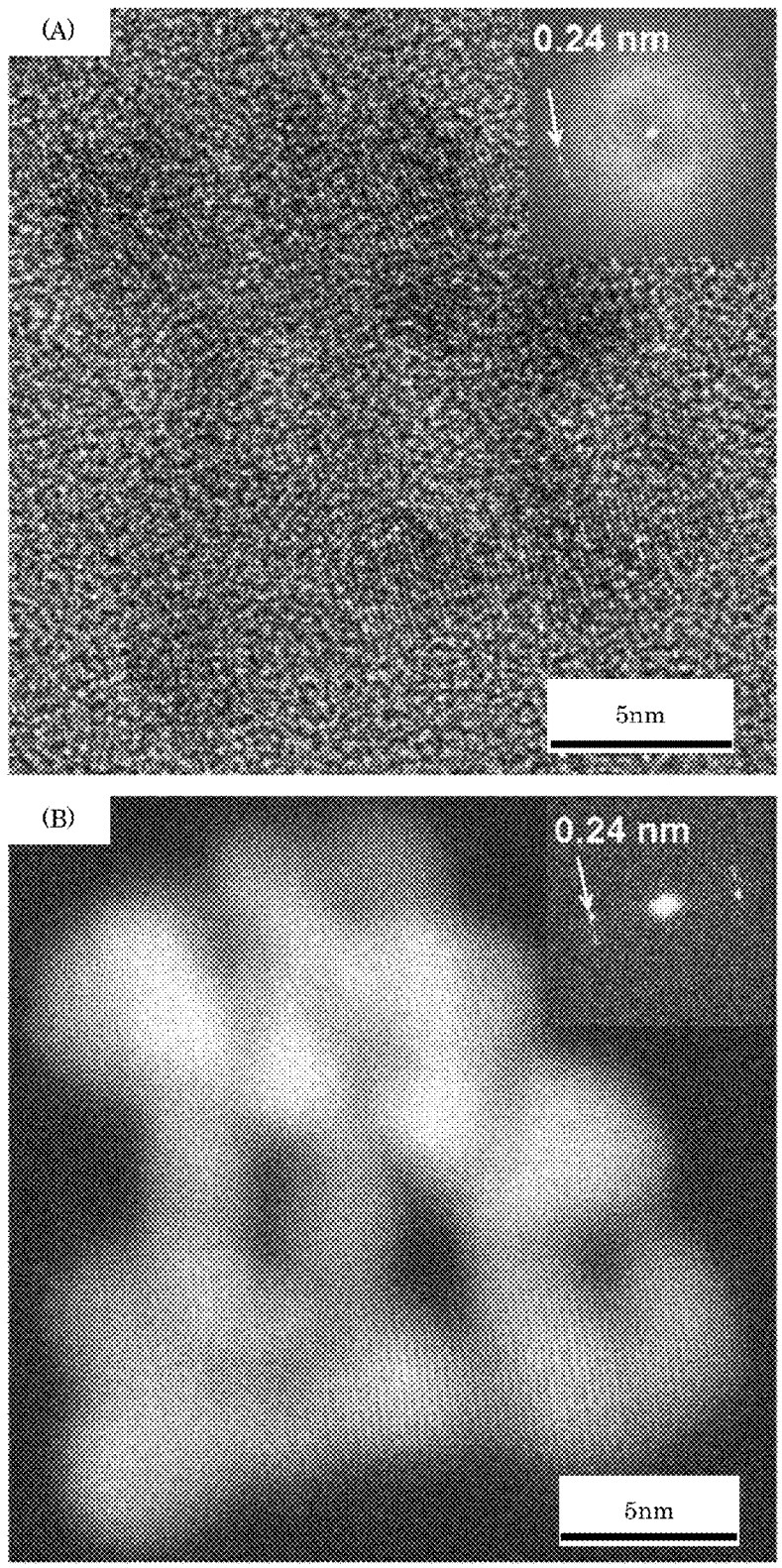
FIG. 61 shows a transmission electron microscopic image of a nanoparticle cluster in panel A and a high-resolution scanning transmission electron microscope image of the nanoparticle cluster.

With reference to FIG. 61, panel A shows an HRTEM image of an Ag nanoparticle cluster in liquid. Panel B shows an HRSTEM images of the same cluster imaged in panel A. Both images show lattice-fringe resolution of 0.24 nm. The insets are the Fast Fourier Transforms of the images demonstrating the resolution.

Figure 62:
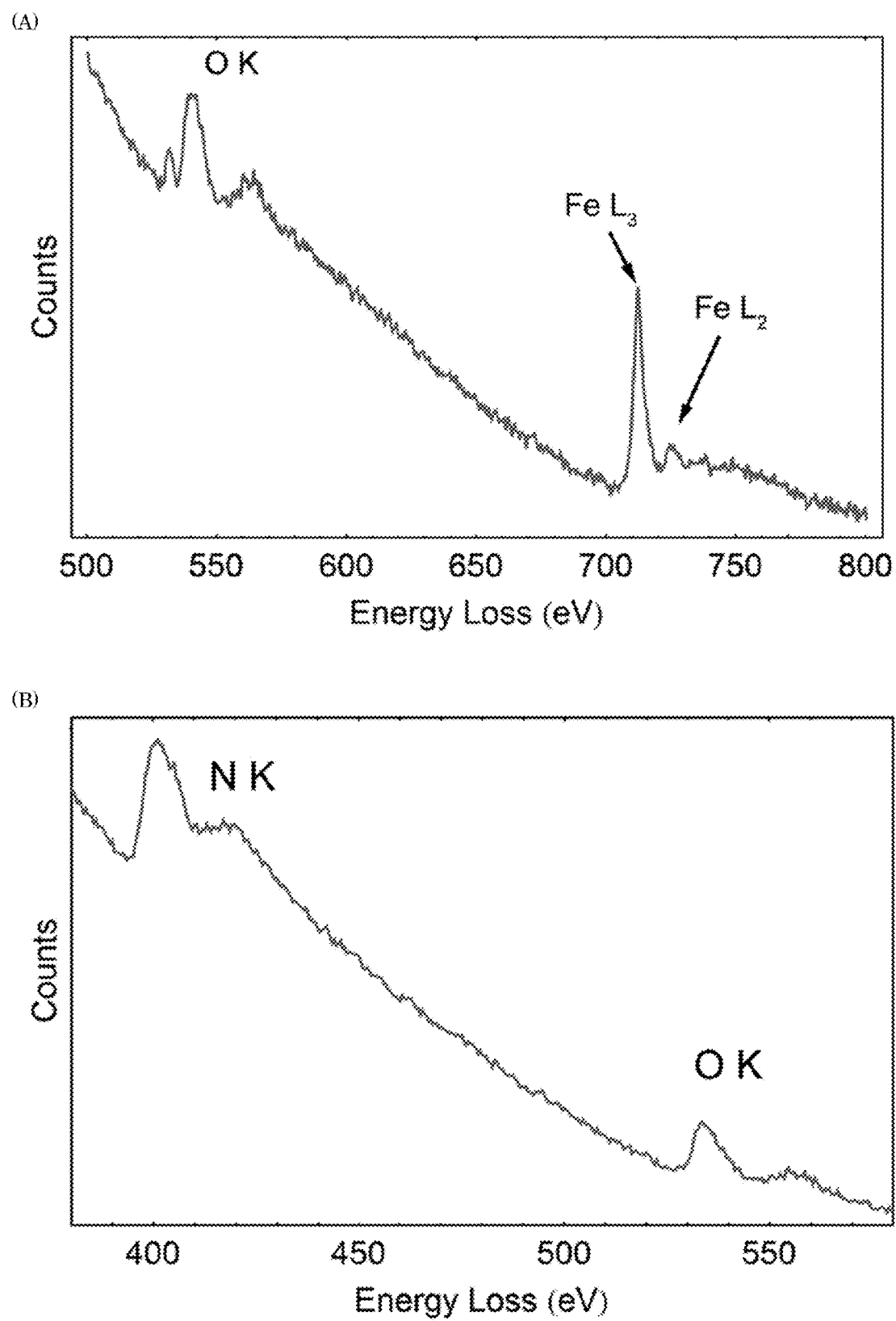
FIG. 62 shows a graph of counts versus energy loss in panel A and a graph of counts versus energy loss in panel B.

With reference to FIG. 62, panel A shows a core-loss EELS spectrum of an iron oxide nanoparticle in liquid. The ratio between the $L_2$ and $L_3$ peaks enables the identification of the iron oxidation state as $Fe^{3+}$. Panel B shows core-loss EELS spectrum from the liquid showing an N peak from the SiN membrane and an O peak generated primarily by the liquid.

Figure 63:
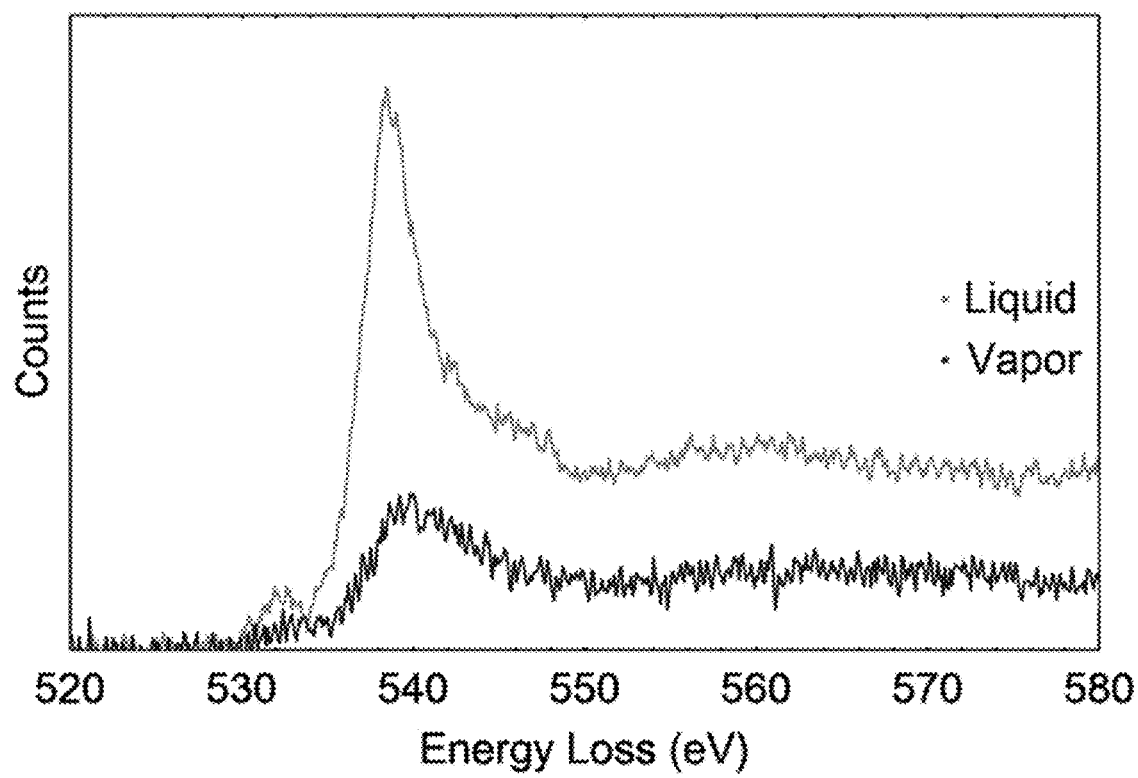
FIG. 63 shows a graph of counts versus energy loss.

FIG. 63 shows O K edge EELS data from a liquid-containing region and a vapor-containing region of the same liquid cell after deconvolution and intensity normalization. Some of the O K signal (the vapor spectrum) comes from the $SiN_x$ membranes.

Both core-loss and low-loss EELS on particles in liquid and liquids alone are possible with the cell. Panel A of FIG. 61 shows EELS data obtained from a ≈40 nm diameter $Fe_2O_3$ nanorod in water/isopropanol acquired with a total exposure time of 20 s. Near-edge fine structure is observable in both the O K edge at 532 eV and the Fe $L_{2,3}$ edge at 708 eV despite the background from the liquid and membranes. Quantification of the Fe oxidation state is possible by measurement of the Fe L white-line ratio. A method of white-line quantification was applied to a spectrum from a hematite nanorod obtained with a 0.1 eV/channel dispersion; after background subtraction and Richardson-Lucy deconvolution with the low-loss spectrum, a double arc tan function was used to subtract the continuum contribution under the white lines and the integrated intensity for the $L_2$ and $L_3$ peaks was obtained with 2 eV windows. The calculated $L_3$:$L_2$ ratio is 5.67±0.1 (uncertainty is given as ±one standard deviation). The uncertainty estimates are determined by assuming the uncertainty in the intensity values for each peak is given by the square root of the intensity (Poisson statistics). Noise contributed from the increased background intensity will increase the quantification uncertainty relative to measurements in high-vacuum conditions. However, this confirms that quantitative analysis of the near-edge structure from particles within a liquid cell is possible. Panel B of FIG. 62 shows core-loss EELS data from a liquid mixture of water and ethanol. In the core-loss spectrum the N K edge from the membrane is visible as well as a small O K edge primarily from the liquid. The membrane also contributes to the O K edge, but detailed comparison between spectra from empty cells (membranes only) and from cells filled with the ethanol-water mixture indicates the O K intensity increases by more than a factor of 2 when the cell is filled with liquid. FIG. 63 shows two spectra from a cell filled with a water/ethanol mixture, one from a liquid-containing region and one from a nearby vapor-filled region; after deconvolution with the low-loss spectrum and normalization of the intensities, it is possible to determine the O K contribution from the liquid itself. The thin vapor layer in parts of the cell contributes a negligible O signal so the O signal from the vapor region is from O in the membranes.

Vapor formation during imaging can create small regions of vapor under the beam and this process can ultimately limit the time available for data acquisition from a sample in liquid. Although this was occasionally observed during imaging with this cell, the data shown here were not acquired from regions where bubble formation occurred.

While one or more embodiments have been shown and described, modifications and substitutions may be made thereto without departing from the spirit and scope of the invention. Accordingly, it is to be understood that the present invention has been described by way of illustrations and not limitation. Embodiments herein can be used independently or can be combined.

Reference throughout this specification to "one embodiment," "particular embodiment," "certain embodiment," "an embodiment," or the like means that a particular feature, structure, or characteristic described in connection with the embodiment is included in at least one embodiment. Thus, appearances of these phrases (e.g., "in one embodiment" or "in an embodiment") throughout this specification are not necessarily all referring to the same embodiment, but may. Furthermore, particular features, structures, or characteristics may be combined in any suitable manner, as would be apparent to one of ordinary skill in the art from this disclosure, in one or more embodiments.

All ranges disclosed herein are inclusive of the endpoints, and the endpoints are independently combinable with each other. The ranges are continuous and thus contain every value and subset thereof in the range. Unless otherwise stated or contextually inapplicable, all percentages, when expressing a quantity, are weight percentages. The suffix "(s)" as used herein is intended to include both the singular and the plural of the term that it modifies, thereby including at least one of that term (e.g., the colorant(s) includes at least one colorants). "Optional" or "optionally" means that the subsequently described event or circumstance can or cannot occur, and that the description includes instances where the event occurs and instances where it does not. As used herein, "combination" is inclusive of blends, mixtures, alloys, reaction products, and the like.

As used herein, "a combination thereof" refers to a combination comprising at least one of the named constituents, components, compounds, or elements, optionally together with one or more of the same class of constituents, components, compounds, or elements.

All references are incorporated herein by reference.

The use of the terms "a" and "an" and "the" and similar referents in the context of describing the invention (especially in the context of the following claims) are to be construed to cover both the singular and the plural, unless otherwise indicated herein or clearly contradicted by context. "Or" means "and/or." Further, the conjunction "or" is used to link objects of a list or alternatives and is not disjunctive; rather the elements can be used separately or can be combined together under appropriate circumstances. It should further be noted that the terms "first," "second," "primary," "secondary," and the like herein do not denote any order, quantity, or importance, but rather are used to distinguish one element from another. The modifier "about" used in connection with a quantity is inclusive of the stated value and has the meaning dictated by the context (e.g., it includes the degree of error associated with measurement of the particular quantity).

What is claimed is:

1. A process for selectively removing a sacrificial member from a composite structure, the process comprising:
   providing a first structural layer;
   disposing the sacrificial member on the first structural layer, the sacrificial member consisting essentially of chromium oxide;
   disposing a second structural layer on the sacrificial member such that:
      the sacrificial member is interposed between the first structural layer and the second structural layer, and
      a composite structure is formed by the first structural layer and the second structural layer;
   contacting the sacrificial member with an etchant, the etchant being selective to etch chromium oxide and substantially inert with respect to etching the composite structure; and
   selectively etching the sacrificial member by the etchant to selectively remove the sacrificial member from the composite structure,
   wherein the first structural layer and the second structural layer are spaced apart by a separation distance by removal of the sacrificial member.

2. The process of claim 1, further comprising:
   disposing the first structural layer on a substrate;
   disposing an oxide layer on the first structural layer;
   disposing an electrode on the oxide layer such that the sacrificial member is partially disposed on the electrode.

3. The process of claim 2, further comprising:
   patterning the sacrificial member with a plurality of apertures prior to disposing the second structural layer.

4. The process of claim 3, further comprising:
   forming a plurality of pillars by disposing the second structural layer in the apertures of the sacrificial member.

5. The process of claim 1, further comprising:
   etching a fluid port in the substrate.

6. The process of claim 1, further comprising:
   forming a viewing reservoir by selectively removing the sacrificial member; and
   connecting the fluid port in the substrate to the viewing reservoir by selectively removing the sacrificial member such that the fluid port is in fluid communication with the viewing reservoir.

7. The process of claim 1, wherein the composite structure comprises a sample cell in which the viewing reservoir and the fluid port receive a fluid.

8. A process for making a sample cell, the process comprising:
   providing a substrate;
   disposing a first structural layer on a second surface of the substrate;
   disposing a third structural layer on the first surface of the substrate;
   disposing a first oxide layer on the first structural layer;
   disposing a plurality of electrodes on the first oxide layer;
   disposing a sacrificial member on the first oxide layer, the sacrificial member of chromium oxide and having:
      a first thickness in contact with a portion of each electrode; and
      a second thickness that is less than then the first thickness in an area on the substrate that corresponds to a viewing reservoir;
   forming a plurality of apertures in the sacrificial member;
   disposing a second oxide layer on the sacrificial member such that the sacrificial member is interposed between the second oxide layer and the first structural layer;
   disposing a second structural layer on the second oxide layer such that the sacrificial member is interposed between the second structural layer and the first structural layer;
   etching the third structural layer to expose the substrate at the first surface;
   forming an etchant trench on the second surface;
   etching a portion of the substrate from the first surface to the second surface to expose a portion of the first structural layer in an area that corresponds to a viewing reservoir and a fluid port; and
   selectively etching the sacrificial member removing the sacrificial member from between the first structural layer and the second structural layer to form the sample cell.

9. The process of claim 8, further comprising:
   disposing a third oxide layer on the second surface to fill the etchant trench.

10. The process of claim 9, further comprising:
    disposing a protective layer on the third oxide layer.

11. The process of claim 10, further comprising:
    patterning the protective layer.

12. The process of claim 11, further comprising:
    etching the third oxide layer to expose the viewing reservoir.

13. The process of claim 12, further comprising:
    etching the third oxide layer to expose the electrodes.

14. The process of claim 13, further comprising:
    etching the third oxide layer to expose the viewing reservoir.

15. The process of claim 14, wherein the viewing reservoir of the sample cell comprises:
    a first view membrane disposed on the first surface of the substrate;
    a second view membrane disposed on the second surface of the substrate; and
    a pillar interposed between the first view membrane and the second view membrane, the pillar separating the first view membrane from the second view membrane at a substantially constant separation distance that is invariable with respect to a temperature and invariable with respect to a pressure to which the sample cell is subjected, wherein the pillars, the first view membrane, and the second view membrane are monolithic.

16. The process of claim 14, wherein the substrate comprises silicon, silicon dioxide, glass, fused silica, silicon carbide, sapphire, gallium arsenide, indium phosphide, or a combination comprising at least one of the foregoing materials.

17. The process of claim 14, wherein the first structural layer, the second structural layer, and the third structural layer independently comprise silicon nitride, silicon, silicon dioxide, silicon carbide, boron nitride, graphene diamond, or a combination comprising at least one of the foregoing materials.

18. The process of claim 14, wherein the first oxide layer, the second oxide layer, and the third oxide layer independently comprise silicon dioxide, silicon, silicon carbide, boron nitride, graphene diamond, or a combination comprising at least one of the foregoing materials.

19. The process of claim 14, wherein the electrodes comprise a transition metal, gold, platinum, tungsten, or a combination comprising at least one of the foregoing materials.

20. The process of claim 14, wherein the protective layer comprises silicon dioxide, a polymer, silicon nitride, silicon, silicon carbide, silicon oxygen nitrides ($SiO_xN_y$, wherein x and y are positive real numbers), graphene diamond-like carbon, or a combination comprising at least one of the foregoing materials.

* * * * *